(12) United States Patent
Loeffler et al.

(10) Patent No.: US 8,883,416 B2
(45) Date of Patent: Nov. 11, 2014

(54) ISOLATED REDUCTIVE DEHALOGENASE GENES

(75) Inventors: Frank Loeffler, Decatur, GA (US); Kirsti M. Ritalahti, Atlanta, GA (US); Rosa Krajmalnik-Brown, Chandler, AZ (US); Ivy Thomson, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 2094 days.

(21) Appl. No.: 11/575,156

(22) PCT Filed: Sep. 14, 2005

(86) PCT No.: PCT/US2005/033063
§ 371 (c)(1),
(2), (4) Date: Feb. 9, 2009

(87) PCT Pub. No.: WO2006/031997
PCT Pub. Date: Mar. 23, 2006

(65) Prior Publication Data
US 2010/0015599 A1    Jan. 21, 2010

Related U.S. Application Data

(60) Provisional application No. 60/609,892, filed on Sep. 14, 2004.

(51) Int. Cl.
*C12Q 1/68* (2006.01)
*C12N 1/21* (2006.01)
*C12N 15/63* (2006.01)
*C07H 21/04* (2006.01)

(52) U.S. Cl.
USPC ............... 435/6.11; 435/252.3; 435/320.1; 536/23.2

(58) Field of Classification Search
CPC .... C12Q 1/04; C12Q 1/68; C12Y 197/01008; C12N 9/004
USPC ................ 435/6.11, 252.3, 320.1; 536/23.2
See application file for complete search history.

(56) References Cited

U.S. PATENT DOCUMENTS

2003/0165893 A1* 9/2003 Nakamura et al. ................ 435/6

OTHER PUBLICATIONS

Magnuson et al. Appld and Envirion Microbiol. 2000, pp. 5141-5147.*
International Search Report and Written Opinion of the International Searching Authority of related application PCT/US05/33063 mailed Nov. 28, 2006.
Krajmalnik-Brown et al.; Genetic Identification of a Putative Vinyl Chloride Reductase in Dehalococcoides sp. Strain BAV1; Applied and Env. Microbiology; Oct. 2004; p. 6347-6351; vol. 70, No. 10; American Society for Microbiology.

* cited by examiner

*Primary Examiner* — Tekchand Saidha
*Assistant Examiner* — Md. Younus Meah
(74) *Attorney, Agent, or Firm* — Fenwick & West LLP

(57) ABSTRACT

The invention is directed to novel reductive dehalogenase genes encoding for reductive dehalogenases which are capable of dehalogenating halogenated organic compounds and may be useful in the bioremediation of pollutants. In particular, the invention provides an isolated polynucleotide of a novel vinyl chloride dehalogenase gene (bvcA). The novel vinyl chloride dehalogenase gene encodes a reductive dehalogenase that is capable of the complete reduction of vinyl chloride to ethene.

18 Claims, 12 Drawing Sheets

Figure 5A

| Sequences | 1 | 2 | 3 | 4 | 5 | 6 | 7 | 8 | 9 | 10 |
|---|---|---|---|---|---|---|---|---|---|---|
| 1 RDA13 | 1.00 | 0.32 | 0.25 | 0.52 | 0.36 | 0.28 | 0.79 | 0.60 | 0.60 | 0.34 |
| 2 RDA1 | 0.34 | 1.00 | 0.65 | 0.31 | 0.44 | 0.49 | 0.38 | 0.36 | 0.40 | 0.61 |
| 3 RDA2 | 0.25 | 0.63 | 1.00 | 0.24 | 0.39 | 0.38 | 0.27 | 0.26 | 0.30 | 0.53 |
| 4 RDA10 | 0.53 | 0.35 | 0.24 | 1.00 | 0.26 | 0.21 | 0.49 | 0.47 | 0.48 | 0.29 |
| 5 RDA5 | 0.42 | 0.48 | 0.47 | 0.30 | 1.00 | 0.59 | 0.41 | 0.48 | 0.38 | 0.70 |
| 6 RDA4 | 0.34 | 0.56 | 0.48 | 0.24 | 0.60 | 1.00 | 0.33 | 0.26 | 0.34 | 0.79 |
| 7 RDA | 0.82 | 0.34 | 0.28 | 0.48 | 0.36 | 0.27 | 1.00 | 0.67 | 0.63 | 0.37 |
| 8 RDA12 | 0.59 | 0.36 | 0.30 | 0.48 | 0.42 | 0.23 | 0.66 | 1.00 | 0.56 | 0.33 |
| 9 RDA11 | 0.63 | 0.40 | 0.33 | 0.50 | 0.35 | 0.31 | 0.68 | 0.60 | 1.00 | 0.42 |
| 10 RDA6 | 0.42 | 0.72 | 0.66 | 0.34 | 0.71 | 0.79 | 0.45 | 0.38 | 0.48 | 1.00 |
| 11 RDA8 | 0.38 | 0.34 | 0.25 | 0.30 | 0.32 | 0.42 | 0.42 | 0.39 | 0.29 | 0.37 |
| 12 RDA7 | 0.42 | 0.30 | 0.28 | 0.26 | 0.26 | 0.27 | 0.35 | 0.32 | 0.35 | 0.31 |
| 13 RDA9 | 0.48 | 0.19 | 0.28 | 0.34 | 0.25 | 0.29 | 0.48 | 0.40 | 0.34 | 0.31 |
| 14 RDA3 | 0.39 | 0.68 | 0.64 | 0.34 | 0.66 | 0.86 | 0.38 | 0.35 | 0.47 | 0.90 |
| 15 RDA15 | 0.38 | 0.34 | 0.34 | 0.25 | 0.34 | 0.37 | 0.40 | 0.36 | 0.39 | 0.37 |
| 16 RDA17 | 0.23 | 0.12 | 0.14 | 0.12 | 0.18 | 0.18 | 0.16 | 0.10 | 0.22 | 0.16 |
| 17 RDA16 | 0.33 | 0.28 | 0.17 | 0.27 | 0.25 | 0.28 | 0.29 | 0.26 | 0.32 | 0.26 |
| 18 RdhA1$_{BAVI}$ | 0.65 | 0.44 | 0.32 | 0.56 | 0.33 | 0.27 | 0.56 | 0.69 | 0.55 | 0.37 |
| 19 RdhA2$_{BAVI}$ | 0.36 | 0.40 | 0.37 | 0.25 | 0.32 | 0.40 | 0.38 | 0.25 | 0.42 | 0.42 |
| 20 RdhA3$_{BAVI}$ | 0.39 | 0.30 | 0.28 | 0.29 | 0.29 | 0.33 | 0.34 | 0.30 | 0.42 | 0.36 |
| 21 RdhA4$_{BAVI}$ | 0.36 | 0.64 | 0.85 | 0.25 | 0.45 | 0.43 | 0.31 | 0.27 | 0.27 | 0.53 |
| 22 RdhA5$_{BAVI}$ | 0.42 | 0.67 | 0.66 | 0.29 | 0.74 | 0.78 | 0.42 | 0.40 | 0.50 | 1.00 |
| 23 RdhA6$_{BAVI}$ | 0.43 | 0.61 | 0.57 | 0.35 | 0.37 | 0.54 | 0.30 | 0.35 | 0.37 | 0.63 |
| 24 RdhA7$_{BAVI}$ | 0.69 | 0.37 | 0.36 | 0.52 | 0.38 | 0.25 | 0.65 | 0.75 | 0.68 | 0.34 |
| 25 TCEA | 0.44 | 0.50 | 0.50 | 0.33 | 0.43 | 0.49 | 0.35 | 0.34 | 0.36 | 0.48 |
| 26 PCEA | 0.22 | 0.22 | 0.17 | 0.20 | 0.20 | 0.22 | 0.22 | 0.28 | 0.28 | 0.20 |
| 27 PCEAb | 0.26 | 0.13 | 0.17 | 0.17 | 0.19 | 0.16 | 0.17 | 0.20 | 0.20 | 0.12 |
| 28 PCEAc | 0.26 | 0.13 | 0.17 | 0.17 | 0.18 | 0.16 | 0.17 | 0.20 | 0.20 | 0.12 |
| 29 PCEAd | 0.26 | 0.13 | 0.17 | 0.17 | 0.18 | 0.16 | 0.17 | 0.20 | 0.20 | 0.12 |
| 30 CPRAd | 0.31 | 0.22 | 0.22 | 0.25 | 0.25 | 0.26 | 0.26 | 0.29 | 0.29 | 0.24 |
| 31 CPRAc | 0.27 | 0.21 | 0.25 | 0.24 | 0.27 | 0.27 | 0.28 | 0.27 | 0.24 | 0.26 |
| 32 CprAh | 0.32 | 0.20 | 0.21 | 0.25 | 0.25 | 0.25 | 0.28 | 0.30 | 0.29 | 0.23 |
| 33 CprAV | 0.31 | 0.22 | 0.21 | 0.25 | 0.25 | 0.26 | 0.26 | 0.29 | 0.29 | 0.25 |

Figure 5B

| Sequences | 11 | 12 | 13 | 14 | 15 | 16 | 17 | 18 | 19 | 20 |
|---|---|---|---|---|---|---|---|---|---|---|
| 1 RDA13 | 0.38 | 0.43 | 0.46 | 0.32 | 0.38 | 0.22 | 0.24 | 0.64 | 0.34 | 0.42 |
| 2 RDA1 | 0.36 | 0.32 | 0.21 | 0.59 | 0.36 | 0.12 | 0.23 | 0.44 | 0.38 | 0.34 |
| 3 RDA2 | 0.25 | 0.29 | 0.26 | 0.51 | 0.37 | 0.13 | 0.15 | 0.31 | 0.36 | 0.34 |
| 4 RDA10 | 0.30 | 0.28 | 0.33 | 0.29 | 0.25 | 0.11 | 0.19 | 0.55 | 0.23 | 0.31 |
| 5 RDA5 | 0.37 | 0.32 | 0.28 | 0.65 | 0.41 | 0.20 | 0.23 | 0.39 | 0.37 | 0.36 |
| 6 RDA4 | 0.49 | 0.33 | 0.33 | 0.85 | 0.48 | 0.22 | 0.26 | 0.31 | 0.44 | 0.42 |
| 7 RDA | 0.41 | 0.35 | 0.45 | 0.31 | 0.41 | 0.16 | 0.23 | 0.54 | 0.35 | 0.36 |
| 8 RDA12 | 0.40 | 0.33 | 0.38 | 0.33 | 0.38 | 0.09 | 0.20 | 0.66 | 0.25 | 0.33 |
| 9 RDA11 | 0.30 | 0.38 | 0.35 | 0.42 | 0.43 | 0.23 | 0.23 | 0.57 | 0.43 | 0.48 |
| 10 RDA6 | 0.44 | 0.38 | 0.37 | 0.90 | 0.50 | 0.22 | 0.25 | 0.43 | 0.47 | 0.47 |
| 11 RDA8 | 1.00 | 0.42 | 0.50 | 0.42 | 0.42 | 0.21 | 0.26 | 0.39 | 0.40 | 0.47 |
| 12 RDA7 | 0.41 | 1.00 | 0.39 | 0.34 | 0.39 | 0.15 | 0.18 | 0.29 | 0.24 | 0.34 |
| 13 RDA9 | 0.52 | 0.41 | 1.00 | 0.31 | 0.37 | 0.17 | 0.25 | 0.34 | 0.32 | 0.28 |
| 14 RDA3 | 0.51 | 0.42 | 0.38 | 1.00 | 0.48 | 0.18 | 0.30 | 0.42 | 0.47 | 0.50 |
| 15 RDA15 | 0.39 | 0.39 | 0.34 | 0.36 | 1.00 | 0.21 | 0.19 | 0.35 | 0.37 | 0.37 |
| 16 RDA17 | 0.22 | 0.16 | 0.18 | 0.13 | 0.22 | 1.00 | 0.31 | 0.16 | 0.20 | 0.22 |
| 17 RDA16 | 0.33 | 0.25 | 0.35 | 0.31 | 0.25 | 0.41 | 1.00 | 0.25 | 0.38 | 0.35 |
| 18 RdhA1$_{BAVI}$ | 0.39 | 0.30 | 0.33 | 0.36 | 0.38 | 0.16 | 0.18 | 1.00 | 0.31 | 0.40 |
| 19 RdhA2$_{BAVI}$ | 0.42 | 0.26 | 0.33 | 0.42 | 0.40 | 0.20 | 0.31 | 0.33 | 1.00 | 0.53 |
| 20 RdhA3$_{BAVI}$ | 0.44 | 0.34 | 0.26 | 0.39 | 0.36 | 0.19 | 0.25 | 0.38 | 0.47 | 1.00 |
| 21 RdhA4$_{BAVI}$ | 0.33 | 0.33 | 0.26 | 0.55 | 0.41 | 0.13 | 0.22 | 0.35 | 0.43 | 0.36 |
| 22 RdhA5$_{BAVI}$ | 0.43 | 0.40 | 0.31 | 0.90 | 0.53 | 0.25 | 0.25 | 0.42 | 0.51 | 0.48 |
| 23 RdhA6$_{BAVI}$ | 0.47 | 0.41 | 0.26 | 0.58 | 0.40 | 0.17 | 0.25 | 0.38 | 0.48 | 0.47 |
| 24 RdhA7$_{BAVI}$ | 0.41 | 0.40 | 0.36 | 0.34 | 0.38 | 0.15 | 0.22 | 0.58 | 0.33 | 0.34 |
| 25 TCEA | 0.53 | 0.34 | 0.25 | 0.54 | 0.44 | 0.31 | 0.28 | 0.41 | 0.42 | 0.36 |
| 26 PCEA | 0.37 | 0.25 | 0.26 | 0.24 | 0.28 | 0.30 | 0.28 | 0.22 | 0.27 | 0.24 |
| 27 PCEAb | 0.25 | 0.19 | 0.15 | 0.15 | 0.24 | 0.26 | 0.29 | 0.17 | 0.20 | 0.23 |
| 28 PCEAc | 0.25 | 0.21 | 0.15 | 0.15 | 0.22 | 0.26 | 0.29 | 0.17 | 0.20 | 0.23 |
| 29 PCEAd | 0.25 | 0.19 | 0.15 | 0.15 | 0.22 | 0.26 | 0.29 | 0.17 | 0.20 | 0.23 |
| 30 CPRAd | 0.29 | 0.24 | 0.26 | 0.32 | 0.29 | 0.33 | 0.36 | 0.32 | 0.41 | 0.27 |
| 31 CPRAc | 0.27 | 0.30 | 0.28 | 0.35 | 0.35 | 0.31 | 0.35 | 0.31 | 0.38 | 0.26 |
| 32 CprAh | 0.30 | 0.21 | 0.30 | 0.33 | 0.29 | 0.35 | 0.38 | 0.33 | 0.41 | 0.25 |
| 33 CprAV | 0.29 | 0.22 | 0.26 | 0.32 | 0.29 | 0.33 | 0.36 | 0.32 | 0.41 | 0.27 |

Figure 5C

| Sequences | 21 | 22 | 23 | 24 | 25 | 26 | 27 | 28 | 29 | 30 |
|---|---|---|---|---|---|---|---|---|---|---|
| 1 RDA13 | 0.36 | 0.34 | 0.33 | 0.72 | 0.37 | 0.22 | 0.24 | 0.24 | 0.24 | 0.26 |
| 2 RDA1 | 0.66 | 0.55 | 0.49 | 0.42 | 0.43 | 0.23 | 0.12 | 0.12 | 0.12 | 0.21 |
| 3 RDA2 | 0.84 | 0.53 | 0.47 | 0.37 | 0.42 | 0.17 | 0.18 | 0.18 | 0.18 | 0.18 |
| 4 RDA10 | 0.25 | 0.24 | 0.27 | 0.56 | 0.29 | 0.20 | 0.17 | 0.17 | 0.17 | 0.20 |
| 5 RDA5 | 0.55 | 0.72 | 0.34 | 0.45 | 0.45 | 0.25 | 0.21 | 0.20 | 0.20 | 0.25 |
| 6 RDA4 | 0.52 | 0.78 | 0.53 | 0.33 | 0.50 | 0.27 | 0.19 | 0.19 | 0.19 | 0.26 |
| 7 RDA | 0.31 | 0.35 | 0.23 | 0.67 | 0.29 | 0.23 | 0.16 | 0.16 | 0.16 | 0.25 |
| 8 RDA12 | 0.31 | 0.34 | 0.30 | 0.82 | 0.32 | 0.28 | 0.18 | 0.18 | 0.18 | 0.26 |
| 9 RDA11 | 0.29 | 0.45 | 0.32 | 0.75 | 0.33 | 0.29 | 0.19 | 0.19 | 0.19 | 0.26 |
| 10 RDA6 | 0.65 | 1.00 | 0.60 | 0.44 | 0.52 | 0.26 | 0.14 | 0.14 | 0.14 | 0.23 |
| 11 RDA8 | 0.34 | 0.36 | 0.40 | 0.41 | 0.44 | 0.37 | 0.24 | 0.24 | 0.24 | 0.25 |
| 12 RDA7 | 0.30 | 0.32 | 0.31 | 0.41 | 0.28 | 0.24 | 0.17 | 0.19 | 0.17 | 0.19 |
| 13 RDA9 | 0.27 | 0.27 | 0.23 | 0.38 | 0.23 | 0.26 | 0.13 | 0.13 | 0.13 | 0.20 |
| 14 RDA3 | 0.68 | 0.90 | 0.58 | 0.44 | 0.56 | 0.30 | 0.18 | 0.18 | 0.18 | 0.31 |
| 15 RDA15 | 0.37 | 0.40 | 0.30 | 0.35 | 0.36 | 0.26 | 0.22 | 0.21 | 0.21 | 0.22 |
| 16 RDA17 | 0.13 | 0.18 | 0.16 | 0.17 | 0.26 | 0.30 | 0.25 | 0.25 | 0.25 | 0.29 |
| 17 RDA16 | 0.28 | 0.26 | 0.24 | 0.31 | 0.31 | 0.34 | 0.35 | 0.35 | 0.35 | 0.40 |
| 18 RdhA1$_{BAVI}$ | 0.33 | 0.35 | 0.32 | 0.63 | 0.36 | 0.22 | 0.16 | 0.16 | 0.16 | 0.28 |
| 19 RdhA2$_{BAVI}$ | 0.46 | 0.44 | 0.41 | 0.37 | 0.38 | 0.28 | 0.19 | 0.19 | 0.19 | 0.38 |
| 20 RdhA3$_{BAVI}$ | 0.32 | 0.37 | 0.34 | 0.31 | 0.29 | 0.22 | 0.21 | 0.21 | 0.21 | 0.22 |
| 21 RdhA4$_{BAVI}$ | 1.00 | 0.54 | 0.47 | 0.40 | 0.46 | 0.21 | 0.15 | 0.14 | 0.15 | 0.22 |
| 22 RdhA5$_{BAVI}$ | 0.69 | 1.00 | 0.62 | 0.46 | 0.52 | 0.26 | 0.16 | 0.16 | 0.16 | 0.25 |
| 23 RdhA6$_{BAVI}$ | 0.58 | 0.62 | 1.00 | 0.51 | 0.68 | 0.36 | 0.16 | 0.16 | 0.16 | 0.23 |
| 24 RdhA7$_{BAVI}$ | 0.38 | 0.34 | 0.39 | 1.00 | 0.33 | 0.26 | 0.18 | 0.18 | 0.18 | 0.31 |
| 25 TCEA | 0.54 | 0.49 | 0.62 | 0.43 | 1.00 | 0.39 | 0.31 | 0.31 | 0.31 | 0.31 |
| 26 PCEA | 0.22 | 0.20 | 0.29 | 0.27 | 0.35 | 1.00 | 0.33 | 0.33 | 0.33 | 0.36 |
| 27 PCEAb | 0.15 | 0.13 | 0.13 | 0.18 | 0.28 | 0.34 | 1.00 | 1.00 | 1.00 | 0.31 |
| 28 PCEAc | 0.13 | 0.13 | 0.13 | 0.20 | 0.28 | 0.34 | 1.00 | 1.00 | 1.00 | 0.31 |
| 29 PCEAd | 0.15 | 0.13 | 0.13 | 0.18 | 0.28 | 0.34 | 1.00 | 1.00 | 1.00 | 0.31 |
| 30 CPRAd | 0.27 | 0.26 | 0.22 | 0.35 | 0.32 | 0.41 | 0.35 | 0.35 | 0.35 | 1.00 |
| 31 CPRAc | 0.33 | 0.25 | 0.24 | 0.32 | 0.34 | 0.42 | 0.40 | 0.40 | 0.40 | 0.99 |
| 32 CprAh | 0.26 | 0.24 | 0.20 | 0.36 | 0.31 | 0.42 | 0.37 | 0.37 | 0.37 | 1.00 |
| 33 CprAV | 0.27 | 0.26 | 0.22 | 0.35 | 0.32 | 0.41 | 0.35 | 0.35 | 0.35 | 1.00 |

Figure 5D

| Sequences | 31 | 32 | 33 |
|---|---|---|---|
| 1 RDA13 | 0.23 | 0.27 | 0.26 |
| 2 RDA1 | 0.18 | 0.20 | 0.21 |
| 3 RDA2 | 0.21 | 0.18 | 0.18 |
| 4 RDA10 | 0.19 | 0.20 | 0.20 |
| 5 RDA5 | 0.25 | 0.25 | 0.25 |
| 6 RDA4 | 0.27 | 0.25 | 0.26 |
| 7 RDA | 0.25 | 0.24 | 0.25 |
| 8 RDA12 | 0.24 | 0.27 | 0.26 |
| 9 RDA11 | 0.20 | 0.26 | 0.26 |
| 10 RDA6 | 0.25 | 0.22 | 0.24 |
| 11 RDA8 | 0.22 | 0.26 | 0.25 |
| 12 RDA7 | 0.22 | 0.17 | 0.18 |
| 13 RDA9 | 0.22 | 0.25 | 0.20 |
| 14 RDA3 | 0.34 | 0.32 | 0.31 |
| 15 RDA15 | 0.28 | 0.23 | 0.22 |
| 16 RDA17 | 0.27 | 0.31 | 0.29 |
| 17 RDA16 | 0.38 | 0.41 | 0.40 |
| 18 RdhA1$_{BAVI}$ | 0.27 | 0.29 | 0.28 |
| 19 RdhA2$_{BAVI}$ | 0.35 | 0.37 | 0.38 |
| 20 RdhA3$_{BAVI}$ | 0.20 | 0.21 | 0.22 |
| 21 RdhA4$_{BAVI}$ | 0.26 | 0.21 | 0.22 |
| 22 RdhA5$_{BAVI}$ | 0.24 | 0.22 | 0.26 |
| 23 RdhA6$_{BAVI}$ | 0.24 | 0.21 | 0.22 |
| 24 RdhA7$_{BAVI}$ | 0.25 | 0.31 | 0.31 |
| 25 TCEA | 0.33 | 0.30 | 0.31 |
| 26 PCEA | 0.36 | 0.36 | 0.36 |
| 27 PCEAb | 0.37 | 0.34 | 0.31 |
| 28 PCEAc | 0.37 | 0.34 | 0.31 |
| 29 PCEAd | 0.37 | 0.34 | 0.31 |
| 30 CPRAd | 0.98 | 0.98 | 1.00 |
| 31 CPRAc | 1.00 | 0.96 | 0.99 |
| 32 CprAh | 0.96 | 1.00 | 1.00 |
| 33 CprAV | 0.98 | 0.98 | 1.00 |

Figure 6A

```
                       *        20         *        40         *
RDA13      LTDLPLAPDKPIDAGYFRFCHT-CRKCAEACPSQAISFDS---EPSWEIPPSSVDP  : 52
RDA        ITDLPLMPTPPIDAGIFRFCHT-CRKCAEACPVGGISFEA---EPSWEIPPSAIAT  : 52
RDA11      ITDLPLPVSKPIDFGAFRFCHS-CRKCADTCPAKAISFEE---EPTWEPAG-----  : 47
RDA12      ITDLPMAPTHPIDAGIFRFCHT-CHKCADECPAKCIDQGS---EPTWDFPASMYKP  : 52
RdhA1_BAV1 VTDLPVEPTTPIDAGIWRFCQT-CNKCAQNCPTQVIPYDK---EPSWELPTLYGKP  : 52
RdhA7_BAV1 LTDLPLTPTKPIDAGMWRFCKT-CAICAENCPSQSISYDK---EPSWEITPSKYAP  : 52
RDA10      LTDLPLEPTHPIDAGIYRFCHS-CQKCADHCPQVISKEK---EPSWDIPLTEGKE  : 52
RDA2       YTDLPLPVINPIDAGFVKFCEI-CGICAETCPVGAIQERGI--DRSWDNNC-GQSW  : 52
RdhA4_BAV1 FTDLPLSPTKPIDAGITKFCET-CGICAESCPVGAVPAKGV--NRNWDSNCDGQSF  : 53
RDA1       VTDLPLAVTKPIDAGMERFCET-CGVCGTQCPFGAIAMG----DKSWDNAC-GQDW  : 50
RdhA6_BAV1 VCDLPMVPTKPIDAGIHKFCET-CGICTTVCPSNAIQVG----PPQWSNNR----W  : 47
TCEA       LTDLPLAPTKPIDAGIREFCKT-CGICAEHCPTQAISHE----GPRYDSPH----W  : 47
RDA6       ITDMPLMATKPIDFGVYKFCQT-CGICADSCPFGLIEQG----DPSWEATQ---PG  : 48
RdhA5_BAV1 MTDMPLMSTKPIDFGVYDFCKT-CGICADACPFGLIEKG----DPTWEATQ---PG  : 48
RDA3       LTDMPLPPSRPIDFGARKFCET-CGICAENCPFGAINPG----EPTWKDDN---AF  : 48
RDA4       ITNFPIVPTKPIDFGSREFCKT-CKICAEACPFGAIKTG----DPTWEDDT---IY  : 48
RDA5       LTDLPVAPTKPIDFGAYKFCET-CGICADACPFGLIQKG----ESTWENPA---AA  : 48
RDA8       IVNLPVAPKKPIDFGARKFCIT-CKKCADLCPSGAISKE----TKLTWDIVQAYDS-  : 51
RDA9       VTDLPLPADNPIDFGVVSFCTTACKKCAEFCPVSAIKMD---SEPSWELATDPSNP  : 53
RDA7       FTDLPLPTTNPIDFGANRFCRD-CGLCAKACPASAIPT---FREPTYEITPADDAN  : 52
RDA15      LTDLPLAPTKPIDFGVLKFCST-CGVCANACPSGAIPTKEEMKEPTWERSTGPWSS  : 55
RdhA2_BAV1 VTDMPLSPTKPIDAGIVNFCKV-CKKCAETCPSGAISMET----EQQWEPACTG---  : 49
RdhA3_BAV1 LTDLPLAPTKPIDAGMWKFCQS-CKKCADMCPSGAISKEA---EPTWEPTGVW---  : 49
PCEA       FTDLPLVPDKPIDFGVTEFCET-CKKCARECPSKAITEGP----RTFEGRS-----  : 46
PCEAc      YTDLPLAPDKPRKFGVREFCRL-CKKCADACPAQAISHEK---DPKVLQPEDCEVA  : 52
PCEAd      YTDLPLAPDKPRKFGVREFCRL-CKKCADACPAQAISHEK---DPKVLQPEDCEVA  : 52
PCEAb      YTDLPLAPDKPRKFGVREFCRL-CKKCADACPAQAISHEK---DPKVLQPEDCEVA  : 52
CPRAd      TTDLPLAPDKPIDFGLLDFCRV-CKKCADNCPNDAITFDE----DPIEYN------  : 45
CprAV      TTDMPLAPDKPIDFGLLDFCRV-CKKCADNCPNDAITFDE----DPIEYN------  : 45
CprAh      TTDLPLAPDQPLDFGLLDFCRV-CKKCADNCPNEAISFDE----DPIEYN------  : 45
CPRAc      TTDLPLEPDKPIDFGLQDFCRI-CGKCAENCPGEATTTDR----DHVEFN------  : 45
RDA16      FTDLPLVPDKPIDFGLQEFCKV-CKKCADNCPASAISMDD----EPSEVDT-----  : 46
RDA17      TTSLPLAADKPVDFNLAEFCSR-CKLCAQVCPTQAISYDD---KPKFEIY------  : 46
           t  p6    P d g  FC  C Ca  CP  6
               60         *        80         *       100        *
```

Figure 6B

```
RDA13      AKET-------KYSTPGKKVHHTDSPACYSRWIGL-----------HG-KARCMGT  : 89
RDA        DKPI-------SFSTPGKRTYHTDALKCRLYFDAQ-----------PSYCARCMGT  : 90
RDA11      -----------PWSTAGKRAYFKNEPECKLYQHST-----------GATQICTGV  : 81
RDA12      EMPV-------DYHAPGKRLYWNDPIACQMYSNSV-----------AGAGGVCMAT  : 90
RdhA1_BAV1 DI---------IHPSGKRMYYANHIECWMY--CF-----------EGGGGTCMAT  : 85
RdhA7_BAV1 NVPV-------EYSVPGKKVYWRDEPSCKQWTESC-----------GYSGGICMGS  : 90
RDA10      TI---------FSVKGTKAYYNNLPLCRQYSNET-----------SHGGRICWGE  : 87
RDA2       ADDKQAGGSKVMYNIPGYKGWRCNLFSCAFTP--------------CASACKSN  : 92
RdhA4_BAV1 DNDIESGGTEVMYNVPGYKGWRVDGFRCLAD----------------CNGCKGS  : 91
RDA1       AADQSVGGDTCMWNIPGYNGWRLDYRKCMGN----------------CCSCMGA  : 88
RdhA6_BAV1 D----------NTPGYLGYRLNWGRCVLC-----------------TNCETY  : 72
TCEA       D----------CVSGYEGWHLDYHKCINC-----------------TICEAV  : 72
RDA6       TR---------PGFNGWRTNTTTCPHC------------------PVCQGS  : 72
RdhA5_BAV1 SR---------PGFNGWRTNTTICPHC------------------PVCQSS  : 72
RDA3       GN---------PGFLGWRCDYTKCPHC------------------PICQGT  : 72
RDA4       GN---------PGFLGWHCNYDLCPHC------------------PVCQGT  : 72
RDA5       KNGL-------AQGQYKGWRTNNADCPHC------------------PTCQGT  : 76
RDA8       -------VKPNLFNNPGLNNWPLDHFKCNRYWNES-----------DTYGGVCQAV  : 89
RDA9       Y------LKPQNFNNPGRKTWYLNQAGCFSNWCLT-----------DTFGICMGE  : 92
RDA7       SNPTK--LIPEYFNLSGKKVWPNNDFACHNFWVTSG----------KHGCAACVAS  : 96
RDA15      SNDHK--GYPN-ESVKCATWYMANTVSGFNHRPIG-----------ACYRCAAA  : 95
RdhA2_BAV1 -----------NNPGRKTWYLDWFKCRPWG-----------SPYYCPNCQTV  : 79
RdhA3_BAV1 -----------NGTGRKLYPVDYPKCGPWRGMPPGGIGHIYEAGPGGSNCQVV  : 92
PCEA       -----------IHNQSGKLQWQNDYNKCLGYWPES-----------GGYGGVCVAV  : 80
PCEAc      EN---------PYTEKWHLDSNRCGSFWAYN-----------GSPANCVAV  : 84
PCEAd      EN---------PYTEKWHLDSNRCGSFWAYN-----------GSPSNCVAV  : 84
PCEAb      EN---------PYTEKWHLDSNRCGSFWAYN-----------GSPCSNCVAV  : 84
CPRAd      -----------GYLRWNSDFKKCTEFRTTNEE---------GSSGGTCLKV  : 76
CprAV      -----------GYLRWNSDFKKCTEFRTTNEE---------GSSGGTCLKV  : 76
CprAh      -----------GYLRWNSDFRKCTEFRTTNEE---------GSSGGTCMKV  : 76
CPRAc      -----------GYLRWNSDMKKCAVFRTTNEE---------GSSGGRCMKV  : 76
RDA16      -----------VVKSIRWFQDGKKCLSQRLAYG-----------CSKCQSV  : 75
RDA17      -----------GQRRYNTNLAKCRDGWNLGAG----------PMGCRACISV  : 77
                      g    5  1  c                          c  C
           120            *           140           *           160
```

Figure 6C

```
RDA13      CVE TNMK--AMVHD VEATVGTTG FNG-----ELWNADKAFGYGL------V-P  : 131
RDA        CVE TNTS--AMVHELVETTVSSTGLLNG-----ELWNADKAFGYGL------V-P  : 131
RDA11      CVE VNTK--AMIHEVVESTLSTTGIFNS-----ELWKADVAFGYG---------   : 120
RDA12      CTF TNGA--SMIHDVVEATLAKTSLLNG-----ELWNADKAFGYGL------V-E  : 132
RdhA1_BAV1 CTF VNGA--AMVHDVVEATLATTSMFNE-----ELWKADKTFGYGV------K-S  : 127
RdhA7_BAV1 CVE VDNA--SMIHQVVEGTIATTSLFNG-----EMKQADKFGYGL------T-P  : 132
RDA10      CTF TVNRG--SLVHQLIEGTVANVSLFNT-----YFYKLGEAFGYG-------A-D  : 128
RDA2       CPE AIGD-GSFVHSIVESTVATSPIFNS-----EFTSMEGVLHYGK-------Q    : 134
RdhA4_BAV1 CPE AIPN-GSFIHSLVKATTSTTPLFNG-----EFTQMEKSLHYGK-------Q    : 133
RDA1       CPF GTAG--ASLIHEVVEGTMSVTPVFNS-----EFRSMSETFNYG---------   : 127
RdhA6_BAV1 CPD FNMTN-GSLIHNVVRSTVAATPVFNS-----EFRQMEHTFGYG---------M  : 113
TCEA       CPF FTMSN-NSWVHNLVESTVATTPVFNG-----EFKNMEGAFGYGP------R-Y  : 115
RDA6       CPF TNGD-GSFIHDLVENTVSVTPVFNS-----EFANMEKTMGYG---------   : 112
RdhA5_BAV1 CPE TNGD-GSFIHDLVENTVSTTPIFNS-----EFANMEKTMGYG---------   : 112
RDA3       CPF NSHP--GSFIHDVVEGTVSTTPIFNS-----EFKNMEKTFKYG---------   : 111
RDA4       CPF TIRDDKSFIHELVEISASHTTVFNT-----EFRNMDLNFDYG---------   : 113
RDA5       CPF NSTS--QSFIHDMVEVTTTNIPVFNG-----EFANMERFMEYG---------   : 115
RDA8       CVE SKDDA-SSVHELVKATLAKTTMLNS-----EFVNMDKGFGYGL------KPE  : 132
RDA9       CVF NKLAD--SSIHEVVEPVIANTTLLDG-----EFFNMDKAFGYGC------LPE  : 135
RDA7       CVE SKDIK--SSIHEVVKGVVSQTGIFNG-----EFANMDHAFGYGI------VKD  : 139
RDA15      CVF NKSNE--AWIHEIVEATVSTTPLLNS-----EFANMDTQAGYGE------MSP  : 138
RdhA2_BAV1 CPE NNPNK--AIIENAVXXTAATTPIFNS-----EFSSLDKSFGYAHQRSD---EE  : 125
RdhA3_BAV1 CVE TKTPK--ASIHDVIEPLVSSTSVFNS-----EFTTLDKSFHYGGAFVTPLGEV  : 141
PCEA       CPF TKGNI--WIHDGVEWLIDNTRFLDP-----LMLGMDDALGYG---------A  : 119
PCEAc      CSW NKVET---WNHDVAE-IATQIPLLQD-----AARKFDEWFGYNG---------   : 122
PCEAd      CSW NKVET---WNHDVAE-IATQIPLLQD-----AARKFDEWFGYNG---------   : 122
PCEAb      CSW NKVET---WNHDVAE-VATQIPLLQD-----AARKFDEWFGYNG---------   : 122
CPRAd      CPW NSKED--SWFHKAGVWVGSKGEAAST-----ELKSIDDIFGYGT--------E  : 117
CprAV      CPW NSKED--SWFHKAGVWVGSKGEAAST-----ELKSIDDIFGYGT--------E  : 117
CprAh      CPW NSKED--SWFHKAGVWVGSKGETAST-----ELKSIDDIFGYGT--------E  : 117
CPRAc      CPW NSKED--SWFHEAGLWIGSRGEVASS-----LLKNIDDMFGYGT--------E  : 117
RDA16      CPW-SKPD--TLIHEIGRMVG-QNPAFAP-----ELVKLDDFFYNRY--------P  : 114
RDA17      CPW TKKNT---WVHRFVREVLSHDATGTSQNIAIWAERTLYPKHVQEELNPPNYQG : 130
           C    5         H                                yg
                         *         180           *      200
```

Figure 6D

```
RDA13       PEKWEEWWDKD-YPVLGQDSTIGSYYGGY--------    :159
RDA         AEETSKWWDLS-LPLYGQDGSIGATDGGYK-------    :161
RDA11       HHDAAEWWDLD-LPRYGFDTTMGVRDGGYGK------    :150
RDA12       GDEKEKFWEIG-LPAYGFDTTVGSTVGGY--------    :160
RDhA1_BAV1  GEEKEDWWDLS-LPSMGWDTTSFSKHGGY--------    :155
RDhA7_BAV1  ESEWNNWWDMN-LPAYAFDTTVGVTDGGYKAKGLLQQ    :168
RDA10       AEKAETWWDLS-LPTLGQDSTITAADGGYGK------    :158
RDA2        DKDPASWWNSP-DEWFIYGTHPNLLRQ----------    :160
RDhA4_BAV1  DKDPESWWHEP-NAWHVYGSNPGLLG-----------    :158
RDA1        HKEPESWWDLPLEQIPAYGVNPALLVK ---------    :154
RDhA6_BAV1  KDDLNDWWNQSHKPW----------------------    :128
TCEA        SPSRDEWWASE-NPIRGASVDIF--------------    :137
RDA6        RKDPRDWWN-IDDYTYGINTSY---------------    :133
RDhA5_BAV1  RKDPRDWWN-IDDYTYGINTSY---------------    :133
RDA3        RKNPATWWDEVDDYPYGVDTSY---------------    :133
RDA4        RKDQRDWWK-EEDFPFGIDTSY---------------    :134
RDA5        RKPQWEFWD-IEQPTYGFDTTA---------------    :136
RDA8        DT-IEEWWTN---SFPVNGIHYDNDAYYN--------    :157
RDA9        DQ-WEDWWTLG-EKMPIHGI-----------------    :153
RDA7        QNMWDNFWFEPDKYWPLEGIETNL-------------    :163
RDA15       DEERSTLWTGNMAEWGIHQYGKNEW------------    :163
RDhA2_BAV1  RLN---WWYRDLNTWQYDD-VFGMGTKDPKSWL----    :154
RDhA3_BAV1  NVSPDEWWNRDLKTYPFKGRVMGDG------WA----    :168
PCEA        KRNITEVWDGKINTYGLDADHFRDTVSFRKDRVKKS-    :155
PCEAc       PVNPDERLESGYVQNMVKDFWNNPESIKQ--------    :151
PCEAd       PVNPDERLESGYVQNMVKDFWNNPESIKQ--------    :151
PCEAb       PVNPDERLESGYVQNMVKDFWNNPESIKQ--------    :151
CPRAd       TIEKYKWWLEWPEKYPLKPM-----------------    :137
CprAV       TIEKYKWWLEWPEKYPLKPM-----------------    :137
CprAh       TIEKYKWWLEWPEKYVMK-------------------    :135
CPRAc       TIDKYKWWLEWPELYKIQ-------------------    :135
RDA16       EGHATGEWAPWR-------------------------    :126
RDA17       VYEPPKWIQTNEYVSSFVNTPMGVK------------    :155
                  w
```

ISOLATED REDUCTIVE DEHALOGENASE GENES

FIELD OF THE INVENTION

The invention relates to novel reductive dehalogenase genes encoding reductive dehalogenases that have been isolated from dechlorinating bacteria. The invention also relates to methods of detecting and characterizing reductively dechlorinating populations of bacteria possessing the novel dehalogenase genes of the invention.

BACKGROUND OF THE INVENTION

Vinyl chloride (VC) is a toxic and carcinogenic priority pollutant that threatens drinking water quality in most industrialized countries. Kielhorn J., et al. (2000) *Environ. Health Perspect.* 108:579-588. A major source of environmental VC is due to transformation reactions acting on chlorinated solvents such as tetrachloroethene (PCE) and trichloroethene (TCE), which are abundant groundwater pollutants. Mohn W., et al. (1992) *Microbiol. Rev.* 56:482-507. Additional environmental VC pollution originates from landfills, PVC production facilities and abiotic formation in soils. Due to the extent of the problem, innovative and affordable technologies are needed to restore VC contaminated sites and guarantee drinking water safety.

Bioremediation approaches that rely on the activity of bacterial populations that use chlorinated compounds as growth-supporting electron acceptors (i.e., chlororespiration) have been used previously in the field (see, e.g., Ellis D., et al. (2000) *Environ. Sci. Technol.* 34:2254-2260; Major, D., et al. (2002) *Environ. Sci. Technol.* 36:5106-5116; Lendvay J., et al. (2003) *Environ. Sci. Technol.* 37:1422-1431). Bacterial populations useful in bioremediation include bacteria capable of reductive dechlorination and detoxification of VC to ethene. Such bacterial populations include members of the family *Dehalococcoides*, a deeply branching group on the bacterial tree most closely affiliated with the Chloroflexi. Cupples A., et al. (2003) *Appl. Environ. Micobiol.* 69:953-959. To facilitate the identification of bacterial populations responsible for dechlorination and detoxification of VC, 16S rRNA gene-based PCR approaches have been designed to detect and quantify members of *Dehalococcoides*. Such approaches have been helpful for assessing VC-contaminated sites, monitoring bioremediation efforts, and establishing cause-effect relationships between the presence of chlorinated compounds and the growth of specific strains of dechlorinating bacteria. Lendvay J., et al. (2003) *Environ. Sci. Technol.* 37:1422-1431.

Although 16S rRNA gene-based PCR approaches have been developed to detect and quantify members of *Dehalococcoides*, such approaches are limited in their applicability as *Dehalococcoides* strains with different dechlorination activities share similar or identical 16S rRNA gene sequences. He, J. et al. (2003) *Nature* 424:62-65. Examples of *Dehalococcoides* strains which demonstrate substantial similarities among 16S rRNA gene sequences, but distinct dechlorination activities include *Dehalococcoides* sp. strain CBDB1, which dechlorinates trichlorobenzenes, pentachlorobenzene and some polychlorinated dibenzodioxin congeners but failed to dechlorinate PCE and TCE (Adrian, et al. (2000) *Nature* 408:580-583), *Dehalococcoides ethenogenes* 195 and *Dehalococcoides* sp. and *Dehalococcoides* sp. strain FL2, which grow with polychlorinated ethenes as electron acceptors but cannot grow with VC, and *Dehalococcoides* sp. strain BAV1 which respires all DCE isomers and VC (He, J. et al. (2003) *Nature* 424:62-65). Despite their metabolic differences, these strains share 16S rRNA gene sequences with more than 99.9% similarity (based on the analysis of 1,296 aligned positions). He, J. et al. (2003) *Appl. Environ. Microbiol.* 65:485-495.

As a result of the high degree of identity among the 16S rRNA gene sequences of various *Dehalococcoides* populations, the identification of bacteria having different dechlorinating activities is difficult. There is, therefore, a need in the art for an improved means of identifying and characterizing reductively dechlorinating populations of bacteria. One such approach is to identify genes associated with the dechlorination of particular halogenated compounds, particularly genes encoding for reductive dehalogenases (RDases) capable of reductive dehalogenation of VC.

Gene sequences encoding for reductive dehalogenases involved in the partial reductive dechlorination of PCE and chlorinated aromatic compounds have been identified (see e.g., Magnuson, J., et al. (2000) *Appl. Environ. Microbiol.* 66:51441-5147). Functional genes involved in complete reduction of VC, however, have not been found. Alignment of known reductive dehalogenase amino acid sequences revealed low sequence identity (27 to 32%); although conserved stretches have been identified, e.g., a twin diarginine (RR) motif near the amino-terminus and two iron-sulfur cluster binding motifs near the C-terminus. Additionally, each of the identified RDase genes is associated with a B gene that encodes a hydrophobic protein with transmembrane helices believed to anchor the RDase to the membrane. Magnuson, J., et al. (2000) *Appl. Environ Microbiol.* 66:51441-5147. In *Dehalococcoides*, *Sulfurospirillum* (formerly *Dehalospirillum*), *Dehalobacter* and *Desulfitobacterium*, the B gene is located downstream of the PCE/TCE RDase genes. See e.g., Magnuson, J., et al. (2000) *Appl. Environ. Microbiol.* 66:51441-5147; Maillard, J., et al. (2003) *Appl. Environ. Microbiol.* 69:4628-4638; Suyama, A., et al. (2002) *J. Bateriaol.* 184:3419-3425. In cprA operons (ortho chlorophenol RDases) of *Desulfitobacterium* species an opposite arrangement was observed. Van de Pas, B., et al. (2003) *J. Biol. Chem.* 52:299-312.

Although gene sequences encoding reductive dehalogenases involved in the partial reductive dechlorination of PCE and chlorinated aromatic compounds have been identified, genes encoding enzymes capable of reductive dechlorination of vinyl chloride to ethene, have not been identified. Hence, there is a need in the art to identify functional genes associated with VC reductive dechlorination and in particular to identify and isolate reductive dehalogenase genes from dechlorinating bacteria and in particular those of the family *Dehalococcoides*. Additionally, there is a need in the art for a method of that identifies reductively dechlorinating populations of bacteria which overcomes the limitations of the identification methods of the prior art, and facilitate the monitoring of bioremediation by dechlorinating bacteria.

SUMMARY OF THE INVENTION

The present invention provides novel reductive dehalogenase genes isolated from dechlorinating bacteria and encoding for reductive dehalogenase enzymes. The deduced amino acid sequences of the presently identified dehalogenase enzymes indicates that they are capable of the reductive dehalogenation of halogenated substrates and in particular the reduction of vinyl chloride to ethene.

In certain embodiments, the invention provides for methods of identifying and isolating bacterial target DNA from dechlorinating bacteria of interest, such as *Dehalococcoides* populations.

In additional embodiments, the invention provides gene primer pairs and probes useful for quantification of dechlorinating bacteria using analytical techniques such as, for example and without limitation, hybridization, PCR and Real-Time PCR technology. The components provided and the methods in which they are employed are useful in bioremediation processes mediated by dechlorinating bacteria.

In still another embodiment, the invention provides for an isolated polynucleotide encoding a reductive dehalogenase comprising a polynucleotide sequence having at least 85% and preferably at least 90% and more preferably at least 95% and still more preferably 99% sequence identity over the length of the entire reference sequence to a polynucleotide consisting of a sequence selected from the group consisting of SEQ ID NO: 1-8.

In other embodiments, the invention provides a recombinant expression vector comprising any one of the aforementioned isolated polynucleotides operably linked to a regulatory sequence, and a cell, or organism comprising the recombinant gene sequence.

In another embodiment, the invention provides a vector comprising any one of the aforementioned isolated polynucleotides.

In still another embodiment, the invention provides an isolated polynucleotide encoding an enzyme that reductively dechlorinates vinyl chloride. In a preferred embodiment, the invention provides an isolated polynucleotide encoding a reductive dehalogenase.

In yet another embodiment, the invention provides an isolated polynucleotide encoding an enzyme that reductively dechlorinates vinyl chloride wherein the polynucleotide is isolated from dechlorinating bacteria, such as for example, *Dehalococcoides* sp. strain BAV1.

In another embodiment, the present invention provides a method of identifying a polynucleotide encoding a reductive dehalogenase in a sample, comprising: contacting the sample with (i) a first oligonucleotide primer comprising a portion of the polynucleotide of claim 1; and (ii) a second oligonucleotide primer comprising a portion of the polynucleotide of claim 1; and performing PCR on the sample, wherein the presence of an amplification product indicates the presence of a polynucleotide encoding a reductive dehalogenase in the sample.

In another embodiment the invention provides a method of quantifying the amount of dechlorinating bacteria present in a sample comprising, (a) contacting the sample with (i) a probe comprising a portion of any one of the sequences selected from the group consisting of SEQ ID NO: 1-8; (ii) a first primer comprising a portion of any one of the sequences selected from the group consisting of SEQ ID NO: 9-15; and (iii) a second primer comprising a portion of any one of the sequences selected from the group consisting of SEQ ID NO: 16-22; and (b) performing Real-Time PCR on the sample to quantify the amount of dechlorinating bacteria present in the sample.

In another embodiment, the invention provides a method of detecting the presence of a dechlorinating bacteria in a sample comprising, (a) contacting the sample with (i) a first primer comprising a portion of any one of the sequences selected from the group consisting of SEQ ID NO: 9-15; and (ii) a second primer comprising a portion of a sequence selected from the group consisting of SEQ ID NO: 16-22; and (b) performing PCR on the sample, wherein the presence of amplification products confirms the presence of the dechlorinating bacteria.

In another embodiment, the invention provides a method for identifying a dechlorinating bacterial organism comprising the steps of (a) contacting a probe with a bacterial cell extract, the contact effecting the hybridization with a nucleic acid derived from the bacterial cell extract, wherein the probe comprises the polynucleotide claim 1, or a fragment thereof, and, (b) determining that the probe has hybridized to the nucleic acid derived from the bacterial cell extract.

BRIEF DESCRIPTION OF THE DRAWINGS

FIGS. 5A-5D are an alignment matrix corresponding to the alignment of the deduced amino acid sequences from *Dehalococcoides* sp. strain BAV1 reductive dehalogenase genes, including bvcA, of the present invention and other known reductive dehalogenases isolated from *Dehalococcoides ethenogenes* strain 195, *Dehalospirllum multivorans* (PceA), *Desulfitobacterium* sp. Y51 (PceAb), *Dehalobacter restrictus* (PceAc), *Desulfitobacterium frappieri* (PceAd), *Desulfitobacterium dehalogenans* (CprAd, CprAc), *Desulfitobacterium hafniense* (CprAh) and *Desulfitobacterium* sp. Viet-1 (CprAV).

FIGS. 6A-6D show the alignment of the amino acid sequences deduced from the BvcA gene of the present invention and other known reductive dehalogenases isolated from *D. ethenogenes* strain 195 and *Dehalococcoides* sp. strain BAV1. RDA (1-17) correspond to the deduced amino acid sequences of *D. ethenogenes* strain 195 reductive dehalogenases (Villemur et. al. (2002) *J. Can. Microbiol.* 48:697-706), TceA corresponds to *D. ethenogenes* strain 195 trichlorethene dehalogenase (AF0228507-2), PceA corresponds to tetrachloroethene dehalogenase of *Dehalospirllum multivorans* (AF22812.1), PceAb corresponds to tetrachloroethene dehalogenase of *Desulfitobacterium* sp. Y51. (21623559), PceAc corresponds to tetrachloroethene dehalogenase of *Dehalobacter restrictus* (AJ439607.1), PceAd corresponds to tetrachloroethene dehalogenase of *Desulfitobacterium frappieri* (AJ439608.1), CprAd corresponds to o-chlorophenol dehalogenase precursor of *Desulfitobacterium dehalogenans* (AF115542-3), CprAc corresponds to o-chlorophenol dehalogenase of *Desulfitobacterium chlororespirans* (AF204275.2), CprAh corresponds to o-chlorophenol dehalogenase of *Desulfitobacterium hafniense* (AF4031828), CprAV corresponds to o-chlorophenol reductive dehalogenase of *Desulfitobacterium* sp. Viet-1 (AF259791.1). The amino acid sequences of the reductive dehalogenases in FIGS. 6A-6D are included in the sequence listing as follows: RDA13 is SEQ ID NO: 38; RDA is SEQ ID NO: 39; RDA11 is SEQ ID NO: 40; RDA12 is SEQ ID NO: 41; RDA10 is SEQ ID NO: 42; RDA2 is SEQ ID NO: 43; RDA1 is SEQ ID NO: 44; TCEA is SEQ ID NO: 45; RDA6 is SEQ ID NO: 46; RDA3 is SEQ ID NO: 47; RDA4 is SEQ ID NO: 48; RDAS is SEQ ID NO: 49; RDA8 is SEQ ID NO: 50; RDA9 is SEQ ID NO: 51; RDA7 is SEQ ID NO: 52; RDA15 is SEQ ID NO: 53; PCEA is SEQ ID NO: 54; PCEAc is SEQ ID NO: 55; PCEAd is SEQ ID NO: 56; PCEAb is SEQ ID NO: 57; CPRAd is SEQ ID NO: 58; CprAV is SEQ ID NO: 59; CprAh is SEQ ID NO: 60; CPRAc is SEQ ID NO: 61; RDA16 is SEQ ID NO: 62; RDA17 is SEQ ID NO: 63.

DETAILED DESCRIPTION OF THE INVENTION

Figure 1:
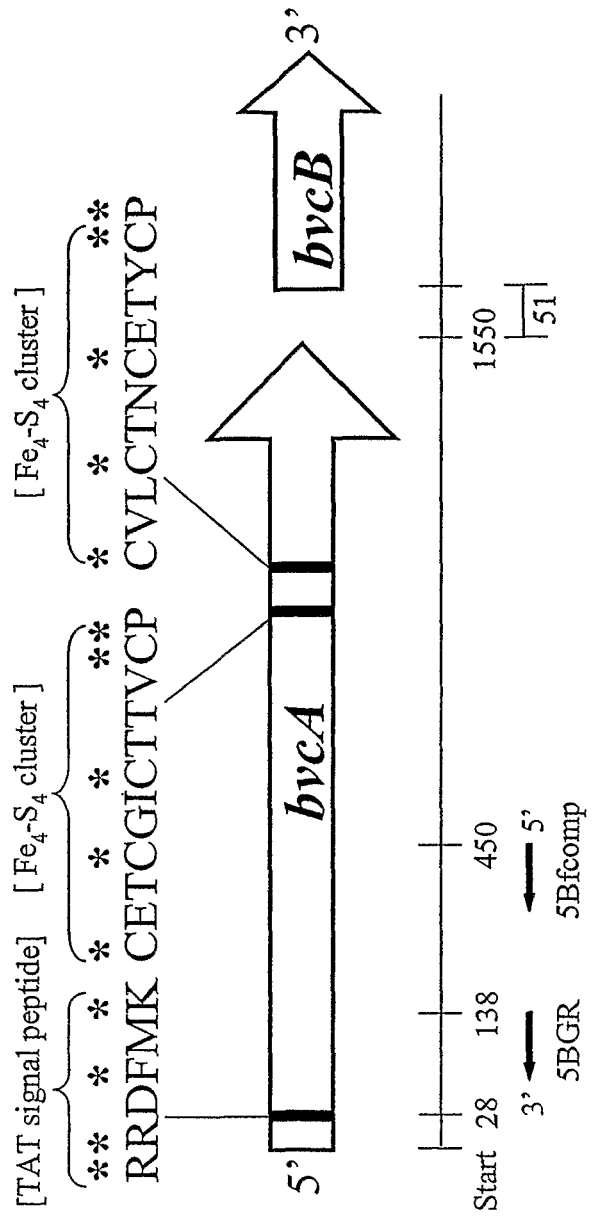
FIG. 1 shows a schematic of the bvcA gene and its corresponding B gene showing conserved features shared with other known reductive dehalogenase genes and their associated B genes. Conserved dehalogenase features are labeled with an asterisk.

The present invention is directed to novel reductive dehalogenase genes encoding for reductive dehalogenases which are capable of dehalogenating organic compounds. The genes and proteins they encode may be useful in the bioremediation of pollutants. In particular embodiments, the invention provides the complete sequence of a novel vinyl chloride dehalogenase gene (bvcA) having the polynucleotide sequence of SEQ ID NO: 1. The novel vinyl chloride dehalogenase gene encodes a reductive dehalogenase that is capable of the complete reduction of vinyl chloride to ethene.

The present invention further provides for a method of identifying dechlorinating bacterial populations capable of facilitating the reductive dechlorination of organic compounds and in particular the identification of vinyl chloride respiring dechlorinating bacterial populations. Such methods include, but are not limited to, the identification of dechlorinating bacterial populations via the identification of reductive dehalogenase genes, using such methods as hybridization, PCR and Real-Time PCR. Moreover, such methods may be used to assess and monitor dechlorinating bacterial populations at sites contaminated with halogenated compounds and which are amenable to bioremediation using dechlorinating bacteria.

DEFINITIONS AND ABBREVIATIONS

The term reductive dehalogenase is abbreviated "RDase."

The term Real-Time PCR is abbreviated as "RTm PCR" and as used herein means a method for simultaneous amplification, detection, and quantification of a target polynucleotide using double dye-labeled fluorogenic oligodeoxyribonucleotide probes during PCR.

As used herein, the terms "PCE," "perchloroethylene," "tetrachloroethylene," and "tetrachloroethene" are synonymous and refer to $Cl_2C=C\,Cl_2$ As used herein, "TCE," "trichloroethylene," and "trichloroethene" are synonymous and refer to $Cl_2C=CH-Cl$.

As used herein, "DCE," "dichloroethylene," and "dichloroethene" are synonymous and refer to $Cl-HC=CH-Cl$.

As used herein, "VC, "vinyl chloride," and "chloroethene" are synonymous and refer to $H_2C=CH-Cl$.

As used herein, "ethylene" and "ethene" are synonymous and refer to $H_2C=CH_2$.

As used herein, the term "chloroethenes" refers to PCE, TCE, DCE, VC, and mixtures thereof.

"Reductive dehalogenase enzyme" refers to an enzyme system that is capable of dehalogenating a halogenated straight chain or ring containing organic compound, that contains at least one halogen atom. Examples of halogenated organic compounds that may de-halogenated by a reductive dehalogenase include, but not limited to, PCE, TCE, DCEs (cis-DCE, trans-DCE, 1,1-DCE)_and VC.

"Dechlorinating bacteria" refers to a bacterial species or organism population that has the ability to remove at least one chlorine atom from a chlorinated organic compound. Examples of dechlorinating bacteria include, but are not limited to *Dehalococcoides* spp, *Dehalobacter restrictus*, *Sulfurospirillum multivorans*, *Desulfitobacterium dehalogenans*, *Desulfuromonas chloroethenica*, and *Desulfuromonas michiganensis*.

As referred to herein, "sequence similarity" means the extent to which nucleotide or protein sequences are related. The extent of similarity between two sequences can be based on percent sequence identity and/or conservation. With regard to proteins, sequence identity is a comparison of exact amino acid matches, whereas sequence similarity refers to amino acids at a position that have the same physical-chemical properties (i.e. charge, hydrophobicity). Amino acids other than those indicated as conserved may differ in a protein or enzyme so that the percent protein or amino acid sequence similarity between any two proteins of similar function may vary. Preferably, the sequence identity is at least 30%, preferably at least 50%, more preferably at least 70%, even more preferably 80%, and most preferably at least 90%, as determined according to an alignment scheme.

"Sequence alignment" means the process of lining up two or more sequences to achieve maximal levels of sequence identity (and, in the case of amino acid sequences, conservation), e.g., for the purpose of assessing the degree of sequence similarity. Methods for aligning sequences and assessing similarity and/or identity are well known in the art. Such methods include for example, the MEGALIGN software Clustal Method, wherein similarity is based on the MEGALIGN Clustal algorithm, ClustalW and ClustalX (Thompson, J., et al. (1997) *Nucleic Acid Res.* 25:4876-4882) as well as BLASTN, BLASTP, and FASTA (Pearson et al. (1988) *Proc Natl. Acad. Sci. USA*. 85:2444-2448). When using these programs, the preferred settings are those that result in the highest sequence similarity.

Molecular Biology

In accordance with the present invention there may be employed conventional molecular biology, microbiology, and recombinant DNA techniques within the skill of the art. The general genetic engineering tools and techniques discussed herein, including transformation and expression, the use of host cells, vectors, expression systems, etc., are well known in the art. See, e.g., Sambrook, Fritsch & Maniatis, Molecular Cloning: A Laboratory Manual, Third Edition (2001) Cold Spring Harbor Laboratory Press, Cold Spring Harbor, N.Y. (herein "Sambrook et al. 2001"); DNA Cloning: A Practical Approach, Volumes I and II, Second Edition (D. N. Glover ed. 1995); B. Perbal, A Practical Guide To Molecular Cloning (1984); F. M. Ausubel et al. (eds.), Current Protocols in Molecular Biology, John Wiley & Sons, Inc. (1994).

The term "host cell" means any cell of any organism that is selected, modified, transformed, grown, used, or manipulated in any way, for the production of a substance by the cell, for example the expression by the cell of a gene in this cell, a DNA or RNA sequence, a protein or an enzyme.

A "polynucleotide" or "nucleotide sequence" is a series of nucleotide bases (also called "nucleotides") in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotides, and both sense and antisense polynucleotides (although only sense stands are being represented herein). This includes single- and double-stranded molecules, i.e., DNA-DNA, DNA-RNA and RNA-RNA hybrids, as well as "protein nucleic acids" (PNAs) formed by conjugating bases to an amino acid backbone. This also includes nucleic acids containing modified bases, for example thio-uracil, thio-guanine and fluoro-uracil.

Polynucleotides may be flanked by natural regulatory sequences, or may be associated with heterologous sequences, including promoters, enhancers, response elements, signal sequences, polyadenylation sequences, introns, 5'- and 3'-non-coding regions, and the like, and may be modified by many means known in the art.

The term "gene", means a DNA sequence that codes for or corresponds to a particular sequence of amino acids which comprise all or part of one or more proteins or enzymes, and may or may not include regulatory DNA sequences, such as promoter sequences, which determine, for example, the conditions under which the gene is expressed.

A "coding sequence" or a sequence "encoding" a polypeptide, protein or enzyme is a nucleotide sequence that, when expressed, results in the production of that polypeptide, protein or enzyme, i.e., the nucleotide sequence encodes an amino acid sequence for that polypeptide, protein or enzyme. Preferably, the coding sequence is a double-stranded DNA sequence that is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining this invention, the promoter sequence is bounded at its 3' terminus by the transcription initiation site and extends upstream (5' direction) to include the minimum number of bases or elements necessary to initiate transcription at levels detectable above background. As described above, promoter DNA is a DNA sequence which initiates, regulates, or otherwise mediates or controls the expression of the coding DNA. A promoter may be "inducible", meaning that it is influenced by the presence or amount of another compound (an "inducer"). For example, an inducible promoter includes those that initiate or increase the expression of a downstream coding sequence in the presence of a particular inducer compound. A "leaky" inducible promoter is a promoter that provides a high expression level in the presence of an inducer compound and a comparatively very low expression level, and at minimum a detectable expression level, in the absence of the inducer.

The terms "express" and "expression" mean allowing or causing the information in a gene or DNA fragment to become manifest, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein or enzyme, may also be the to be "expressed" by the cell. A polynucleotide or polypeptide is expressed recombinantly, for example, when it is expressed or produced in a foreign host cell under the control of a foreign or native promoter, or in a native host cell under the control of a foreign promoter.

The term "transformation" means the introduction of a "foreign" (i.e. extrinsic or extracellular) gene, DNA or RNA sequence to a host cell, so that the host cell will express the introduced gene or DNA fragment to produce a desired substance, typically a protein or enzyme coded by the introduced gene or sequence. The introduced gene or sequence, which may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g., a foreign gene) can be introduced into a host cell, so as to transform the host and promote expression (e.g., transcription and translation) of the introduced sequence.

A common type of vector is a "plasmid", which generally is a self-replicating molecule of double-stranded DNA. A plasmid can readily accept additional (foreign) DNA and which can readily be introduced into a suitable host cell. A plasmid vector often contains coding DNA and promoter DNA and has one or more restriction sites suitable for inserting foreign DNA. Promoter DNA and coding DNA may be from the same gene or from different genes, and may be from the same or different organisms. A large number of vectors, including plasmid vectors, have been described for replication and/or expression in a variety of eukaryotic and prokaryotic hosts. Non-limiting examples include pKK plasmids (Clontech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression vectors. Routine experimentation in biotechnology can be used to determine which vectors are best suited for used with the present invention. In general, the choice of vector depends on the size of the polynucleotide sequence and the host cells to be used.

The term "expression system" means a host cell and compatible vector under suitable conditions, e.g. for the expression of a protein coded for by foreign DNA carried by the vector and introduced to the host cell. Common expression systems include bacteria (e.g., *E. coli* and *B. subtilis*) or yeast (e.g., *S. cerevisiae*) host cells and plasmid vectors, and insect host cells and Baculovirus vectors. As used herein, a "facile expression system" means any expression system that is foreign or heterologous to a selected polynucleotide or polypeptide, and which employs host cells that can be grown or maintained more advantageously than cells that are native or heterologous to the selected polynucleotide or polypeptide, or which can produce the polypeptide more efficiently or in higher yield. For example, the use of robust prokaryotic cells to express a protein of eukaryotic origin would be a facile expression system. Preferred facile expression systems include *E. coli, B. subtilis,* and *S. cerevisiae,* and reductively dechlorinating populations that are easy to cultivate (e.g., *Anaeromyxobacter dehaloganans* strains and *Desulfitobacterium* species) as host cells and for any suitable vector.

"Sequence-conservative variants" of a polynucleotide sequence are those in which a change of one or more nucleotides in a given codon position results in no alteration in the amino acid encoded at that position.

"Isolation" or "purification" of a polypeptide, protein or enzyme refers to the derivation of the polypeptide by removing it from its original environment (for example, from its natural environment if it is naturally occurring, or form from the host cell if it is produced by recombinant DNA methods). Methods for polypeptide purification are well known in the art, including, without limitation, preparative disc-gel electrophoresis, isoelectric focusing, HPLC, reversed-phase HPLC, gel filtration, ion exchange, hydrophobic interaction, affinity, and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against the protein or against peptides derived therefrom can be used as purification reagents. Other purification methods are possible. A purified polynucleotide or polypeptide may contain less than about 50%, preferably less than about 75%, and most preferably less than about 90%, of the cellular components with which it was originally associated. A "substantially pure" enzyme indicates the highest degree of purity that can be achieved using conventional purification techniques known in the art.

Polynucleotides are "hybridizable" to each other when at least one strand of one polynucleotide can anneal to another polynucleotide under defined stringency conditions. Stringency of hybridization is determined, e.g., by the temperature at which hybridization and/or washing is performed, and b) the ionic strength and polarity (e.g., formamide) of the hybridization and washing solutions, as well as other parameters. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarity between the hybridizing sequences. (1×SSC is 0.15 M NaCl, 0.015 M Na citrate.) Polynucleotides that "hybridize" to the polynucleotides herein may be of any length. In one embodiment, such polynucleotides are at least 10, preferably at least 15 and most preferably at least 20 nucleotides long. In another embodiment, polynucleotides that hybridize are of about the same length. In another embodiment, polynucleotides that hybridize include those which anneal under suitable stringency conditions and which encode polypeptides, proteins or enzymes having the same function, such as the ability to catalyze an oxidation, oxygenase, or coupling reaction.

Identification of RDase Genes

In certain embodiments, the present invention provides polynucleotide fragments which may be useful as primers and probes for the identification of genes encoding reductive dehalogenases (RDases). In one embodiment, the invention provides polynucleotide fragments useful for the isolation of RDase genes by aligning conserved regions of full-length protein and DNA sequences of TceA and RDases. Examples of such primers are shown in Table 1, below.

TABLE 1

Polynucleotide fragments

| Primer | Nucleotide Sequence | Target |
| --- | --- | --- |
| RRF2 | 5'-SHMGBMGWGATTTYATGAARR-3' (SEQ ID NO: 34) | RRXFXK motif |
| B1R | 5'-CHADHAGCCAYTCRTACCA-3' (SEQ ID NO: 35) | WYEW motif |

$^a$ Abbreviations of degenerate nucleotides: R = A/G; K = G/T; M = A/C; S = C/G; W = A/T; Y = C/T; B = C/G/T; D = A/G/T; V = A/C/G; H = A/C/T.

The invention also provides PCR primer pairs and probes useful in the identification of RDase genes, as well as a number of polynucleotide fragments encoding at least a portion of several RDases. The PCR primer pairs, probes and polynucleotide fragments of the present invention may be used to isolate cDNAs and genes encoding homologous proteins from the same or other dechlorinating bacteria species.

Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., PCR, ligase chain reaction).

For example, genes encoding other RDases, either as cDNAs or genomic DNAs, could be isolated directly by using all or a portion of the instant polynucleotide fragments as DNA hybridization probes to screen libraries from any desired dechlorinating bacterial population employing methodology well known to those skilled in the art. Specific oligonucleotide probes based upon the instant nucleic acid sequences can be designed and synthesized by methods known in the art (see, e.g., Sambrook, et al. 2001). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant polynucleotide fragments may be used in PCR protocols to amplify longer nucleic acid fragments encoding homologous genes from DNA or RNA. The PCR may also be performed on a library of cloned nucleic acid fragments to identify nucleotide sequences encoding bacterial reductive dehalogenases.

Alternatively, the second primer sequence may be based upon sequences derived from the cloning vector. For example, the skilled artisan can follow the RACE protocol (Frohman et al. (1988) *Proc. Natl. Acad. Sci.* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems, specific 3' or 5' cDNA fragments can be isolated (Ohara et al. (1989) *Proc. Natl. Acad. Sci.* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of about at least about 30 contiguous nucleotides derived from a nucleotide sequence selected from the group consisting of SEQ ID NO: 1-8 and the complement of such nucleotide sequences may be used in such methods to obtain a nucleic acid fragment encoding a substantial portion of an amino acid sequence of a polypeptide.

Identifications Use and Expression of RDase Polypeptides

In certain additional embodiments, the present invention provides a method of obtaining a polynucleotide fragment encoding a RDase polypeptide, preferably a substantial portion of a RDase polypeptide, comprising the steps of: (i) synthesizing a pair of oligonucleotide primers comprising, wherein each oligonucleotide primer comprises preferably at least about 10, more preferably at least about 15, and still more preferably at least about 25 contiguous nucleotides derived from a nucleotide sequence selected from the group consisting of SEQ ID NO: 1-8; and (ii) amplifying a polynucleotide fragment (preferably a cDNA inserted in a cloning vector) using the oligonucleotide primer pair. The amplified polynucleotide fragment preferably will encode a portion of a RDase polypeptide that occurs between the two primers.

In one embodiment, the availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (see e.g., Sambrook et al. 2001).

In another embodiment, this invention concerns viruses and host cells comprising either the recombinant expression vectors as described herein or an any one of the isolated polynucleotides of the present invention described herein. Examples of host cells which can be used to practice the present invention include, but are not limited to, yeast, bacteria and insect.

Plasmid vectors comprising the instant isolated polynucleotide may be constructed. The choice of plasmid vector is dependent upon the method that will be used to transform a host organism, e.g., yeast, bacterial cell or insect. The skilled artisan is well aware of the genetic elements that must be present on the plasmid vector in order to successfully transform, select and propagate host cells containing the recombinant expression vector. The skilled artisan will also recognize that different independent transformation events will result in different levels and patterns of expression (Jones et al. (1985) *EMBO J* 4:2411-2418; De Almeida et al. (1989). *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

Genetic Mapping

The isolated polynucleotides of the present invention may be used as probes for the genetic and physical mapping of the genes they are a part of, and may further be used as markers for traits linked to those genes. Such information may be useful in the art to identify and develop strains of dechlorinating bacteria capable of reducing vinyl and other chloroorganic contaminants. For example, the instant polynucleotide fragments may be used as probes to detect restriction fragment length polymorphisms (RFLPs) that identify bacterial populations with the dechlorinating activity of interest. Southern blots (see, e.g., Sambrook, et al. 2001) of restriction-digested bacterial genomic DNA may be probed with the polynucleotide fragments of the instant invention. The resulting banding patterns may then be subjected to genetic analyses using computer programs such as MapMaker (Lander et al. (1987) *Genomics* 1:174-181) to construct a genetic map.

The isolated polynucleotide fragments may also be used to probe Southern blots containing restriction endonuclease-treated genomic DNAs of a set of individuals representing parent and progeny of a defined genetic cross. Segregation of the DNA polymorphisms is noted and used to calculate the position of the instant polynucleotide sequence in the genetic map previously obtained using this population (Botstein et al. (1980) *Am. J. Hum. Genet.* 32:314-331).

Additionally, the isolated polynucleotides of the present invention may be used in a variety of polynucleotide amplification-based methods of genetic and physical mapping. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Polynucleotide Res.* 18:3671), Radiation Hybrid Mapping (Walter et al. (1997) *Nat. Genet.* 7:22-28) and Happy Mapping (Dear and Cook (1989) *Polynucleotide Res.* 17:6795-6807). For these methods, the sequence of a polynucleotide fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant polynucleotide sequence. This, however, is generally not necessary for mapping methods.

Hybridization Techniques for the Detection of Dechlorinating Bacteria

In another embodiment, the invention provides a method of detecting dechlorinating bacteria using the polynucleotides disclosed herein as hybridization probes. The probe length can vary from 5 bases to thousands of bases. Preferably however, the probe is at least 10, more preferably at least 15 and most preferably at least 20 nucleotides in length. Probes may also be, for example, about 100, 200, 300, 400, or 500 nucleotides in length. Only part of the probe molecule need be complementary to the nucleic acid sequence to be detected and the complementary portion need not be identical. Hence, all or part of the aforementioned lengths may be complementary to the polynucleotide sequence to be detected. The probe may be RNA or DNA or a synthetic nucleic acid. In each instance a probe will contain a sequence sufficiently complementary to the nucleic acid from the dechlorinating bacteria to be detected, and that will permit hybridization between the probe and the subject DNA.

In certain embodiments the probe is a polynucleotide that is substantially complementary to a fragment or the entire the polynucleotide sequence of a gene encoding a RDase. In preferred embodiment, the probe may be selected from a fragment or the an entire polynucleotide selected from the group consisting of SEQ ID NO: 1-8. More preferably, the probe is selected from a fragment or the entire polynucleotide of SEQ ID NO: 1.

Hybridization methods are well known in the art (see, e.g., Sambrook, et al. 2001). Typically, the probe and sample are mixed under conditions that permit nucleic acid hybridization. This involves contacting the probe and sample in the presence of an inorganic or organic salt under the proper concentration and temperature conditions. The probe and sample nucleic acids must be in contact for a sufficient time that any possible hybridization between the probe and sample nucleic acid may occur. The concentration of probe or target in the mixture will determine the time necessary for hybridization to occur. The higher the probe or target concentration, the shorter the hybridization incubation time needed.

In certain embodiments, hybridization assays may be conducted directly on bacterial lysates, without the need to extract the nucleic acids. This eliminates several steps from the sample-handling process and speeds up the assay. To perform such assays on crude cell lysates, a chaotropic agent is typically added to the cell lysates prepared as described above. The chaotropic agent stabilizes nucleic acids by inhibiting nuclease activity. Furthermore, the chaotropic agent allows sensitive and stringent hybridization of short oligonucleotide probes to RNA at room temperature (Van Ness and Chen (1991) *Nucl. Acids Res.* 19:5143-5151). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution comprises about 30-50% v/v formamide, about 0.15 to 1 M sodium chloride, about 0.05 to 0.1 M buffer, such as sodium citrate, Tris-HCl, PIPES or HEPES (pH range about 6-9), about 0.05 to 0.2% detergent, such as sodium dodecylsulfate, and between 0.5-20 mM EDTA, FICOLL™ (Amersham Biosciences, Piscataway, N.J.) (about 300-500 kDa), polyvinylpyrrolidone (about 250-500 kDa), and serum albumin. Also included in the typical hybridization solution, will be from about 0.1 to 5 mg/ml, unlabeled carrier nucleic acids, e.g., fragmented calf thymus or salmon sperm DNA, or yeast RNA, and optionally from about 0.5 to 2% wt/vol glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the nucleic acid to be detected, e.g., nucleic acid encoding for a reductive dehalogenase. Preferred are those probes are those described above. Probes particularly useful in the present embodiment are those polynucleotides which are substantially complementary to a fragment or the entire the polynucleotide sequence of a gene encoding a RDase, and in particular to those which are substantially complementary to any one of the sequences of SEQ ID NO: 1-8.

The sandwich assay may be encompassed in an assay kit. A kit may include a first component for the collection of samples from soil or groundwater, such as vials for containment, and buffers for the disbursement and lysis of the sample. A second component may include media in either dry or liquid form for the hybridization of target and probe polynucleotides, as well as for the removal of undesirable and nonduplexed forms by washing. A third component includes a solid support (dipstick) upon which is fixed or to which is conjugated unlabeled nucleic acid probe(s) that is (are) complementary to a part of a nucleic acid encoding for a reductive dehalogenase of the species of bacteria being tested.

PCR Based Detection of Dechlorinating Bacteria

In an another embodiment, the polynucleotides of the present invention may be used as primers in primer directed nucleic acid amplification, i.e., PCR, to detect the presence of the target gene(s) in the dechlorinating wild type bacteria. Methods of PCR primer design are well known in the art (see, e.g., Sambrook, et al. 2001; Hemdon, Va.; and Rychlik, W. (1993) In White, B. A. (ed.), Methods in Molecular Biology, Vol. 15, pp 31-39, PCR Protocols: Current Methods and Applications. Humania Press, Inc., Totowa, N.J., see also, U.S. Pat. Nos. 4,683,195; 4,683,2020; 4,965,188; and 4,800, 159, which are hereby incorporated by reference).

Typically, detection of dechlorinating bacteria using PCR involves the amplification of DNA or cDNA obtained from a sample suspected of having dechlorinating activity. The isolated DNA or cDNA (from mRNA) is amplified using a pair of oligonucleotide primers having regions complementary to only one of the stands in the target. A primer refers to an oligonucleotide that can be extended with a DNA polymerase using monodeoxyribonucleoside triphosphates and a nucleic acid that is used as a template. This primer preferably has a 3' hydroxyl group on an end that is facing the 5' end of the template nucleic acid when it is hybridized with the template.

A set of primers refers to a combination or mixture of at least a first (forward) and a second (reverse) primer. The first primer can be extended using the template nucleic acid while forming an extension product in such a way that the second primer can hybridize with this extension product in a region of the extension product that lies in the 3' direction of the extendable end of the first primer. The extendable end of the second primer points in the 5' direction of the extension product of the first primer. Examples of primers that are suitable for performing the polymerase chain reaction (PCR) and that meet this definition are described in European Patent Application No. 0201184, which is hereby incorporated by reference. Typical amplicons range in size from 25 bp to 2000 bp (see, e.g., U.S. Pat. No. 6,518,025). Larger sized amplicons can be obtained, typically using specialized conditions or modified polymerases.

The primers of the present invention are designed to be specific to regions of the bvcA genes identified herein. Useful primers include, but are not limited to, those having the polynucleotide sequence of any one of SEQ ID NO: 9-22. In a preferred embodiment the first primer is the polynucleotide of SEQ ID NO.: 14 and the second primer is the polynucleotide of SEQ ID NO: 21.

Following amplification, the products of PCR may be detected using any one of a variety of PCR detection methods are known in the art including standard non-denaturing gel electrophoresis (e.g., acrylamide or agarose), denaturing gradient gel electrophoresis, and temperature gradient gel electrophoresis. Standard non-denaturing gel electrophoresis is the simplest and quickest method of PCR detection, but may not be suitable for all applications.

Real Time PCR Based Detection of Dechlorinating Bacteria

In yet another embodiment, the invention provides a method of detecting dechlorinating bacteria using Real-Time PCR ("RTm PCR"). RTm PCR is a further enhancement to the standard PCR, described above. RTm-PCR allows contemporaneous quantification of a sample of interest, for example a bacteria population having a polynucleotide sequence of interest.

In RTm PCR, a fluorogenically labeled oligonucleotide probe is used in addition to the primer sets which are employed in standard PCR. The probe, in RTm PCR anneals to a sequence on the target DNA found between a first (forward, 5' primer) and second (reverse, 3' primer) PCR primer binding sites and consists of an oligonucleotide with a 5'-reporter dye (e.g., FAM, 6-carboxyfluorescein) and a quencher dye (e.g., TAMRA, 6-carboxytetramethylrhodamine) which quenches the emission spectra of the reporter dye as long as both dyes are attached to the probe. The probe signals the formation of PCR amplicons by a process involving the polymerase-induced nucleolytic degradation of the double-labeled fluorogenic probe that anneals to the target template at a site between the two primer recognition sequences (see, e.g., U.S. Pat. No. 6,387,652).

The measurement of the released fluorescent emission following each round of PCR amplification (Heid et al., (1996) *Genome Research*, 6:986-994) thus forms the basis for quantifying the amount of target nucleic acid present in a sample at the initiation of the PCR reaction. Since the exponential accumulation of the fluorescent signal directly reflects the exponential accumulation of the PCR amplification product, this reaction is monitored in real time. Hardware, such as the model 7700 and model 7900HT Sequence Detection Systems, available from Applied Biosystems (Foster City, Calif.) can be used to automate the detection and quantitative measurement of these signals, which are stoichiometrically related to the quantities of amplicons produced. From the output data of the RTm PCR, quantification from a reliable back calculation to the input target DNA sequence is possible using standard curves generated with known amounts of template DNA.

Primers and probes useful in RTm PCR identification and quantification of a bacteria population having a polynucleotide sequence of interest may be designed to correspond to the polynucleotide of interest. In one embodiment of the present invention, primers and probes useful in RTm PCR correspond to regions of the bvcA genes identified herein. Primers useful in the present embodiment include, but are not limited to, those having the polynucleotide sequence of any one of SEQ ID NO: 9-22. Useful RTm PCR probes include, but are not limited to, those polynucleotide which hybridize to any one SEQ ID NO: 1-8. In a preferred embodiment, the PCR primer pair and probe for use in RTm PCR consist of a first (forward) primer having the polynucleotide sequence of SEQ ID NO: 23, a second (reverse) primer having the polynucleotide sequence of SEQ ID NO: 24 and probe having the polynucleotide sequence of SEQ ID NO: 25.

RTm PCR may be used to identify and quantify a population of dechlorinating bacteria having a polynucleotide sequence of interest by first isolating DNA from a sample suspected of having dechlorinating activity using any one of the methods known in the art (see e.g., He, J. et al. (2003) *Appl. Environ. Microbiol.* 65:485-495). The isolated DNA may be amplified using RTm PCR by contacting the sample with any one of the probes described above, and any one of the primer pairs described above. Preferably, the probe is fluorogenically labeled. For example, the probe is labeled with 6-carboxy-fluorescein (FAM) as a reporter fluorochrome on the 5' end, and N,N,N',N'-tetramethyl-6-carboxy-rhodamine (TAMRA) as quencher on the 3' end. The isolated DNA sample is subjected to RTm PCR using any one of the RTm PCR protocols known in the art, such as the RTm PCR protocol described in U.S. Provisional Application No. 60/474,831, which is hereby incorporated by reference. During the course of PCR the fluorescent signal generated by the reaction may be continuously monitored using detection hardware, such as the model 7700 and model 7900HT Sequence Detection Systems, available from Applied Biosystems (Foster City, Calif.).

The amount of dechlorinating bacteria containing the polynucleotide sequence of interest, present in the sample may be determined using RTm PCR, by comparing the results of the RTm PCR assay described above to a calibration curve. A calibration curve (log DNA concentration versus arbitrarily set cycle threshold value, $C_T$) may be obtained using serial dilutions of DNA of known concentration. The $C_T$ values obtained for each sample may be compared with the standard curve to determine the DNA concentration of *Dehalococcoides*. Using an average molecular weight of 660 for a base pair in dsDNA, one reductive dehalogenase gene operon per *Dehalococcoides* genome, and a genome size of 1.5 Mbp (www.tigr.org), the following equation may be used to ascertain the number of *Dehalococcoides*-derived reductive dehalogenase gene copies that were present in the DNA obtained from 1 ml of the dechlorinating enrichment culture:

$$\text{Reductive dehalogenase gene copies/ml} = \frac{DNA \text{ (μg/ml)} \times 6.023 \times 10^{23}}{(1.5 \times 10^6 \times 660) \times 10^6}$$

EXAMPLES

The present invention is further exemplified in the following non-limiting Examples. Unless otherwise stated, parts and percentages are by weight and degrees are Celsius. As apparent to one of ordinary skill in the art, these Examples, while indicating preferred embodiments of the invention, are given by way of illustration only.

Chemicals were purchased from Aldrich (Milwaukee, Wis.) or Sigma Chemical Co. (St Louis, Mo.), except for VC, which was obtained from Fluka Chemical Corp. (Ronkonkoma, N.Y.). Restriction enzymes were purchased from Promega Biosciences, Inc. (San Luis Obispo, Calif.), and enzymes used for cell lysis were from Sigma Chemical Co. PCR reagents were purchased from Applied Biosystems (Foster City, Calif.), and BSA was purchased from Roche (Mannheim, Germany).

Example 1

Isolation of DNA from VC-Dechlorinating Cultures

Genomic DNA was obtained from pure cultures of *Dehalococcoides* sp. strain BAV1, and several VC-dechlorinating enrichment cultures derived from river sediments (the Red Cedar, Au Sable and Père Marquette Rivers, all three in Michigan (Löffler F., et al. (2000) *Appl. Environ. Microbiol.* 66:1369-1374) and chloroethene-contaminated aquifers (the Minerva site in Ohio, the Hydrite Chemical site in Wisconsin, and the Bachman Road site in Michigan (Lenvay, J., et al. (2003) *Environ. Sci. Tech.* 37:1422-1431).

VC-dechlorinating cultures were grown in 160-ml serum bottles containing 100 ml reduced basal salts medium amended with acetate (2 mM) as a carbon source, hydrogen (0.2 mmoles) as electron donor, and VC (0.12 mmoles) as electron acceptor as described by He, J., et al. (2003) *Nature* 424:62-65.

Genomic DNA was also available from isolates *Dehalococcoides* sp. strain CBDB1, *Dehalococcoides* sp. strain FL2, *Dehalococcoides ethenogenes* strain 195, and PCE-to-ethene-dechlorinating mixed cultures successfully employed in bioaugmentation approaches in the field (Major, D., et al. (2002) *Environ. Sci. Technol.* 36:5106-5116) and Bio-Dechlor INOCULUM (www.regenesis.com), a culture based on the Bachman Road site inoculum (Lenvay, J., et al. (2003) *Environ. Sci. Tech.* 37:1422-1431), and the VC-to-ethene-dechlorinating Victoria culture containing strain VS (Cupples A., et al. (2003) *Appl. Environ. Micobiol.* 69:953-959).

Example 2

Identification of RDase Genes

RDase genes were identified by amplifying genomic DNA using specially designed PCR primer pairs targeted to known conserved regions of RDase genes. Clone libraries were established by cloning the resulting amplicons in *E. coli*. The sequences of the cloned gene fragments contained in the clone libraries were compared with known RDase gene sequences.

Primer Design

Multiple alignments of full-length protein and DNA sequences of TceA (AAN85590, AAN85588, AAF73916A) and RDases identified from the genome of *Dehalococcoides ethenogenes* strain 195 were constructed using ClustalW and ClustalX (see, e.g., Thompson, J., et al. (1997) *Nucleic Acid Res.* 25:4876-4882). Conserved amino acid sequences were identified and used to design degenerate PCR primers. The following conserved regions were targeted for designing forward and reverse primers, respectively a di-arginine containing stretch near the amino-terminus of the RDases (i.e., RRXFXK) and a region in the B gene (i.e., WYEW). The expected size of amplicons generated with these primers ranged from 1,500-1,700 bp. The degenerate primer set used in this study and its target sequences are listed in Table 1. Specific primer sets (Table 2) targeting each of the RDases identified in the clone libraries (see below) were designed using Primerquest (http://biotools.idtdna.com/Primerquest/).

PCR, Cloning, and Amplicon Analysis.

DNA from VC-dechlorinating pure and mixed cultures was extracted using the Qiagen mini kit (Qiagen, Valencia, Calif.) as described previously (He, J. et al. (2003) *Nature* 424:62-65). Extracted DNA was used as template for amplification with degenerate primers RRF2 and B1 R (Table 1). PCR reactions were performed in total volumes of 30 μl with final concentration of reactants as follows: GeneAmp® PCR buffer (1×), $MgCl_2$ (3.0 mM), BSA (0.13 mg/ml), dNTPs (0.25 mM each), primers (0.5 μM each), Taq DNA polymerase (2 units), and DNA (1-2 ng/μl).

PCR conditions included an initial denaturation step at 94° C. for 2 min 10 sec, followed by 30 cycles of 94° C. for 30 sec, 48° C. for 45 sec, and 72° C. for 2 min 10 sec, and a final extension step at 72° C. for 6 min. The same conditions were used for amplification with the specific primers listed in Table 2 except that the primer concentrations were 0.1 μM, the $MgCl_2$ concentration was 2.0 mM, and the annealing temperature was 51° C. Amplicons generated from strain BAV1 genomic DNA with primers RRF2 and B1R were purified using the QIAquick™ PCR purification kit (Qiagen), ligated into vector pCR2.1 by TA cloning (TOPO or TA cloning kit, Invitrogen, Carlsbad, Calif.), and cloned in competent *E. coli* cells provided with the cloning kit following manufacturer recommendations.

TABLE 2

Specific Primers

| Specific Primers | Primer Sequence 5'→3' | Gene targeted | SEQ ID NO |
|---|---|---|---|
| bavrdA1F | GTACCGATGATGATTCACG | $rdhA1_{BAv1}$ | 9 |
| bavrdA1R | AGCCATACATGTCCCGCAA | $rdhA1_{BAv1}$ | 16 |
| bavrdA2F | TGCAAGCAGGTTCCCAT | $rdhA2_{BAv1}$ | 10 |
| bavrdA2R | GGCTTGATGTTAAACCC | $rdhA2_{BAv1}$ | 17 |
| bavrdA3F | GATTATGCTTTGTTTGGG | $rdhA3_{BAv1}$ | 11 |
| bavrdA3R | TTAGAACAACCACCAGGC | $rdhA3_{BAv1}$ | 18 |
| bavrdA4F | ATGCCATGTATTCGGTC | $rdhA4_{BAv1}$ | 12 |
| bavrdA4R | TCAACCCTCCAGCCTTTA | $rdhA4_{BAv1}$ | 19 |
| bavrdA5F | GTTAATGTTGCGAAGGCT | $rdhA5_{BAv1}$ | 13 |
| bavrdA5R | CATGGTCTTTTCCATATTGGC | $rdhA5_{BAv1}$ | 20 |
| bvcAF | TGCCTCAAGTACAGGTGGT | $rdhA6_{BAv1}$-bvcA | 14 |
| bvcAR | ATTGTGGAGGACCTACCT | $rdhA6_{BAv1}$-bvcA | 21 |
| bavrdA7F | AAACTGCTCAGGGTTG | $rdhA7_{BAv1}$ | 15 |
| bavrdA7R | TTGCCCGGAACACTGTA | $rdhA7_{BAv1}$ | 22 |

Recombinant *E. coli* clones were screened by verifying the correct insert size using direct PCR with primers targeting the pCR2.1 cloning vector flanking the inserted fragment. Amplicons of the predicted length were digested individually with the enzymes MspI and HhaI (Promega Biosciences), as per manufacturer recommendations for Restriction Fragment Length Polymorphism (RFLP) analysis. Plasmid DNA from recombinant clones containing the different inserts was extracted using the Qiaprep™ spin miniprep kit (Qiagen), and partially sequenced with vector specific primers using an ABI 3100 genetic analyzer (Applied Biosystems, Foster City, Calif.).

A second clone library was established using the same procedure with genomic DNA from the Bachman enrichment culture, from which strain BAV1 was isolated. Inserts of the predicted length were analyzed with BLASTX to verify similarity and the presence of consensus sequences indicative of RDase genes. Further, DNA sequences were translated using the TRANSLATE program (http://us.expasy.org/tools/dna.html) into amino acid sequences to examine for known RDase motifs. Partial protein sequences were aligned using the programs clustalW and clustalX. The designation of RDase genes was adapted from Villemur, R. et al. (2002) *Can. J. Microbiol.* 48:697-706.

The degenerate primer pair RRF2 and B1R produced fragments of the expected size and a total of seven clones were recovered in the clone library generated with DNA from the VC-dechlorinating Bachman mixed culture. Restriction analysis identified five clone types with distinct inserts, designated rdhA1-5$_{BAV1}$ (SEQ ID NO: 2-6). In a second clone library constructed with strain BAV1 pure culture DNA, 54 clones were recovered, and two additional RDase sequences were identified, i.e., rdhA6$_{BAV1}$ (SEQ ID NO: 7) and rdhA7$_{BAV1}$ (SEQ ID NO: 8). No clones harboring rdhA3$_{BAV1}$, rdhA4$_{BAV1}$, or rdhA5$_{BAV1}$ were identified in the second BAV1 clone library but subsequent PCR analysis using primer pairs targeting each of the rdhA1-7$_{BAV1}$ sequences, demonstrated the presence of all RDase fragments in isolate BAV1 and in the Bachman mixed culture from which BAV1 was isolated (see, He, J. et al. (2003) Nature 424:62-65).

Example 3

Expression and Analysis of RDase Genes

RNA Isolation

Biomass was collected by centrifugation and cell pellets were immediately frozen at −70° C. All solutions used for RNA extraction were prepared with diethyl pyrocarbonate (DEPC)-treated water, free of DNases and RNases-. Total RNA was extracted using the RNeasy extraction kit (Qiagen) according to the manufacturer's recommendations with the following modifications to enhance cell lysis and RNA yields. The cell pellet was suspended in 100 μl lysozyme digestion buffer (30 mM Tris-HCl, 1 mM EDTA, pH 8.0, 15 mg/ml lysozyme), 20 μl proteinase K (25 mg/ml) and 10 μl achromopeptidase (1,800 U/μl). The suspension was mixed and incubated at room temperature for 10 min, before 50 μl 0.1% Triton X-100 was added, and the mixture was shaken vigorously for 10 sec. Lysis buffer RLT (350 μl, provided with the RNeasy extraction kit) was added, and the lysate was transferred into a MicroRNA Bead Tube (Mo Bio Laboratories, Carlsbad, Calif.) and shaken horizontally on a Vortex mixer at maximum speed for 10 min. DNA was removed by two consecutive on-column treatments with RNase-free DNase (Qiagen) as described by the manufacturer. RNA concentrations were determined spectrophotometrically at 260 nm using an HP 8453 photodiodearray UV/Vis spectrophotometer.

Expression Analysis of RDase Genes

Reverse transcription PCR (RT-PCR) was performed with the two-step RT-PCR sensiscript kit (Qiagen). First, reverse transcription reactions were performed with 1 mM random hexamer primers (Promega) and 5-50 ng of extracted RNA in a total volume of 20 μl for 3 hrs at 37° C. according to the manufacturer's recommendations. Then, PCR was performed with degenerate primers RRF2 and B1R (Table 1) or with specific primers (Table 2) using the PCR conditions specified above. RT-PCR amplification products were examined by gel electrophoresis on 1.5% agarose gels, and amplicons generated with primers RRF2 and B1R were cloned using the TOPO TA cloning kit. Recombinant E. coli clones were identified as described above, and the inserts were characterized by restriction analysis and sequenced. For nested PCR, the initial amplification was performed with primers RRF2 and B1R, and (1 μl) of the amplified product was used as template in a second round of PCR with the specific primers listed in Table 2.

PCR amplification with degenerate primers RRF2 and B1R using cDNA obtained from VC-grown BAV1 cells as template yielded a PCR fragment of the expected size (approximately 1,700 bp). In contrast, no amplification occurred without the RT-PCR step, confirming that all DNA was successfully removed from the RNA preparation, and that the observed 1,700 bp amplicon was generated from mRNA. Amplification of cDNA occurred with degenerate primers RRF2 and B1R targeting the reductase internal RRXFXK motif and the WYEW sequence in the B gene, respectively, indicating that both genes are co-transcribed. A clone library generated with the PCR-amplified cDNA contained a single insert, and RFLP and sequence analyses of six clones confirmed that the cloned fragments were identical to rdhA6$_{BAV1}$ (SEQ ID NO: 7).

Figure 2:
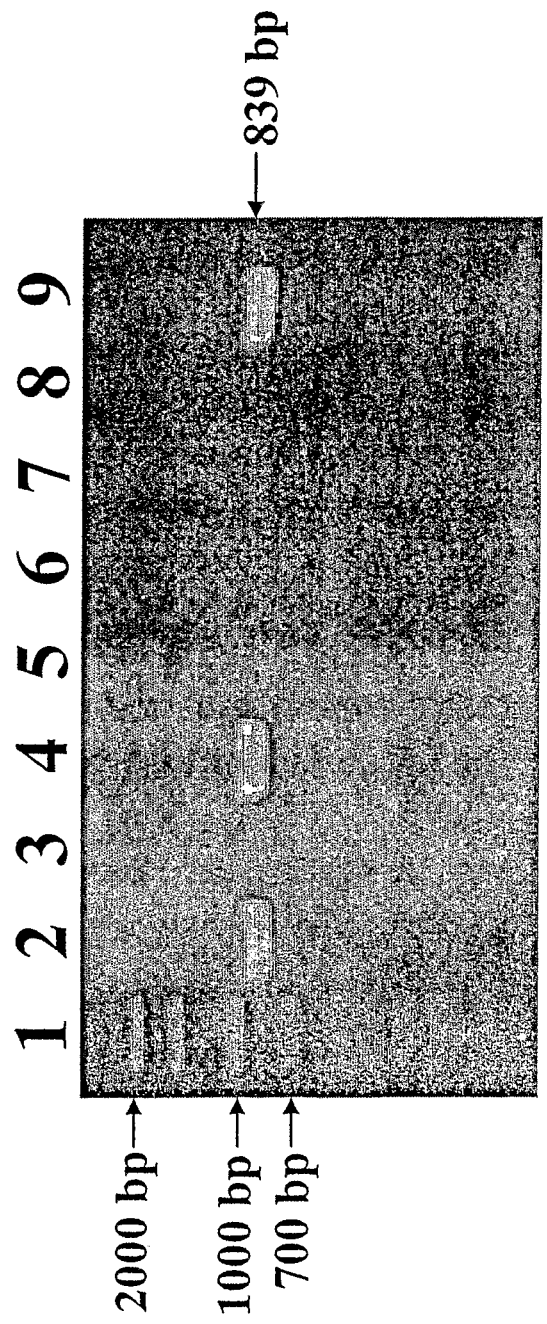
FIG. 2 shows the results of PCR amplification of the bvcA gene with specific primers bvcAF and bvcAR and templates generated from VC-grown BAV1 cultures and cis-DCE grown cultures of *Dehalococcoides* sp. strain FL2.

Transcription of the VC RDase found in the cDNA clone library was explored in more detail using the specific primer pair bvcAF and bvcAR (Table 2). PCR reactions using cDNA generated from VC-grown BAV1 cultures as template yielded amplicons of the correct size, which are shown in FIG. 2 (DNA size marker 50-2000 bp (Biorad Laboratories, Hercules, Calif.) (lane 1); BAV1 cDNA (lane 2); BAV1 total RNA (lane 3); BAV1 genomic DNA (lane 4), FL2 cDNA (lane 5), FL2 total RNA (lane 6), FL2 genomic DNA (lane 7); H$_2$O (lane 8), plasmid DNA containing rdhA6$_{BAV1}$ gene fragment (lane 9)), and sequence analysis confirmed their identity. No amplicons were obtained when total RNA extracts were used as template, confirming that no residual genomic DNA was present (FIG. 2). An additional control shown in FIG. 2 involved cDNA obtained from a cis-DCE-grown culture of Dehalococcoides sp. strain FL2. No amplicons were obtained with primer pair bvcAF and bvcAR, which was expected since strain FL2 cannot grow with VC as electron acceptor.

Seven RDase gene fragments were identified in strain BAV1, however, rdhA6$_{BAV1}$ (SEQ ID NO: 7) was the only RDase gene fragment present in a cDNA clone library established with total RNA obtained from VC-grown BAV1 cultures. PCR reactions performed with the specific primers listed in Table 2 and cDNA as template confirmed these findings, and amplification only occurred with the bvcAF/bvcAR primer pair targeting the rdhA6$_{BAV1}$ sequence. To test if the six other RDase genes were expressed at lower levels, the PCR product generated from cDNA with primer pair RRF2/B1R was used for a subsequent nested PCR with the specific primer pairs listed in Table 2. These analyses suggested that genes contributing to fragments rdhA1$_{BAV1}$ (SEQ ID NO: 2), rdhA3$_{BAV1}$ (SEQ ID NO: 4), rdhA4$_{BAV1}$ (SEQ ID NO: 5), rdhA5$_{BAV1}$ (SEQ ID NO: 6), and rdhA7$_{BAV1}$ (SEQ ID NO: 8) were also expressed, but at significantly lower levels than rdhA6$_{BAV1}$ (SEQ ID NO: 7). The only RDase gene not transcribed at detectable levels in VC-grown BAV1 cells correlated with fragment rdhA2$_{BAV1}$ (SEQ ID NO: 3).

Example 4

Chromosome Walking and Assembling the bvcA Coding Sequence

To extend the reductive dehalogenase gene fragment rdhA6$_{BAV1}$, the TOPO Walker kit from Invitrogen (Carlsbad, Calif.) was used with primers 5Bfcomp (5'ACCACCTG-TACTTGAGGCA-3'; SEQ ID NO: 36), and 5BGR (5'AC-CCGACAAAGAACTGGTTTCG-3'; SEQ ID NO: 37). The primer binding sites are illustrated in FIG. 1.

Purified genomic DNA of strain BAV1 was digested with Pst I and Sac I for 2 hrs at 37° C. The digested DNA was dephosphorylated using calf alkaline phosphatase and precipitated with phenol:chloroform (1:1 pH 6.7) following the TOPO Walker manual. Primer extension with primer 5Bfcomp at an annealing temperature of 55° C. created a 3' overhang required for TOPO linking. TOPO linking was performed as to manufacturer's recommendations, and the TOPO-linked DNA was then subjected to amplification with primer 5BGr at an annealing temperature of 57° C. Amplification was verified on 1% agarose gels.

The 305 bp product was purified using the Qiaquick Gel Extraction Kit (Qiagen) and cloned into *E. coli* using the cloning Kit (Invitrogen). Primers M13F and M13R were used to PCR amplify the cloned fragment according to the protocol for 'alternative method of analysis' provided with the TOPO XL PCR Cloning kit. The purified PCR product containing the 305 bp insert was sequenced using primers M13F and M13R. This sequence was aligned with the previously obtained rdhA6$_{BAV1}$ gene fragment sequence, and the coding region was determined using Frameplot. Ishikawa, J., et al. (1999) *FEMS Microbiol. Lett.* 174:251-253.

Expression Analysis of RDase Genes

Since the fragments generated with primer pair RRF2 and B1R lacked approximately 30 bp on the 3' end of the RDase genes, the rdhA6$_{BAV1}$ gene fragment was extended and the missing upstream portion of the RDase gene was obtained. The complete gene implicated in VC reductive dechlorination in *Dehalococcoides* sp. strain BAV1 was designated bvcA (SEQ ID NO: 1). The translated BvcA protein sequence contained the twin arginine motif (RRXFXK) in the form RRD-FMK. The chromosomal organization of the bvcA region is shown in FIG. 1. The deduced coding sequence of bvcA is 1,550 nucleotides long, which is predicted to encode a 516 amino acid protein. A second incomplete open reading frame for the B gene bvcB was found 51 nucleotides downstream of the bvcA stop codon TAA.

The coding sequences of the RDase gene and B gene fragments were deposited in GenBank under accession numbers AY553222-AY553228 (SEQ ID NO: 2-8). GenBank accession number AY563562 (SEQ ID NO: 1) was assigned to the complete sequence of the VC reductive dehalogenase bvcA. The complete sequences of the isolated RDase genes and B gene fragments are shown in Table 3 below.

TABLE 3

Isolated nucleic acid sequences

GENE: bvcA

SEQ ID NO: 1
ATGCATAATTTCCATTGTACGATAAGTAGGCGAGATTTTATGAAGGGATT
GGGGTTAGCGGGAGCAGGGATAGGTGCCGCGACTTCAGTTATGCCGAATT
TTCACGACTTGGATGAAGTAATTTCTGCTGCTAGTGCCGAAACCAGTTCT
TTGTCGGGTAAATCTCTTAATAATTTTCCTTGGTATGTGAAAGAAAGGGA
TTTTGAAAATCCTACCATTGATATAGATTGGTCTATACTTGCGCGTAATG
ACGGTTACAATCATCAGGGAGCCTATTGGGGACCTGTACCTGAAAATGGA
GATGATAAAAGGTATCCTGATCCCGCGGACCAGTGTCTTACTCTACCAGA
AAAGAGAGATCTTTATTTAGCGTGGGCAAAACAGCAATTTCCTGACTGGG
AACCAGGAATTAATGGCCATGGGCCAACAAGGGACGAAGCTTTATGGTTT
GCCTCAAGTACAGGTGGTATCGGTAGGTATAGAATTCCTGGTACCCAGCA
AATGATGTCCACAATGCGTCTTGACGGGTCTACTGGTGGTTGGGGTTATT
TCAATCAACCACCGGCAGCAGTCTGGGGAGGGAAATACCCAAGGTGGGAA
GGAACTCCTGAAGAGAATACGTTGATGATGCGAACTGTTTGTCAATTTTT
TGGTTACTCCAGTATAGGTGTAATGCCAATCACCAGCAATACAAAGAAGC
TTTTTTTTGAAAAGCAAATACCTTTCCAATTTATGGCTGGAGATCCCGGT
GTATTTGGGGGAACGGGAAATGTGCAGTTTGATGTCCCGCTGCCAAAGAC
ACCTGTTCCAATAGTCTGGGAGGAAGTCGATAAAGGGTATTATAATGACC
AGAAAATTGTAATACCCAATAAGGCTAACTGGGTATTAACAATGACAATG
CCTTTACCAGAAGATCGTTTTAAACGTTCTCTAGGGTGGTCACTTGACGC
TTCAAGTATGATTGCCTATCCTCAGATGGCTTTTAATGGAGGCCGAGTTC
AGACTTTTTTAAAAGCACTTGGCTATCAAGGACTTGGTGGCGACGTGGCT
ATGTGGGGACCTGGTGGTGCTTTTGGAGTTATGAGTGGTCTTTCCGAACA
AGGTCGTGCTGCTAATGAAATCAGCCCCAAATACGGTTCGGCAACTAAGG
GCTCTAATCGATTAGTTTGTGATTTGCCCATGGTTCCGACCAAGCCAATT
GATGCTGGCATACACAAATTCTGTGAAACGTGTGGCATTTGTACAACAGT
TTGTCCCTCAAATGCTATCCAGGTAGGTCCTCCACAATGGAGTAATAATC
GGTGGGATAATACCCCTGGTTATCTTGGTTATCGACTTAACTGGGGTAGA
TGTGTTCTTTGTACAAACTGTGAGACCTATTGCCCATTTTTTAACATGAC
TAATGGTTCTTTGATTCATAACGTAGTCAGATCCACAGTTGCAGCTACAC
CGGTTTTTAATTCATTTTTCCGCCAAATGGAACATACATTTGGATATGGT
ATGAAAGATGATTTAAACGATTGGTGGAATCAATCACACAAGCCTTGGTA
A

Gene: rdhA1$_{BAV1}$ (1393)

SEQ ID NO: 2
GGGAGCAGGTATTGGTACCGCAGCTGCAACTGCAACTGCCCAATGTTTC
ACGACCTTGATGAGGTGATCGCTTCACCCTCAGCAGCAAATGAAAGACCA
TGGTGGGTAAAGGATAGAGAATTGTACCAGCCCACGCTTGAGGTAGATTG
GGATATTATGACTCCGCCGGATGGCAGAGTTAGCGGGCAGCAGACTGAAA
CCCAAATTCACTACCTTGGAAGCGAAGAGGTAAAAAGGCGTTTATCATCG
AATATAATGTCTCCCAACGTTGAAGCCGCTATCAATAATACACCGGGGAA
AACTTTGCGTGACCAAGCCTTGGGACTCAGCTCAATTGTACCGATGATGA
TTCACGGTATATCTTTCATGGGCCCGGGTCTTATTCCTACCCCTGCAACA
ACCGGCGCCCCTAAATGGGAGGGTACACCTGAAGAAAACAGCCGGATGGT
ACGCAGTGTTCTTACTTTTCTGGGTGCCGGTATGGTTGGTTTTGGTGAAA
TTTCCAGCCAGGAGAGAGAAAAAATATTCTACACTTATCATAAACAAGTC
CCCAACAAGAGGCAGGTATTTGAGGATGTAGATGTTGGCTACGAAGGTAC
CGATAAATACGTTTTCCCTGACAGGAAGCTTTATAAGATATCTATGTCCC
TGCCTATGTCCCGGGAAATGTATCGAACTTCCGACAGATCTTCATTACAA
TTTGCAGCCAATGTATCCCGTTACCGTCACTTCAGTATGCTTCAGCCGGC
TTTCCAAGAATTTATCAGAGGTATCGGGTATCATTGTTATGGCTATCCTG
TACCACAGGCTGGCCCTATGCCTGCAGCAGTTAGTGCTATTCTTACCGGT
CTGGCGGAATCAAGCCGGAATAGCGGGTATTGTATCTCTCCGGACTACGG
ACCGGTTTCAGGTTTCTTTACATTTGTAACTGACTTGCCAGTTGAACCCA
CTACACCTATAGATGCTGGTATCTGGCGCTTTTGTCAGACTTGCAATAAG
TGTGCCCAAAACTGTCCGACCCAAGTAATCCCTTACGATAAAGAACCGAG
TTGGGAACTCCCTACATTATATGGTAAACCGGATATTATCCATCCTTCCG
GCAAGCGGATGTTCTACGCAAACCATATAGAGTGTTGGATGTACTGTTTT
GAAGGCGGTTGCGGGACATGTATGGCTACATGTACTTTTAATGTAAATGG
CGCAGCCATGGTACATGATGTGGTTAAGGCTACACTAGCCACAACTTCAA
TGTTTAACGAATTTCTGTGGAAAGCGGATAAGACCTTCGGCTATGGGGTG
AAGTCTGGGGAAGAAAAAGAAGACTGGTGGGATTTATCCTTACCATCGAT
GGGCTGGGATACAACTTCCTTCTCAAAACATGGTGGTTATTAA

Gene: rdhA2$_{BAV1}$ (1462)

SEQ ID NO: 3
GGGTGCTGCAACAGCTTCAGCACCAGTGTTTCATGATTTGGATGAAATGA
TNACATCTGTACCTAAATCTACAACTCAACATGCTTGGTGGGTAAAAGAA
AGAGACTATGAGGATATTACTACGCCTGTTGATTGGACTGTTTGGTCACG
ACGTGAGGCCTTAAAGAACCCGATGCCGCCCGGTTTTGCCGGGAATTATG
TGCCTAAAGAACAGGCCAGATTACAGAGCTTTCGTAATGAAATTAAAAGA
GGTATAACTGAAAAAATTCCCGGTGCAACTTTACGTGATTGGGCTCTTTC
GGAAGCTGGGCGGAGCAATACCACCTCTTCGTCATGGATGGGCTTGATG
TTAAACCCCCATGGTTATGGGGTGAAGCCTCTGCTTTACCGGTTGAACCT
TGGCCAGAAGGTGCACCCAAATGGGAATCTACTCCGGAAGATAATCTTAG
AACGGTTCAGGCTGCCGGACACTATTTCGGTACGCCTCAGGTAGGCGCCA
TGGAAATCAATGAACATATGATTCGTATGTTCGATAAAGATGGTTTTGAA
CATAACTATAGTGCAAGTTATGAGAAACCCATGATGCGATTCCGCTCTGA
GTGGTTTGAAGATATTCCGGTTGGTTTTCAGGATGCCAATCAGGTAAAAC
ATATTCCAAAATCATGTAAATGGGCGGTTACTTATATTGCCGCCAAAGAA
AATGCACTGCAGATGACTTATGGCATGCGTACTGGTGATCCTCAAGATCC
GTGGTATAAGCGCATCTTTCCTTTGGGTTATACAACAGGAGAGGCTTATT
CCAAAGCTGATTATGTTAAAGTCCAATTTATGAAATTCATAAAAATGTTG
GGTTATCAAACTTATTATATGGGTTTAGCCGGTGGTACAAGTTCAAATAG
TCCTGCAGGAATTTTCTCAGGTTTGGCAGAAGAGGCTCGCCCTGCGCTGG
CCTGTTCACCTTATTATGGTAATGCGGTACGTCATATTGGAATCATTGTT
ACCGATATGCCTCTGAGTCCCACTAAGCCTATTGATGCCGGTATTGTTAA
TTTCTGCAAGATATGCAAAAAATGTGCGGAGACTTGCCCTTCCGGCGCTA
TTAGTATGGAAACTGAACAACAATGGGAACCTGCTTGCACGGGGAATAAT
CCCGGTCGAAAAACTTGGTATTTGGACTGGTTTAAATGTCGTCCATGGGG
TTCCCCATATTATTGTCCCAATTGTCAAACAGTCTGCCCATTTAACAATC
CTAACAAAGCAATTATCCATAACGCTGTACNNANNACGGCTGCCACCACT
CCAATATTTAACAGCTTCTTTTCATCTTTGGATAAGAGCTTTGGTTATGC
TCACCAGCGTTCGGACGAAGAGCGACTTAACTGGTGGTACAGGGATCTTA
ATACATGGCAATATGATGATGTTTTTGGTATGGGCACAAAAGATCCAAAA
TCTTGGTTATGA

GENE: rdhA3$_{BAV1}$-(1437)

SEQ ID NO: 4
GGAGCAGGCCTAGGAGCAGCTGCGTCCACTACTCCGGTGTTTCATGACAT
GGATGAACTCATTGCTTCATCTGGTTTTAGTGGTTCAGAATCATATTCCA
GATATCCATGGTGGGTCAAAGAAGTGGATAAGCCGACCGCAGAGATAGAC
TGGAATCTTATGAAACCCTATGACATGCGTAATTCAGATAAATGGGCTAC
CCCAGAACTTCTTGCCAAATATTATGCTGCTCAATTAAAGCATACTAAGG
AATGCATACTGAATAAAACGCCCGGCAGTAGTCTGAAGGATTATGCTTTG

TABLE 3-continued

Isolated nucleic acid sequences

TTTGGGGTATCAAGGGGTCCATGATGCAAAATGTACCAAAGGTTGGAAC
CCCTGAACCCAATCTGGAATATCTCTATCCTACAGATACACTTTACTTCAC
TTGGTTTACCCCGGTATGAAGGCACCCCTGAGGAAAACCTTAAAATGTGT
GCTGCAGCTATTCATCTACTCGGAGGCCGCGATATAAGCGTTGTAGAGGT
AGATGATAATGTTAAAAAGGTCCTTTATTCGCATTCTGCTATGCTAATGG
GAGGAAAGCCGAGTAGAGCCATTGTTTGGGAAGACGTAGATAATGCGTAT
GAAACACCAGAAAAAATGGTAATTCCCAACAAATGCAAATGGGCGTTGGT
GTATTCATGCCCTCAGTCTCAATTATCAAGGTATCGAAGTGTTATCATGG
GCAAATTTGGGGTATTTGGAGCATACTCTGATATAGCAGTTATGGATCAA
CGTCTACAAAAATTCCTGCGTATATTGGGATATCAGGGTGTTTTGGATGG
TTTCGGTGGGGGCAATAGCATAAGTAGTAATTCGGGCTTTGGGGTACTTG
CAGGCAGTGGTGAGATTGGTAGACATGACTACGTAAATTCTCCCAGTTTT
GGGGCCTTGATGCGGATGAGTCAATTTATACTAACTGACTTACCTCTAGC
ACCTACTAAACCCATTGATGCGGGTATGTGGAAATTCTGCCAGTCATGTA
AGAAATGTGCCGATATGTGCCCATCTGGGGCTATCTCCAAAGAGGCTGAA
CCTACTTGGGAGCCTACGGGATGTATGGAATGGCACTGGCCGCAAGCTTTA
TCCGGTAGATTATCCCAAGTGTGGCCCTTGGAGGGGAATGCCTCCTGGAG
GGATTGGCCATATCTATGAAGCGGGGCCTGGTGGTTGTTCTAATTGCCAA
GTAGTATGTGTTTTCACCAAGACTCCTAAAGCTTCAATACATGATGTTAT
AAGACCACTTGTTTCCAGTACCTCGGTCTTTAACAGTTTCTTTACTACAC
TGGATAAATCATTCCATTACGGGGGGGCATTTGTTACTCCGCTGGGAGAA
GTTAATGTAAGCCCTGATGAATGGTGGAACCGTGATCTGAAAACTTATCC
GTTCAAAGGCAGAGTTATGGGAGACGGTTGGGCATAG

GENE: rdhA4$_{BAV1}$ (1432)

SEQ ID NO: 5

TTTTTATGAAGGGCTTGGGGTTAGCTGGTGCGGGACTTGGTGCCGTGTCGG
CTGTTACGCCTGTCTTTAGAGATTTGGATGAACTAACGTCTTCAGTTACG
GCACATCCTAAACGTGCCTGGTATGTAAAGGAACGAGAATTTGGGGATAT
CGGTATAGAAATTGACTGGAATATTTTGAAACGCCGTGACACCCGAGGTT
ATTCATATTGGAATCCGATGATTTGGAAGCAACATTATCCGGCTTACGAT
ATGGAAGCTTTTAATAAAGCTTTAGCACATAAGACCAAAGAACTCTGGCC
TGATTATGCAGGGCCGACTACCAGAGACTATTCCCTGAAAAATGCCATGT
ATTCGGTCGGGTTGGGATGCCCTCATTACCTGTACAATGTAGAACAGTTT
GGAGTGACACTTCCGCATCCTGCACCACGCCCGGAAGCAATTGGTATGCC
CAATTGGGCGGGTACTCCTGAAGAAAATTTCCAGATGATTCGGGCTGCTT
TTAGTCTTATCGGTTTAGGTCCTTCAATAGGTATAACCGAACTGGATGAT
AAGAGTAGGCGTTTTGTTCGGGAATATAATAACTGTGGTCAACACATAAT
ATTTGATGACAATATAACTGAAACATATCGGACGGCAAATCCTCCCACCA
TTCATATTCCTTCTTCACACCGGTATGTTATAGCTACCCACATATGGGG
GCAGACGAGATACTTCGCCGTGCTCCCTCAACCATTGGTGCATGCACAGA
GTCCATATCCTATGCCCGTGTAGCGTATGCCAAGAGTTTCGTTGAACAAT
TTATCCGCGGACTTGGCTATAACGTCGTCTATGGTCATTCACTTCAGGCT
GCACCAGCTATGGATTTCTGGAGTGGAGTAGGTAGGCATGCCCGTATGGG
GCAGGTTTGTGTGACACCTGAGAATGGTGCCATGATGCCCGTATCCATGCCA
TCTTCTTCACCGATTTACCACTCTCGCCTACAAAACCAATTGATGCTGGC
ATTACTAAGTTTTGCGAAACTTGCGGTATCTGTGCAGAGAGCTGTCCGGT
AGGAGCCGTTCCGGCTAAAGGAGTGAACCGGAATTGGGATTCTAACTGTG
ACGGCCAGAGCTTTGATAATGATATCGAAAGCGGCGGCACCGAGGTAATG
TACAATGTACCCGGCTATAAAGGCTGGAGGGTTGACGGGTTTAGATGCTT
AGCTGATTGCAATGGATGCAAGGGTTCCTGCCCTTTCAATGCTATTCCTA
ACGGGAGCTTCATCCACAGTCTAGTTAAAGCAACCACTTCAACTACCCCG
CTGTTCAATGGTTTCTTTACCCAAATGGAAAAATCTCTCCATTACGGTAA
ACAGGATAAAGACCCTGAATCCTGGTGGCATGAACCAAACGCCTGGCACG
TGTATGGCAGTAATCCGGGGTTACTGGGTTAA

GENE: rdhA5$_{BAV1}$ (1451)

SEQ ID NO: 6

ATTTTATGAAGGCTTTGGGTCTGGCTGGTGCCGGAGTCGGAGCAGTGTCT
GCTGCCGCCCCGGTTTTTCATGATGTGGATGAGCTGACTGCTCCTTCCGG
CGGCGTACAGAAGCTGCCGTGGTGGGTTAAAGAGAGGGAGTTCAAAGATC
TTACAGTACCCATTGACTGGCAGAATCTGCCCAAGATGGAGGGTGTTTTC
CCCATGCAGGCCAAGCCAACCCTGTCGGCTCAGGAAAGATATGCCATGGG
CATTCCCGGCGGCAGTTCGGGTACTTGGGCAGCCCTGAGCAGGCGCAAG
TACTTTTTGATTACATGAAAAGGAATTTCCGGGATGGGAACCCGGCTAT
GCCGGTCTGGGAGACAACCGGACAACCGCTCCTCTTCATGGCCACCAAATT
TATGCGTATGGGCATGTGGCCCGGTGAAATAAACATGGGCGGCAACAGGG
TTAATGTTGCCAAGGCTATTTCAGCGGCCGGAGGCACGGCTGCTTTCACC
TCATTCCTGGGGCTTCGCTCAACGAAACGCTCCGCCCGCAGGATTTCGG
TGTACCGCGTTGGGAAGGCACACCTGAAGAAAATCTGCTTACCTTGCGTC
AGGTAGTCCGTTCCTTGGCGGCTGTGATGTAGGTGCTCAGGAAATGGAT
TCAGATGTTTTCAAGCTTTTCATGAGAAAAGCGGCAAGAAACAGCTGGT
AATAGAAAACGTAGACGAAGGCGCTGAAACACCCACCAAACTGGTCATTC
CTGCCAAAGCCAAATATATCCTCCAGTGGACTGCCCCGCCCAGCCTTACGAA
TCCACCAGACGCCAGGCCGGCGAATATGAGGATGCCGCTGTATACTGGTC
TTATCAGAGGTTCCCCTTTGTCGGGGCTATTATCCAGGAATTTATCCACG
CTCTGGGATATACTGCGGTTTCAACCCATCTGTCTGGTTACCATTCCAGT
GCTGTAGCGACCTTGACCGGTATGGGGGAACATTGCCGTATGTCATCACC

CATCTTGGTTCCCAAATACGGCGTTACCAACCGGGCTATGTGGGTAATTA
TGACCGATATGCCTCTTATGTCCACTAAGCCTATAGACTTTGGGGTGTAT
GACTTCTGCAAGACCTGCGGTATCTGTGCGGACGCCTGCCCGTTCGGCTT
GATTGAAAAAGGCGACCCGACCTGGGAAGCTACTCAGCCGGGTAGCCGTC
CCGGTTTCAACGGATGGCGTACTAATACCACCATCTGTCCGCATTGTCCG
GTCTGCTCAAAGCAGTTGCCCCTTTAATACCAATGGCGACGGTTCTTTTAT
ACATGATTTGGTCAGAAACACAGTTTCTACCACCCCTATTTTCAACAGTT
TCTTTGCCAATATGGAAAAGACCATGGGATACGGACGCAAGGACCCGCGC
GACTGGTGGAATATAGATGATTATACCTACGGTATAAATACATCTTACTA
A

GENE: rdhA6$_{BAV1}$ (1451)

SEQ ID NO: 7

ATTGGGGTTAGCGGGAGCAGGGATAGGTGCCGCGACTTCAGTTATGCCGA
ATTTTCACGACTTGGATGAAGTAATTTCTGCTGCTAGTGCCGAAACCAGT
TCTTTGTCGGGTAAATCTCTTAATAATTTTTCCTTGGTATGTGAAAGAAAG
GGATTTTGAAAATCCTACCATTGATATAGATTGGTCTATACTTGCGCGTA
ATGACGGTTACAATCATCAGGGAGCCTATTGGGGACCTGTACCTGAAAAT
GGAGATGATAAAGGTATCCTGATCCCGCGGACCAGTGTCTTACTCTACC
AGAAAAGAGAGATCTTTATTTAGCGTGGGCAAAACAGCAATTTCCTGACT
GGGAACCAGGAATTAATGGCCATGGGCCAACAAGGGACGAAGCTTTATGG
TTTGCCTCAAGTACAGGTGGTATCGGTAGGTATAGAATTCCTGGTACCCA
GCAAATGATGTCCACAATGCGTCTTGACGGGTCTACTGGTGGTTGGGGTT
ATTTCAATCAACCACCGGCAGCAGTCTGGGGAGGGAAATACCCAAGGTGG
GAAGGAACTCCTGAAGAGAATACGTTGATGATGCGAACTGTTTGTCAATT
TTTTGGTTACTCCAGTATAGGTGTAATGCCAATCACCAGCAATACAAAGA
AGCTTTTTTTTGAAAAGCAAATACCTTTCCAATTTATGGCTGGAGATCCC
GGTATATTTGGGGGAACGGGAAATGTGCAGTTTGATGTCCCGCTGCCAAA
GACACCTGTTCCAATAGTCTGGGAGGAAGTCGATAAAGGGTATTATAATG
ACCAGAAAATTGTAATACCCAATAAGGCTAACTGGGTATTAACAATGACA
ATGCCTTTACCAGAAGATCGTTTTAAACGTTCTCTAGGGTGGTCACTTGA
CGCTTCAAGTATGATTGCCTATCCTCCAGATGGCTTTTAATGGAGGCCGAG
TTCAGACTTTTTTAAAAGCACTTGGCTATCAAGGACTTGGTGGCGACGTG
GCTATGTGGGGACCTGGTGGTGCTTTTGGAGTTATGAGTGGTCTTTCCGA
ACAAGGTCGTGCTGCTAATGAAATCAGCCCCAAATACGGTTCGGCAACTA
AGGGCTCTAATCGATTAGTTTGTGATTTGCCCATGGTTCCGACCAAGCCA
ATTGATGCTGGCATACAAATTCTGTGAAACGTGTGGCATTTGTACAAC
AGTTTGTCCCTCAAATGCTATCCAGGTAGGTCCTCCACAATGGAGTAATA
ATCGGTGGGATAATACCCCTGGTTATCTTGGTTATCGACTTAACTGGGGT
AGATGGTTCTTTGTACAACTGTGAGACCTATTGCCCATTTTTTAACAT
GACTAATGGTTCTTTGATTCATACAGTAGTCAGATCCACAGTTGCAGCTA
CACCGGTTTTTAATTCATTTTTCGCCAAATGGAACATACATTTGGATAT
GGTATGAAAGATGATTTAAACGATTGGTGGAATCAATCACACAAGCCTTG
GTAA

GENE: rdhA7$_{BAV1}$ (1533)

SEQ ID NO: 8

ATGAAGGCACTCGGTCTTGTAGGGGCTGGTGCGGGTGCGGCAGCAGCGTT
TGCTCCGGTGTTCAGAGACCTAGATGATTTAGTCGCTTCCCCCACTGCAA
CTTTCCCGCGTGCTTGGTGGATTAAGGAACGTGACCTGTGGATATTACC
ACCGAATATGACTGGAAAGCTATGTCCCGGCATGATACATGTGAAACCAT
GTGGATAAACATTCATGGGCAAAATATGTAGGTGTTGACAAGGTTAAAG
AAGCTGCCGCCAGTGCAGCCGCAATCAAAAAAGAAGCTCTGGAAACTGGT
AAACCGGGCATGGACTTAAGAGCAACTGCCCTGGGTAGTACCTCTGGTTT
GTATAATGCTCCTCAACCGTATTTCTCATATACTAAAACTGCTCAGGGTT
GGGGTGGTGTAAGAGTTTCACCGGTCAATCTACCATAAAAGGGCCTGAT
GTACTGGGAGTACCCAAGTGGCAGGGTGATCCTGATGCTAACCTCCAGGAT
GTTGCGAGCGGCTTTACGCTTCTATGGCGCTGCCCAGATTGGCGTAGTTC
CCTACGATACAAATGTAAAGAATAAATTAACCTGTGTTCGCGAAGGTGGC
ATGGCCTCTATGAGCGATAAATACATTGAAAAATGGCCTATACCCGCTGT
AGATCCCGTCGTTGTGTTCGAAGATGTTGAAAAAGGCTATGAAACCG
CTGAAACCGTTGGTGATTCCGGACAAAAAGGAACTTTTTGTGGTTTCAGTT
ATTCAGCCTATGAGCCGCGAAATGTGGCGACAGGGTAGCGGCAATTTGAG
AGTGGCAACTAATGGTCACCGTTATAGTCTGGCATCTGTTTGGCAAACCA
AAATTCAAGGCTTCCTGACGACCCTTGGTTATCAGGGTTTGGGTTATCT
ACCAGGGTCTTATGGATCCATGCCTACTATTCCTGGGTTTATTTTCTCTGG
TTTAGGTGAACTTGGGCGTTCAAATAATGTCTGTTTGAGCCCTGAATACG
GTTCAACCCACGGATCATTCCATTTCCTGACAGATTTGCCGTTAACTCCT
ACCAAACCTATAGATGCCGGTATGTGGCGGTTTCTGTAAGACTTTGTCGTAT
TTGCGCTGAAAACTGTCCTTCGCAGTCTATTTCATATGACAAAGAACCCT
CATGGGAAATCACTCCTTCCAAGTATGCTCCCAATGTTCCGGTAGAATAC
AGTGTTCCGGGCAAAAAGGTTTTCTGGCGTGATGAACATCTTGCAAACA
GTGGACTGAGAGTTGTGGTTATTCCTGGTGATATCTGCATGGGTTCCTGCG
TGTTCAACGTGGACAATGCCTCCATGATCACCAGGTAGTTAAAGGTACT
ATTGCTACCACCAGTCTCTTCAATGGTTTCATGAAACAGGCTGACAAGTT
CTTTGGTTATGGACTTACACCTGAGTCTGAGTGGAACAATTGGTGGGACA
TGAATCTGCCGGCCTATGCTTTTGATCTACTGTTGGTGTTACTGATGGT
GGTTACAAAGCCAAAGGCCTGCTCAGCAATAA

The amino acid sequence of the isolated RDase genes of the present invention was deduced using Translate tool (http://us.expasy.org/tools/dna.html). The deduced amino acid sequences are shown below.

Amino Acid Sequence: RdhA1$_{BAV1}$ (SEQ ID NO: 26)
(Accession # AY553222)
GAGIGTAAATATAPMFHDLDEVIASPSAANERPWWVKDRELYQPTLEVDW
DIMTPPDGRVSGQQTETQIHYLGSEEVKRRLSSNIMSPNVEAAINNTPGK
TLRDQALGLSSIVPMMIHGISFMGPGLIPTPATTGAPKWEGTPEENSRMV
RSVLTFLGAGMVGFGEISSQEREKIFYTYHKQVPNKRQVFEDVDVGYEGT
KDYVFPDRKLYKISMSLPMSREMYRTSDRSSLQFAANVSRYRHFSMLQPA
FQEFIRGIGYHCYGYPVPQAGPMPAAVASILTGLAESSRNSGYCISPDYG
PVSGFFTFVTDLPVEPTTPIDAGIWRFCQTCNKCAQNCPTQVIPYDKEPS
WELPTLYGKPDIIHPSGKRMFYANHIECWMYCFEGGCGTCMATCTFNVNG
AAMVHDVVKATLATTSMFNEFLWKADKTFGYGVKSGEEKEDWWDLSLPSM
GWDTTSFSKHGY Amino Acid Sequence: RdhA2$_{BAV1}$ (SEQ ID NO: 27)
(Accession # AY553223)
GAATASAPVFHDLDEMXTSVPKSTTQHAWWVKERDYEDITTPVDWTVWSR
REALKNPMPPGFAGNYVPKEQARLQSFRNEIKRGITEKIPGATLRDWALS
EAGRSNTTSSSWMGLDVKPPWLWGEASALPVEPWPEGAPKWESTPEDNLR
TVQAAGHYFGTPQVGAMEINEHMIRMFDKDGFEHNYSASYEKPMMRFRSE
WFEDIPVGFQDANQVKHIPKSCKWATVYIAAKENALQMTYGMRTGDPQDP
WYKRIFPLGYTTGEAYSKADYVKVQFMKFIKMLGYQTYYMGLAGGTSSNS
PAGIFSGLAEEARPALACSPYYGNAVRHIGIIVTDMPLSPTKPIDAGIVN
FCKVCKKCAETCPSGAISMETEQQWEPACTGNNPGRKTWYLDWFKCRPWG
SPYYCPNCQTVCPFNNPNKAIIHNAVXXTAATTPIFNSFFSSLDKSFGYA
HQRSDEERLNWYRDLNTWQYDDVFGMGTKDPKSWL Amino Acid Sequence: RdhA3$_{BAV1}$ (SEQ ID NO: 28)
(Accession # AY553224)
GAGLGAAASTTPVFHDMDELIASSGFSGSESYSRYPWWVKEVDKPTAEID
WNLMKPYDMRNSDKWATPELLAKYYAAQLKHTKECILNKTPGSSLKDYAL
FGGIKGSMMQNVPKVGTPEPNLEYLYPTDTLTSLGLPRYEGTPEENLKMC
AAAIHLLGGRDISVVEVDDNVKKVLYSHSAMLMGGKPSRAIVWEDVDNAY
ETPEKMVIPNKCKWALVYSCPQSQLSRYRSVIMGKFGVFGAYSDIAVMDQ
RLQKFLRILGYQGVLDGFGGGNSISSNSGFGVLAGSGEIGRHDYVNSPSF
GALMRMSQFILTDLPLAPTKPIDAGMWKFCQSCKKCADMCPSGAISKEAE
PTWEPTGVWNGTGRKLYPVDYPKCGPWRGMPPGGIGHIYEAGPGGCSNCQ
VVCVFTKTPKASIHDVIRPLVSSTSVFNSFFTTLDKSFHYGGAFVTPLGE
VNVSPDEWWNRDLKTYPFKGRVMGDGWA Amino Acid Sequence: RdhA4$_{BAV1}$ (SEQ ID NO: 29)
(Accession # AY553225)
LGLAGAGLGAVSAVTPVFRDLDELTSSVTAHPKRAWYVKEREFGDIGIEI
DWNILKRRDTRGYSYWNPMIWKQHYPAYDMEAFNKALDNKTKELWPDYAG
PTTRDYSLKNAMYSVGLGCPHYLYNVEQFGVTLPHPAPRPEAIGMPNWAG
TPEENFQMIRAAFSLIGLGPSIGITELDDKSRRFVREYNNCGQHIIFDDN
ITETYRTANPPTIHIPSSHRYVIATHNMGADEILRRAPSTIGACTESISY
ARVAYAKSFVEQFIRGLGYNVVYGHSLQAAPAMDFWSGVGEHARMGQVCV
TPENGAMMRTHAIFFTDLPLSPTKPIDAGITKFCETCGICAESCPVGAVP
AKGVNRNWDSNCDGQSFDNDIESGGTEVMYNVPGYKGWRVDGFRCLADCN
GCKGSCPFNAIPNGSFIHSLVKATTSTTPLFNGFFTQMEKSLHYGKQDKD
PESWWHEPNAWHVYGSNPGLLG Amino Acid Sequence: RdhA5$_{BAV1}$ (SEQ ID NO: 30)
(Accession # AY553226)
LGLAGAGVGAVSAAAPVFHDVDELTAPSGGVQKLPWWVKEREFKDLTVPI
DWQNLPKMEGVFPMQAKPTLSAQERYAMGIPGGSSGTWASPEQAQVLFDY
MKKEFPGWEPGYAGLGDNRTTALFMATKFMRMGMWPGEINMGGNRVNVAK
AISAAGGTAAFTSFLGLRSSETLTPQDFGVPRWEGTPEENLLTLRQVVRF
LGGCDVGAQEMDSDVFKLFHEKSGKKQLVIENVDEAAETPTKLVIPAKAK
YILQWTARQPYESTRRQAGEYEDAAVYWSYQRFPFVGAIIQEFIHALGYT
AVSTHLSGYHSSAVATLTGMGEHCRMSSPILVPKYGVTNRAMWVIMTDMP
LMSTKPIDFGVYDFCKTCGICADACPFGLIEKGDPTWEATQPGSRPGFNG
WRTNTTICPHCPVCQSSCPFNTNGDGSFIHDLVRNTVSTTPIFNSFFANM
EKTMGYGRKDPRDWWNIDDYTYGINTSY Amino Acid Sequence: RdhA6$_{BAV1}$ (SEQ ID NO: 31)
(Accession # AY553227)
GAGIGAATSVMPNFHDLDEVISAASAETSSLSGKSLNNFPWYVKERDFEN
PTIDIDWSILARNDGYNHQGAYWGPVPENGDDKRYPDPADQCLTLPEKRD
LYLAWAKQQFPDWEPGINGHGPTRDEALWFASSTGGIGRYRIPGTQQMMS
TMRLDGSTGGWGYFNQPPAAVWGGKYPRWEGTPEENTLMMRTVCQFFGYS
SIGVMPITSNTKKLFFEKQIPFQFMAGDPGVFGGTGNVQGDVPLPKTPVP
IVWEEVDKGYYNDQKIVIPNKANWVLTMTMPLPEDRFKRSLGWSLDASSM
IAYPQMAFNGGRVQTFLKALGYQGLGGDVAMWGPGGAFGVMSGLSEQGRA
ANEISPKYGSATKGSNRLVCDLPMVPTKPIDAGIHKFCETCGICTTVCPS -continued
NAIQVGPPQWSNNRWDNTPGYLGYRLNWGRCVLCTNCETYCPFFNMTNGS
LIHNVVRSTVAATPVFNSFFRQMEHTFGYGMKDDLNDWWNQSHKPW Amino Acid Sequence: RdhA7$_{BAV1}$ (SEQ ID NO: 32)
(Accession # AY553228)
LGLVGAGAGAAAAVAPVFRDLDDLVASPTATFPRAWWIKERDLWDITTEY
DWKAMSRHDTCETMWIKHSWAKYVGVDKVKEAAASAAAIKKEALETGKPG
MDLRATALGSTSGLYNAPQPYFSYTKTAQGWGGGKSFTGQSTIKGPDVLG
VPKWQGDPDANLRMLRAALRFYGAAQIGVVPYDTNVKNKLTCVREGGMAS
MSDKYIEKWPIPAVDARPFVFEDVEKGYETAEKLVIPDKKELFVVSVIQP
MSREMWRQGSGNLRVATNGHRYSLASVWQTKIQGFLTTLGYQGLGYPTRA
YGSMPTIPGFIFSGLGELGRSNNVCLSPEYGSTHGSFHFLTDLPLTPTKP
IDAGMWRFCKTCAICAENCPSQSISYDKEPSWEITPSKYAPNVPVEYSVP
GKKVFWRDEPSCKQWTESCGYSCGICMGSCVFNVDNASMIHQVVKGTIAT
TSLFNGFMKQADKFFGLGLTPESEWNNWWDMNLPAYAFDTTVGVTDGGYK
AKGLLQQ Amino Acid Sequence: BcvA (SEQ ID NO: 33)
(Accession # AY563562)
MHNFHCTISRRDFMKGLGLAGAGIGAATSVMPNFHDLDEVISAASAETSS
LSGKSLNNFPWYVKERDFENPTIDIDWSILARNDGYNHQGAYWGPVPENG
DDKRYPDPADQCLTLPEKRDLYLAWAKQQFPDWEPGINGHGPTRDEALWF
ASSTGGIGRYRIPGTQQMMSTMRLDGSTGGWGYFNQPPAAVWGGKYPRWE
GTPEENTLMMRTVCQFFGYSSIGVMPITSNTKKLFFEKQIPFQFMAGDPG
VFGGTGNVQFDVPLPKTPVPIVWEEVDKGYYNDQKIVIPNKANWVLTMTM
PLPEDRFKRSLGWSLDASSMIAYPQMAFNGGRVQTFLKALGYQGLGGDVA
MWGPGGAFGVMSGLSEQGRAANEISPKYGSATKGSNRLVCDLPMVPTKPI
DAGIHKFCETCGICTTVCPSNAIQVGPPQWSNNRWDNTPGYLGYRLNWGR
CVLCTNCETYCPFFNMTNGSLIHNVVRSTVAATPVFNSFFRQMEHTFGYG
MKDDLNDWWNQSHKPW The deduced amino acid sequences shown above were aligned with other known reductive dehalogenases isolated from *D. ethenogenes* strain 195 and *Dehalococcoides* sp. strain BAV1. The sequences were aligned using clustalX and/or clustalW (same algorithm for both). The alignments are shown in FIGS. 6A-6D. Identical or similar amino acids highlighted. The alignment indicates that the deduced amino acid sequences of the present invention share some identity with other known reductive dehalogenase and the similarity is generally confined to the two iron-sulfur binding motifs near the C-terminus ((CXXCXXCXXXCP)$_2$). The degree of similarity between the deduced amino acid sequences and other known reductive dehalogenases isolated from *D. ethenogenes* strain 195 and *Dehalococcoides* sp. strain BAV1 is shown in the matrix represented by FIGS. 5A-5D. The degree of similarity matrix was calculated using BLOSUM62 amino acid substitution matrix, Henikoff, S, and Henikoff, J. G. (1992) *Proc. Natl. Acad. Sci. USA* 89: 10915-10919.

Example 5

Detection of bvcA in Other Dechlorinating Cultures

Figure 3:
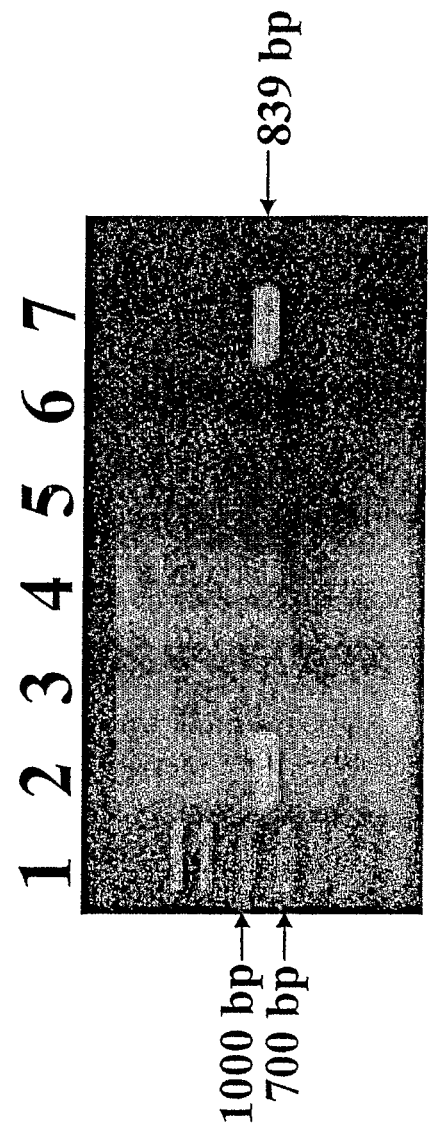
FIG. 3. shows the results of an experiment demonstrating the specificity of primers targeting the VC RDase gene, bvcA.

PCR amplification was performed using bvcA-targeted primers bvcAF and bvcAR (Table 2) using genomic DNA from other *Dehalococcoides* isolates and *Dehalococcoides*-containing mixed cultures as templates. As shown in FIG. 3, the correct sized amplicon was generated with isolate BAV1 genomic DNA, but not with genomic DNA from *Dehalococcoides ethenogenes* strain 195, strain FL2, or strain CBDB1, none of which have been reported to grow on VC (FIG. 3, DNA size marker 50-2000 bp (Biorad Laboratories, Hercules, Calif.) (lane 1); genomic DNA from: strain BAV1 (lane 2), strain CBDB1 (lane 3), *Dehalococcoides ethenogenes* (lane 4), and strain FL2 (lane 5); H$_2$O (lane 6), plasmid DNA containing rdhA6$_{BAV1}$ (lane 7)). bvcA was detected in four of eight *Dehalococcoides*-containing cultures capable of complete reductive dechlorination and ethene production.

Figure 4:
FIG. 4 shows the detection of bvcA in VC-dechlorinating mixed cultures.

As shown in FIG. 4, bvcA was also present in cultures KB-1 and the Bio-Dechlor INOCULUM, two commercially available ethene-producing enrichment cultures that have been successfully used in bioaugmentation approaches. (FIG. 4, DNA size marker 1 Kb plus (Invitrogen™, Carlsbad, Calif.) (lane 1), H$_2$O (lane 2), plasmid DNA containing rdhA6$_{B4V1}$ (lane 3); genomic DNA from the Bachman enrichment culture (lane 4), the Au Sable culture (lane 5), the Pere Marquette culture (lane 6), the Red Cedar culture (lane 7), the Hydrite culture (lane 8), the Minerva culture (lane 9), Bio-Dechlor INOCULUM (lane 10), KB-1 (lane 11), and the Victoria culture (lane 12)). In addition, bvcA was identified in two ethene-producing enrichment cultures derived from chloroethene-contaminated aquifer materials (i.e., the Minerva site and the Hydrite site). bvcA, however, was not detected in the Victoria culture containing *Dehalococcoides* sp. strain VS nor in three VC-dechlorinating enrichment cultures derived from Michigan river sediments (FIG. 4).

Patents, patent applications, publications, product descriptions, and protocols are cited throughout this application, the disclosures of which are incorporated herein by reference in their entireties for all purposes.

What we claims is:

1. A method for identifying a dechlorinating bacterial organism comprising:
   (a) contacting a probe with a bacterial cell extract under high stringency conditions of 0.5×SSC and 65° C., the contact effecting the hybridization of the probe with a nucleic acid obtained from the bacterial cell extract, wherein the probe comprises a sequence selected from the group consisting of SEQ ID NO: 1, SEQ ID NO: 7, SEQ ID NO: 14, SEQ ID NO: 21, SEQ ID NO: 23, SEQ ID NO: 24 and SEQ ID NO: 25, and
   (b) determining that the probe has hybridized to the nucleic acid obtained from the bacterial cell extract.

2. The method of claim 1, wherein the bacterial cell extract is obtained from a bacterial culture or an environmental sample.

3. A method of quantifying the amount of dechlorinating bacteria present in a sample comprising:
   (a) contacting the sample with (i) a probe comprising a portion of an isolated polynucleotide encoding a reductive dehalogenase comprising a polynucleotide sequence of at least 15 nucleotides that has at least 95% sequence identity over the length of the entire reference sequence to a sequence selected from the group consisting of SEQ ID NO: 1 and SEQ ID NO: 7; (ii) a first oligonucleotide primer comprising SEQ ID NO: 14; and (iii) a second oligonucleotide primer comprising SEQ ID NO: 21; and
   (b) performing Real-Time PCR on the sample to quantify the amount of dechlorinating bacteria in the sample.

4. A method of quantifying the amount of dechlorinating bacteria present in a sample comprising:
   (a) contacting the sample with (i) a first oligonucleotide primer comprising the sequence of SEQ ID NO: 23, (ii) a second oligonucleotide primer comprising the sequence of SEQ ID NO: 24 and (iii) a probe comprising the sequence of SEQ ID NO: 25; and
   (b) performing Real-Time PCR on the sample to quantify the amount of dechlorinating bacteria present in the sample.

5. The method of claim 1, wherein the probe comprises the sequence of SEQ ID NO: 1.

6. The method of claim 1, wherein the probe comprises the sequence of SEQ ID NO: 7.

7. The method of claim 1, wherein the probe comprises the sequence of SEQ ID NO: 14.

8. The method of claim 1, wherein the probe comprises the sequence of SEQ ID NO: 21.

9. The method of claim 4, wherein the first oligonucleotide primer has a sequence of SEQ ID NO: 23, the second oligonucleotide primer has a sequence of SEQ ID NO: 24 and the probe has a sequence of SEQ ID NO: 25.

10. A method for identifying a dechlorinating bacterial organism in a sample comprising:
    (a) contacting the sample with (i) a first oligonucleotide primer comprising a sequence selected from the group consisting of SEQ ID NO: 14, SEQ ID NO: 23, and SEQ ID NO: 25; and (ii) a second oligonucleotide primer comprising a sequence selected from the group consisting of SEQ ID NO: 21 and SEQ ID NO: 24; and (b) performing PCR on the sample to determine the presence of the dechlorinating bacterial organism in the sample.

11. The method of claim 10, wherein the first oligonucleotide primer has the sequence of SEQ ID NO: 14 and the second oligonucleotide primer has the sequence of SEQ ID NO: 21.

12. The method of claim 1, wherein the probe comprises the sequence of SEQ ID NO: 23.

13. The method of claim 1, wherein the probe comprises the sequence of SEQ ID NO: 24.

14. The method of claim 1, wherein the probe comprises the sequence of SEQ ID NO: 25.

15. The method of claim 3, wherein the probe comprises a polynucleotide sequence having at least 99% sequence identity over the length of the entire reference sequence to a sequence selected from the group consisting of SEQ ID NO: 1 and SEQ ID NO: 7.

16. The method of claim 10, wherein the first oligonucleotide primer has the sequence of SEQ ID NO: 14 and the second oligonucleotide primer has the sequence of SEQ ID NO: 24.

17. The method of claim 10, wherein the first oligonucleotide primer has the sequence of SEQ ID NO: 23 and the second oligonucleotide primer has the sequence of SEQ ID NO: 21.

18. The method of claim 10, wherein the first oligonucleotide primer has the sequence of SEQ ID NO: 25 and the second oligonucleotide primer has the sequence of SEQ ID NO: 21.

* * * * *

SEQUENCE LISTING

```
<160> NUMBER OF SEQ ID NOS: 63

<210> SEQ ID NO 1
<211> LENGTH: 1551
<212> TYPE: DNA
<213> ORGANISM: Dehalococcoides sp

<400> SEQUENCE: 1
atgcataatt tccattgtac gataagtagg cgagatttta tgaagggatt ggggttagcg      60
ggagcaggga taggtgccgc gacttcagtt atgccgaatt ttcacgactt ggatgaagta     120
atttctgctg ctagtgccga aaccagttct ttgtcgggta aatctcttaa taattttcct     180
tggtatgtga agaaaggga ttttgaaaat cctaccattg atatagattg gtctatactt     240
gcgcgtaatg acggttacaa tcatcaggga gcctattggg gacctgtacc tgaaaatgga     300
gatgataaaa ggtatcctga tcccgcggac cagtgtctta ctctaccaga aagagagat     360 ctttatttag cgtgggcaaa acagcaattt cctgactggg aaccaggaat taatggccat     420
gggccaacaa gggacgaagc tttatggttt gcctcaagta caggtggtat cggtaggtat     480
agaattcctg gtacccagca aatgatgtcc acaatgcgtc ttgacgggtc tactggtggt     540
tggggttatt tcaatcaacc accggcagca gtctggggag ggaaataccc aaggtgggaa     600
ggaactcctg aagagaatac gttgatgatg cgaactgttt gtcaatttt tggttactcc     660 agtataggtg taatgccaat caccagcaat acaaagaagc ttttttttga aaagcaaata     720
cctttccaat ttatggctgg agatcccggt gtatttgggg gaacgggaaa tgtgcagttt     780
gatgtcccgc tgccaaagac acctgttcca atagtctggg aggaagtcga taagggtat     840 tataatgacc agaaaattgt aatacccaat aaggctaact gggtattaac aatgacaatg     900
cctttaccag aagatcgttt taaacgttct ctagggtggt cacttgacgc ttcaagtatg     960
attgcctatc ctcagatggc tttaatgga ggccgagttc agactttttt aaaagcactt    1020
ggctatcaag gacttggtgg cgacgtggct atgtggggac ctggtggtgc ttttggagtt    1080
atgagtggtc tttccgaaca aggtcgtgct gctaatgaaa tcagccccaa atacggttcg    1140
gcaactaagg gctctaatcg attagtttgt gatttgccca tggttccgac caagccaatt    1200
gatgctggca tacacaaatt ctgtgaaacg tgtggcattt gtacaacagt ttgtccctca    1260
aatgctatcc aggtaggtcc tccacaatgg agtaataatc ggtgggataa taccctggt     1320 tatcttggtt atcgacttaa ctggggtaga tgtgttcttt gtacaaactg tgagacctat    1380
tgcccatttt ttaacatgac taatggttct ttgattcata acgtagtcag atccacagtt    1440
gcagctacac cggtttttaa ttcatttttc cgccaaatgg aacatacatt tggatatggt    1500
atgaaagatg atttaaacga ttggtggaat caatcacaca agccttggta a             1551

<210> SEQ ID NO 2
<211> LENGTH: 1393
<212> TYPE: DNA
```

<213> ORGANISM: Dehalococcoides sp

<400> SEQUENCE: 2

| | | | | | |
|---|---|---|---|---|---|
| gggagcaggt | attggtaccg | cagctgcaac | tgcaactgcc | ccaatgtttc | acgaccttga | 60 |
| tgaggtgatc | gcttcaccct | cagcagcaaa | tgaaagacca | tggtgggtaa | aggatagaga | 120 |
| attgtaccag | cccacgcttg | aggtagattg | ggatattatg | actccgccgg | atggcagagt | 180 |
| tagcgggcag | cagactgaaa | cccaaattca | ctaccttgga | agcgaagagg | taaaaaggcg | 240 |
| tttatcatcg | aatataatgt | ctcccaacgt | tgaagccgct | atcaataata | caccggggaa | 300 |
| aactttgcgt | gaccaagcct | tgggactcag | ctcaattgta | ccgatgatga | ttcacggtat | 360 |
| atctttcatg | ggcccgggtc | ttattcctac | ccctgcaaca | accggcgccc | ctaaatggga | 420 |
| gggtacacct | gaagaaaaca | gccggatggt | acgcagtgtt | cttacttttc | tgggtgccgg | 480 |
| tatggttggt | tttggtgaaa | tttccagcca | ggagagagaa | aaaatattct | acacttatca | 540 |
| taaacaagtc | cccaacaaga | ggcaggtatt | tgaggatgta | gatgttggct | acgaaggtac | 600 |
| cgataaatac | gttttccctg | acaggaagct | ttataagata | tctatgtccc | tgcctatgtc | 660 |
| ccgggaaatg | tatcgaactt | ccgacagatc | ttcattacaa | tttgcagcca | atgtatcccg | 720 |
| ttaccgtcac | ttcagtatgc | ttcagccggc | ttttccaagaa | tttatcagag | gtatcgggta | 780 |
| tcattgttat | ggctatcctg | taccacaggc | tggccctatg | cctgcagcag | ttagtgctat | 840 |
| tcttaccggt | ctggcggaat | caagccgaaa | tagcgggtat | tgtatctctc | cggactacgg | 900 |
| accggtttca | ggtttctttta | catttgtaac | tgacttgcca | gttgaaccca | ctacacctat | 960 |
| agatgctggt | atctggcgct | tttgtcagac | ttgcaataag | tgtgcccaaa | actgtccgac | 1020 |
| ccaagtaatc | ccttacgata | aagaaccgag | ttgggaactc | cctacattat | atggtaaacc | 1080 |
| ggatattatc | catccttccg | gcaagcgcat | gttctacgca | aaccatatag | agtgttggat | 1140 |
| gtactgtttt | gaaggcggtt | gcgggacatg | tatggctaca | tgtacttttta | atgtaaatgg | 1200 |
| cgcagccatg | gtacatgatg | tggttaaggc | tacactagcc | acaacttcaa | tgtttaacga | 1260 |
| atttctgtgg | aaagcggata | agaccttcgg | ctatggggtg | aagtctgggg | aagaaaaaga | 1320 |
| agactggtgg | gatttatcct | taccatcgat | gggctgggat | acaacttcct | tctcaaaaca | 1380 |
| tggtggttat | taa | | | | | 1393 |

<210> SEQ ID NO 3
<211> LENGTH: 1462
<212> TYPE: DNA
<213> ORGANISM: Dehalococcoides sp
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (1281)..(1282)
<223> OTHER INFORMATION: n is a, c, g, or t
<220> FEATURE:
<221> NAME/KEY: misc_feature
<222> LOCATION: (1284)..(1285)
<223> OTHER INFORMATION: n is a, c, g, or t

<400> SEQUENCE: 3

| | | | | | |
|---|---|---|---|---|---|
| gggtgctgca | acagcttcag | caccagtgtt | tcatgatttg | gatgaaatga | tnacatctgt | 60 |
| acctaaatct | acaactcaac | atgcttggtg | ggtaaaagaa | agagactatg | aggatattac | 120 |
| tacgcctgtt | gattggactg | tttggtcacg | acgtgaggcc | ttaaagaacc | cgatgccgcc | 180 |
| cggttttgcc | gggaattatg | tgcctaaaga | acaggccaga | ttacagagct | ttcgtaatga | 240 |

```
aattaaaaga ggtataactg aaaaaattcc cggtgcaact ttacgtgatt gggctctttc     300
ggaagctggg cggagcaata ccacctcttc gtcatggatg gggcttgatg ttaaacccccc    360 atggttatgg ggtgaagcct ctgctttacc ggttgaacct tggccagaag gtgcacccaa     420
atgggaatct actccggaag ataatcttag aacggttcag gctgccggac actatttcgg     480
tacgcctcag gtaggcgcca tggaaatcaa tgaacatatg attcgtatgt tcgataaaga     540
tggttttgaa cataactata gtgcaagtta tgagaaaccc atgatgcgat ccgctctga      600 gtggtttgaa gatattccgg ttggttttca ggatgccaat caggtaaaac atattccaaa     660
atcatgtaaa tgggcggtta cttatattgc cgccaaagaa aatgcactgc agatgactta     720
tggcatgcgt actggtgatc ctcaagatcc gtggtataag cgcatctttc ctttgggtta     780
tacaacagga gaggcttatt ccaaagctga ttatgttaaa gtccaattta tgaaattcat     840
aaaaatgttg ggttatcaaa cttattatat gggtttagcc ggtggtacaa gttcaaatag     900
tcctgcagga attttctcag gtttggcaga gaggctcgc cctgcgctgg cctgttcacc      960
ttattatggt aatgcggtac gtcatattgg aatcattgtt accgatatgc tctgagtcc    1020 cactaagcct attgatgccg gtattgttaa tttctgcaaa gtatgcaaaa atgtgcgga    1080 gacttgccct tccggcgcta ttagtatgga aactgaacaa caatgggaac ctgcttgcac    1140
ggggaataat cccggtcgaa aaacttggta ttttggactgg tttaaatgtc gtccatgggg   1200
ttccccatat tattgtccca attgtcaaac agtctgccca tttaacaatc ctaacaaagc    1260
aattatccat aacgctgtac nnannacggc tgccaccact ccaatattta acagcttctt    1320
ttcatctttg gataagagct ttggttatgc tcaccagcgt tcggacgaag agcgacttaa    1380
ctggtggtac agggatctta atacatggca atatgatgat gtttttggta tgggcacaaa    1440
agatccaaaa tcttggttat ga                                             1462
```

<210> SEQ ID NO 4
<211> LENGTH: 1437
<212> TYPE: DNA
<213> ORGANISM: Dehaloccoides sp

<400> SEQUENCE: 4

```
ggagcaggcc taggagcagc tgcgtccact actccggtgt ttcatgacat ggatgaactc      60
attgcttcat ctggttttag tggttcagaa tcatattcca gatatccatg gtgggtcaaa     120
gaagtggata agccgaccgc agagatagac tggaatctta tgaaaccta tgacatgcgt     180 aattcagata aatgggctac cccagaactt cttgccaaat attatgctgc tcaattaaag     240
catactaagg aatgcatact gaataaaacg cccggcagta gtctgaagga ttatgctttg     300
tttgggggta tcaaggggtc catgatgcaa aatgtaccaa aggttggaac ccctgaaccc     360
aatctggaat atctctatcc tacagataca cttacttcac ttggtttacc ccggtatgaa     420
ggcacccctg aggaaaacct taaatgtgt gctgcagcta ttcatctact cggaggccgc     480
gatataagcg ttgtagaggt agatgataat gttaaaaagg tcctttattc gcattctgct     540
atgctaatgg gaggaaagcc gagtagagcc attgtttggg aagacgtaga taatgcgtat     600
gaaacaccag aaaaaatggt aattcccaac aaatgcaaat gggcgttggt gtattcatgc     660
cctcagtctc aattatcaag gtatcgaagt gttatcatgg gcaaatttgg ggtatttgga     720
gcatactctg atatagcagt tatggatcaa cgtctacaaa aattcctgcg tatattggga     780
tatcagggtg tttttggatgg tttcggtggg ggcaatagca taagtagtaa ttcgggcttt    840
```

-continued

| ggggtacttg | caggcagtgg | tgagattggt | agacatgact | acgtaaattc | tcccagtttt | 900 |
| gggccttga | tgcggatgag | tcaatttata | ctaactgact | tacctctagc | acctactaaa | 960 |
| cccattgatg | cgggtatgtg | gaaattctgc | cagtcatgta | agaaatgtgc | cgatatgtgc | 1020 |
| ccatctgggg | ctatctccaa | agaggctgaa | cctacttggg | agcctacggg | agtatggaat | 1080 |
| ggcactggcc | gcaagcttta | tccggtagat | tatcccaagt | gtggcccttg | aggggaatg | 1140 |
| cctcctggag | ggattggcca | tatctatgaa | gcggggcctg | gtggttgttc | taattgccaa | 1200 |
| gtagtatgtg | ttttcaccaa | gactcctaaa | gcttcaatac | atgatgttat | aagaccactt | 1260 |
| gtttccagta | cctcggtctt | taacagtttc | tttactacac | tggataaatc | attccattac | 1320 |
| gggggggcat | ttgttactcc | gctgggagaa | gttaatgtaa | gccctgatga | atggtggaac | 1380 |
| cgtgatctga | aaacttatcc | gttcaaaggc | agagttatgg | gagacggttg | ggcatag | 1437 |

<210> SEQ ID NO 5
<211> LENGTH: 1432
<212> TYPE: DNA
<213> ORGANISM: Dehalococcoides sp

<400> SEQUENCE: 5

| ttttatgaag | ggcttggggt | tagctggtgc | gggacttggt | gccgtgtcgg | ctgttacgcc | 60 |
| tgtctttaga | gatttggatg | aactaacgtc | ttcagttacg | gcacatccta | aacgtgcctg | 120 |
| gtatgtaaag | gaacgagaat | ttgggggatat | cggtatagaa | attgactgga | atattttgaa | 180 |
| acgccgtgac | acccgaggtt | attcatattg | gaatccgatg | atttggaagc | aacattatcc | 240 |
| ggcttacgat | atggaagctt | ttaataaagc | tttagacaat | aagaccaaag | aactctggcc | 300 |
| tgattatgca | gggccgacta | ccagagacta | ttccctgaaa | aatgccatgt | attcggtcgg | 360 |
| gttgggatgc | cctcattacc | tgtacaatgt | agaacagttt | ggagtgacac | ttccgcatcc | 420 |
| tgcaccacgc | ccggaagcaa | ttggtatgcc | caattgggcg | ggtactcctg | aagaaaattt | 480 |
| ccagatgatt | cgggctgctt | ttagtcttat | cggtttaggt | ccttcaatag | gtataaccga | 540 |
| actggatgat | aagagtaggc | gttttgttcg | ggaatataat | aactgtggtc | aacacataat | 600 |
| atttgatgac | aatataactg | aaacatatcg | gacggcaaat | cctcccacca | ttcatattcc | 660 |
| ttcttcacac | cggtatgtta | tagctaccca | caatatgggg | gcagacgaga | tacttcgccg | 720 |
| tgctcccctca | accattggtg | catgcacaga | gtccatatcc | tatgcccgtg | tagcgtatgc | 780 |
| caagagtttc | gttgaacaat | ttatccgcgg | acttggctat | aacgtcgtct | atggtcattc | 840 |
| acttcaggct | gcaccagcta | tggatttctg | gagtggagta | ggtgagcatg | cccgtatggg | 900 |
| gcaggtttgt | gtgacacctg | agaatggtgc | catgatgcgt | acccatgcca | tcttcttcac | 960 |
| cgatttacca | ctctcgccta | caaaaccaat | tgatgctggc | attactaagt | tttgcgaaac | 1020 |
| ttgcggtatc | tgtgcagaga | gctgtccggt | aggagccgtt | ccggctaaag | gagtgaaccg | 1080 |
| gaattgggat | tctaactgtg | acggccgag | ctttgataat | gatatcgaaa | gcggcggcac | 1140 |
| cgaggtaatg | tacaatgtac | ccggctataa | aggctggagg | gttgacgggt | ttagatgctt | 1200 |
| agctgattgc | aatggatgca | agggttcctg | ccctttcaat | gctattccta | acgggagctt | 1260 |
| catccacagt | ctagttaaag | caaccacttc | aactaccccg | ctgttcaatg | gtttctttac | 1320 |
| ccaaatggaa | aaatctctcc | attacggtaa | acaggataaa | gaccctgaat | cctggtggca | 1380 |
| tgaaccaaac | gcctggcacg | tgtatggcag | taatccgggg | ttactgggtt | aa | 1432 |

<210> SEQ ID NO 6
<211> LENGTH: 1451

<212> TYPE: DNA
<213> ORGANISM: Dehalococcoides sp

<400> SEQUENCE: 6

```
attttatgaa ggcttttgggt ctggctggtg ccggagtcgg agcagtgtct gctgccgccc      60
cggttttttca tgatgtggat gagctgactg ctccttccgg cggcgtacag aagctgccgt     120
ggtgggttaa agagagggag ttcaaagatc ttacagtacc cattgactgg cagaatctgc     180
ccaagatgga gggtgttttc cccatgcagg ccaagccaac cctgtcggct caggaaagat     240
atgccatggg cattcccggc ggcagttcgg gtacttgggc cagccctgag caggcgcaag     300
tacttttttga ttacatgaaa aaggaatttc cgggatggga acccggctat gccggtctgg     360
gagacaaccg gacaaccgct ctcttcatgg ccaccaaatt tatgcgtatg gcatgtggc      420
ccggtgaaat aaacatgggc ggcaacaggg ttaatgttgc caaggctatt tcagcggccg     480
gaggcacggc tgctttcacc tcattcctgg gtcttcgctc aagcgaaacg ctccgcccgc     540
aggatttcgg tgtaccgcgt tgggaaggca cacctgaaga aatctgctt accttgcgtc      600
aggtagtccg tttccttggc ggctgtgatg taggtgctca ggaaatggat tcagatgttt     660
tcaagctttt ccatgagaaa agcggcaaga aacagctggt aatagaaaac gtagacgaag     720
cggctgaaac acccaccaaa ctggtcattc ctgccaaagc caaatatatc ctccagtgga     780
ctgcccgcca gccttacgaa tccaccagac gccaggccgg cgaatatgag gatgccgctg     840
tatactggtc ttatcagagg ttccccttttg tcggggctat tatccaggaa tttatccacg     900
ctctgggata tactgcggtt tcaacccatc tgtctggtta ccattccagt gctgtagcga     960
ccttgaccgg tatgggggaa cattgccgta tgtcatcacc catcttggtt cccaaatacg    1020
gcgttaccaa ccgggctatg tgggtaatta tgaccgatat gcctcttatg tccactaagc    1080
ctatagactt tggggtgtat gacttctgca agacctgcgg tatctgtgcg gacgcctgcc    1140
cgttcggctt gattgaaaaa ggcgacccga cctgggaagc tactcagccg ggtagccgtc    1200
ccggtttcaa cggatggcgt actaataccc ccatctgtcc gcattgtccg gtctgtcaaa    1260
gcagttgccc cttttaatacc aatggcgacg gttcttttat acatgatttg gtcagaaaca    1320
cagtttctac caccccctatt ttcaacagtt tctttgccaa tatggaaaag accatgggat    1380
acggacgcaa ggacccgcgc gactggtgga atatagatga ttataccctac ggtataaata    1440
catcttacta a                                                          1451
```

<210> SEQ ID NO 7
<211> LENGTH: 1504
<212> TYPE: DNA
<213> ORGANISM: Dehalococcoides sp

<400> SEQUENCE: 7

```
attggggtta gcgggagcag ggataggtgc cgcgacttca gttatgccga attttcacga      60
cttggatgaa gtaatttctg ctgctagtgc cgaaaccagt tctttgtcgg gtaaatctct     120
taataatttt ccttggtatg tgaaagaaag ggattttgaa aatcctacca ttgatataga     180
ttggtctata cttgcgcgta atgacggtta caatcatcag ggagcctatt ggggaccctgt    240
acctgaaaat ggagatgata aaaggtatcc tgatcccgcg gaccagtgtc ttactctacc    300
agaaaagaga gatctttatt tagcgtgggc aaaacagcaa tttcctgact gggaaccagg    360
aattaatggc catgggccaa caagggacga agctttatgg tttgcctcaa gtacaggtgg    420
tatcggtagg tatagaattc ctggtaccca gcaaatgatg tccacaatgc gtcttgacgg    480
```

```
gtctactggt ggttggggtt atttcaatca accaccggca gcagtctggg gagggaaata      540
cccaaggtgg gaaggaactc ctgaagagaa tacgttgatg atgcgaactg tttgtcaatt      600
ttttggttac tccagtatag gtgtaatgcc aatcaccagc aatacaaaga agctttttttt    660 tgaaaagcaa ataccttttcc aatttatggc tggagatccc ggtgtatttg ggggaacggg    720
aaatgtgcag tttgatgtcc cgctgccaaa gacacctgtt ccaatagtct gggaggaagt    780
cgataaaggg tattataatg accagaaaat tgtaatacccc aataaggcta actgggtatt    840
aacaatgaca atgcctttac cagaagatcg ttttaaacgt tctctagggt ggtcacttga    900
cgcttcaagt atgattgcct atcctcagat ggcttttaat ggaggccgag ttcagacttt    960
tttaaaagca cttggctatc aaggacttgg tggcgacgtg gctatgtggg gacctggtgg   1020 tgctttttgga gttatgagtg gtctttccga acaaggtcgt gctgctaatg aaatcagccc    1080
caaatacggt tcggcaacta agggctctaa tcgattagtt tgtgatttgc ccatggttcc    1140
gaccaagcca attgatgctg gcatacacaa attctgtgaa acgtgtggca tttgtacaac    1200
agtttgtccc tcaaatgcta tccaggtagg tcctccacaa tggagtaata tcggtgggga    1260
taatacccct ggttatcttg gttatcgact taactgggggt agatgtgttc tttgtacaaa    1320
ctgtgagacc tattgcccat tttttaacat gactaatggt tctttgattc ataacgtagt    1380
cagatccaca gttgcagcta caccggtttt taattcattt ttccgccaaa tggaacatac    1440
atttggatat ggtatgaaag atgatttaaa cgattggtgg aatcaatcac acaagccttg    1500
gtaa                                                                  1504

<210> SEQ ID NO 8
<211> LENGTH: 1533
<212> TYPE: DNA
<213> ORGANISM: Dehalococcoides sp

<400> SEQUENCE: 8
atgaaggcac tcggtcttgt aggggctggt gcgggtgcgg cagcagctgt tgctccggtg      60
ttcagagacc tagatgattt agtcgcttcc cccactgcaa cttttcccgcg tgcttggtgg   120 attaaggaac gtgaccctgtg ggatattacc accgaatatg actggaaagc tatgtcccgg    180
catgatacat gtgaaaccat gtggataaaa cattcatggg caaaatatgt aggtgttgac    240
aaggttaaag aagctgccgc cagtgcagcc gcaatcaaaa aagaagctct ggaaactggt    300
aaaccgggca tggacttaag agcaactgcc ctgggtagta cctctggtttt gtataatgct    360 cctcaaccgt atttctcata tactaaaact gctcagggtt ggggtggtgg taagagtttc    420
accggtcaat ctaccataaa agggcctgat gtactgggag tacccaagtg gcagggtgat    480
cctgatgcta acctcaggat gttgcgagcg gctttacgct tctatggcgc tgcccagatt    540
ggcgtagttc cctacgatac aaatgtaaag aataaattaa cctgtgttcg cgaaggtggc    600
atggcctcta tgagcgataa atacattgaa aaatggccta cccgctgtgt agatgcccgt    660
ccgtttgtgt tcgaagatgt tgaaaaaggc tatgaaaccg ctgaaaagct ggtgattccg    720
gacaaaaagg aacttttttgt ggtttcagtt attcagccta tgagccgcga aatgtggcga    780
cagggtagcg gcaatttgag agtggcaact aatggtcacc gttatagtct ggcatctgtt    840
tggcaaacca aaattcaagg cttcctgacg acccttggtt atcagggttt gggttatcct    900
accagggctt atggatccat gcctactatt cctgggttta ttttctctgg tttaggtgaa    960
cttgggcgtt caaataatgt ctgtttgagc cctgaatacg gttcaaccca cggatcattc   1020
catttcctga cagatttgcc gttaactcct accaaaccta tagatgccgg tatgtggcgg   1080
```

```
ttctgtaaga cttgtgctat ttgcgctgaa aactgtcctt cgcagtctat ttcatatgac    1140
aaagaaccct catgggaaat cactccttcc aagtatgctc ccaatgttcc ggtagaatac    1200
agtgttccgg gcaaaaaggt tttctggcgt gatgaaccat cttgcaaaca gtggactgag    1260
agttgtggtt attcctgtgg tatctgcatg ggttcctgcg tgttcaacgt ggacaatgcc    1320
tccatgatac accaggtagt taaaggtact attgctacca ccagtctctt caatggtttc    1380
atgaaacagg ctgacaagtt ctttggttat ggacttacac tgagtctga gtggaacaat    1440 tggtgggaca tgaatctgcc ggcctatgct tttgatacta ctgttggtgt tactgatggt    1500
ggttacaaag ccaaaggcct gctgcagcaa taa                                 1533
```

<210> SEQ ID NO 9
<211> LENGTH: 19
<212> TYPE: DNA
<213> ORGANISM: artificial
<220> FEATURE:
<223> OTHER INFORMATION: primer

<400> SEQUENCE: 9
gtaccgatga tgattcacg                                                   19

<210> SEQ ID NO 10
<211> LENGTH: 17
<212> TYPE: DNA
<213> ORGANISM: artificial
<220> FEATURE:
<223> OTHER INFORMATION: primer

<400> SEQUENCE: 10
tgcaagcagg ttcccat                                                     17

<210> SEQ ID NO 11
<211> LENGTH: 18
<212> TYPE: DNA
<213> ORGANISM: artificial
<220> FEATURE:
<223> OTHER INFORMATION: primer

<400> SEQUENCE: 11
gattatgctt tgtttggg                                                    18

<210> SEQ ID NO 12
<211> LENGTH: 17
<212> TYPE: DNA
<213> ORGANISM: artificial
<220> FEATURE:
<223> OTHER INFORMATION: primer

<400> SEQUENCE: 12
atgccatgta ttcggtc                                                     17

<210> SEQ ID NO 13
<211> LENGTH: 18
<212> TYPE: DNA
<213> ORGANISM: artificial
<220> FEATURE:
<223> OTHER INFORMATION: primer

<400> SEQUENCE: 13
gttaatgttg ccaaggct                                                    18

<210> SEQ ID NO 14

-continued

```
<211> LENGTH: 19
<212> TYPE: DNA
<213> ORGANISM: artificial
<220> FEATURE:
<223> OTHER INFORMATION: primer

<400> SEQUENCE: 14
tgcctcaagt acaggtggt                                                19

<210> SEQ ID NO 15
<211> LENGTH: 16
<212> TYPE: DNA
<213> ORGANISM: artificial
<220> FEATURE:
<223> OTHER INFORMATION: primer

<400> SEQUENCE: 15
aaactgctca gggttg                                                   16

<210> SEQ ID NO 16
<211> LENGTH: 19
<212> TYPE: DNA
<213> ORGANISM: artificial
<220> FEATURE:
<223> OTHER INFORMATION: primer

<400> SEQUENCE: 16
agccatacat gtcccgcaa                                                19

<210> SEQ ID NO 17
<211> LENGTH: 17
<212> TYPE: DNA
<213> ORGANISM: artificial
<220> FEATURE:
<223> OTHER INFORMATION: primer

<400> SEQUENCE: 17
ggcttgatgt taaaccc                                                  17

<210> SEQ ID NO 18
<211> LENGTH: 18
<212> TYPE: DNA
<213> ORGANISM: artificial
<220> FEATURE:
<223> OTHER INFORMATION: primer

<400> SEQUENCE: 18
ttagaacaac caccaggc                                                 18

<210> SEQ ID NO 19
<211> LENGTH: 18
<212> TYPE: DNA
<213> ORGANISM: artificial
<220> FEATURE:
<223> OTHER INFORMATION: primer

<400> SEQUENCE: 19
tcaaccctcc agccttta                                                 18

<210> SEQ ID NO 20
<211> LENGTH: 21
<212> TYPE: DNA
<213> ORGANISM: artificial
<220> FEATURE:
<223> OTHER INFORMATION: primer

<400> SEQUENCE: 20
```

-continued catggtcttt tccatattgg c                                                21

<210> SEQ ID NO 21
<211> LENGTH: 18
<212> TYPE: DNA
<213> ORGANISM: artificial
<220> FEATURE:
<223> OTHER INFORMATION: primer

<400> SEQUENCE: 21
attgtggagg acctacct                                                    18

<210> SEQ ID NO 22
<211> LENGTH: 17
<212> TYPE: DNA
<213> ORGANISM: artificial
<220> FEATURE:
<223> OTHER INFORMATION: primer

<400> SEQUENCE: 22
ttgcccggaa cactgta                                                     17

<210> SEQ ID NO 23
<211> LENGTH: 23
<212> TYPE: DNA
<213> ORGANISM: artificial
<220> FEATURE:
<223> OTHER INFORMATION: forward primer

<400> SEQUENCE: 23
aaaagcactt ggctatcaag gac                                              23

<210> SEQ ID NO 24
<211> LENGTH: 19
<212> TYPE: DNA
<213> ORGANISM: artificial
<220> FEATURE:
<223> OTHER INFORMATION: reverse primer

<400> SEQUENCE: 24
ccaaaagcac caccaggtc                                                   19

<210> SEQ ID NO 25
<211> LENGTH: 22
<212> TYPE: DNA
<213> ORGANISM: artificial
<220> FEATURE:
<223> OTHER INFORMATION: primer

<400> SEQUENCE: 25
tggtggcgac gtggctatgt gg                                               22

<210> SEQ ID NO 26
<211> LENGTH: 462
<212> TYPE: PRT
<213> ORGANISM: Dehalococcoides sp

<400> SEQUENCE: 26

Gly Ala Gly Ile Gly Thr Ala Ala Thr Ala Thr Ala Pro Met Phe
1               5                   10                  15

His Asp Leu Asp Glu Val Ile Ala Ser Pro Ser Ala Ala Asn Glu Arg
            20                  25                  30

Pro Trp Trp Val Lys Asp Arg Glu Leu Tyr Gln Pro Thr Leu Glu Val
        35                  40                  45

```
Asp Trp Asp Ile Met Thr Pro Pro Asp Gly Arg Val Ser Gly Gln Gln
     50                  55                  60
Thr Glu Thr Gln Ile His Tyr Leu Gly Ser Glu Val Lys Arg Arg
 65                  70                  75                  80
Leu Ser Ser Asn Ile Met Ser Pro Asn Val Glu Ala Ile Asn Asn
                     85                  90                  95
Thr Pro Gly Lys Thr Leu Arg Asp Gln Ala Leu Gly Leu Ser Ser Ile
                100                 105                 110
Val Pro Met Met Ile His Gly Ile Ser Phe Met Gly Pro Gly Leu Ile
            115                 120                 125
Pro Thr Pro Ala Thr Thr Gly Ala Pro Lys Trp Glu Gly Thr Pro Glu
        130                 135                 140
Glu Asn Ser Arg Met Val Arg Ser Val Leu Thr Phe Leu Gly Ala Gly
145                 150                 155                 160
Met Val Gly Phe Gly Glu Ile Ser Ser Gln Glu Arg Glu Lys Ile Phe
                165                 170                 175
Tyr Thr Tyr His Lys Gln Val Pro Asn Lys Arg Gln Val Phe Glu Asp
                180                 185                 190
Val Asp Val Gly Tyr Glu Gly Thr Asp Lys Tyr Val Phe Pro Asp Arg
            195                 200                 205
Lys Leu Tyr Lys Ile Ser Met Ser Leu Pro Met Ser Arg Glu Met Tyr
        210                 215                 220
Arg Thr Ser Asp Arg Ser Ser Leu Gln Phe Ala Ala Asn Val Ser Arg
225                 230                 235                 240
Tyr Arg His Phe Ser Met Leu Gln Pro Ala Phe Gln Glu Phe Ile Arg
                245                 250                 255
Gly Ile Gly Tyr His Cys Tyr Gly Tyr Pro Val Pro Gln Ala Gly Pro
                260                 265                 270
Met Pro Ala Ala Val Ser Ala Ile Leu Thr Gly Leu Ala Glu Ser Ser
        275                 280                 285
Arg Asn Ser Gly Tyr Cys Ile Ser Pro Asp Tyr Gly Pro Val Ser Gly
        290                 295                 300
Phe Phe Thr Phe Val Thr Asp Leu Pro Val Glu Pro Thr Thr Pro Ile
305                 310                 315                 320
Asp Ala Gly Ile Trp Arg Phe Cys Gln Thr Cys Asn Lys Cys Ala Gln
                325                 330                 335
Asn Cys Pro Thr Gln Val Ile Pro Tyr Asp Lys Glu Pro Ser Trp Glu
                340                 345                 350
Leu Pro Thr Leu Tyr Gly Lys Pro Asp Ile Ile His Pro Ser Gly Lys
        355                 360                 365
Arg Met Phe Tyr Ala Asn His Ile Glu Cys Trp Met Tyr Cys Phe Glu
        370                 375                 380
Gly Gly Cys Gly Thr Cys Met Ala Thr Cys Thr Phe Asn Val Asn Gly
385                 390                 395                 400
Ala Ala Met Val His Asp Val Val Lys Ala Thr Leu Ala Thr Thr Ser
                405                 410                 415
Met Phe Asn Glu Phe Leu Trp Lys Ala Asp Lys Thr Phe Gly Tyr Gly
                420                 425                 430
Val Lys Ser Gly Glu Glu Lys Glu Asp Trp Trp Asp Leu Ser Leu Pro
            435                 440                 445
Ser Met Gly Trp Asp Thr Thr Ser Phe Ser Lys His Gly Tyr
        450                 455                 460
```

<210> SEQ ID NO 27
<211> LENGTH: 485
<212> TYPE: PRT
<213> ORGANISM: Dehalococcoides sp.
<220> FEATURE:
<221> NAME/KEY: MISC_FEATURE
<223> OTHER INFORMATION: Xaa is any amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (427)..(428)
<223> OTHER INFORMATION: Xaa can be any naturally occurring amino acid

<400> SEQUENCE: 27

Gly Ala Ala Thr Ala Ser Ala Pro Val Phe His Asp Leu Asp Glu Met
1               5                   10                  15

Xaa Thr Ser Val Pro Lys Ser Thr Thr Gln His Ala Trp Trp Val Lys
            20                  25                  30

Glu Arg Asp Tyr Glu Asp Ile Thr Thr Pro Val Asp Trp Thr Val Trp
        35                  40                  45

Ser Arg Arg Glu Ala Leu Lys Asn Pro Met Pro Pro Gly Phe Ala Gly
    50                  55                  60

Asn Tyr Val Pro Lys Glu Gln Ala Arg Leu Gln Ser Phe Arg Asn Glu
65                  70                  75                  80

Ile Lys Arg Gly Ile Thr Glu Lys Ile Pro Gly Ala Thr Leu Arg Asp
                85                  90                  95

Trp Ala Leu Ser Glu Ala Gly Arg Ser Asn Thr Thr Ser Ser Ser Trp
            100                 105                 110

Met Gly Leu Asp Val Lys Pro Pro Trp Leu Trp Gly Glu Ala Ser Ala
        115                 120                 125

Leu Pro Val Glu Pro Trp Pro Glu Gly Ala Pro Lys Trp Glu Ser Thr
    130                 135                 140

Pro Glu Asp Asn Leu Arg Thr Val Gln Ala Ala Gly His Tyr Phe Gly
145                 150                 155                 160

Thr Pro Gln Val Gly Ala Met Glu Ile Asn Glu His Met Ile Arg Met
                165                 170                 175

Phe Asp Lys Asp Gly Phe Glu His Asn Tyr Ser Ala Ser Tyr Glu Lys
            180                 185                 190

Pro Met Met Arg Phe Arg Ser Glu Trp Phe Glu Asp Ile Pro Val Gly
        195                 200                 205

Phe Gln Asp Ala Asn Gln Val Lys His Ile Pro Lys Ser Cys Lys Trp
    210                 215                 220

Ala Val Thr Tyr Ile Ala Ala Lys Glu Asn Ala Leu Gln Met Thr Tyr
225                 230                 235                 240

Gly Met Arg Thr Gly Asp Pro Gln Asp Pro Trp Tyr Lys Arg Ile Phe
                245                 250                 255

Pro Leu Gly Tyr Thr Thr Gly Glu Ala Tyr Ser Lys Ala Asp Tyr Val
            260                 265                 270

Lys Val Gln Phe Met Lys Phe Ile Lys Met Leu Gly Tyr Gln Thr Tyr
        275                 280                 285

Tyr Met Gly Leu Ala Gly Gly Thr Ser Asn Ser Pro Ala Gly Ile
    290                 295                 300

Phe Ser Gly Leu Ala Glu Glu Ala Arg Pro Ala Leu Ala Cys Ser Pro
305                 310                 315                 320

```
Tyr Tyr Gly Asn Ala Val Arg His Ile Gly Ile Ile Val Thr Asp Met
                325                 330                 335

Pro Leu Ser Pro Thr Lys Pro Ile Asp Ala Gly Ile Val Asn Phe Cys
            340                 345                 350

Lys Val Cys Lys Lys Cys Ala Glu Thr Cys Pro Ser Gly Ala Ile Ser
        355                 360                 365

Met Glu Thr Glu Gln Gln Trp Glu Pro Ala Cys Thr Gly Asn Asn Pro
    370                 375                 380

Gly Arg Lys Thr Trp Tyr Leu Asp Trp Phe Lys Cys Arg Pro Trp Gly
385                 390                 395                 400

Ser Pro Tyr Tyr Cys Pro Asn Cys Gln Thr Val Cys Pro Phe Asn Asn
                405                 410                 415

Pro Asn Lys Ala Ile Ile His Asn Ala Val Xaa Xaa Thr Ala Ala Thr
            420                 425                 430

Thr Pro Ile Phe Asn Ser Phe Phe Ser Ser Leu Asp Lys Ser Phe Gly
        435                 440                 445

Tyr Ala His Gln Arg Ser Asp Glu Glu Arg Leu Asn Trp Tyr Arg Asp
    450                 455                 460

Leu Asn Thr Trp Gln Tyr Asp Asp Val Phe Gly Met Gly Thr Lys Asp
465                 470                 475                 480

Pro Lys Ser Trp Leu
                485

<210> SEQ ID NO 28
<211> LENGTH: 478
<212> TYPE: PRT
<213> ORGANISM: Dehalococcoides sp.

<400> SEQUENCE: 28

Gly Ala Gly Leu Gly Ala Ala Ser Thr Thr Pro Val Phe His Asp
1               5                   10                  15

Met Asp Glu Leu Ile Ala Ser Ser Gly Phe Ser Gly Ser Glu Ser Tyr
            20                  25                  30

Ser Arg Tyr Pro Trp Trp Val Lys Glu Val Asp Lys Pro Thr Ala Glu
        35                  40                  45

Ile Asp Trp Asn Leu Met Lys Pro Tyr Asp Met Arg Asn Ser Asp Lys
    50                  55                  60

Trp Ala Thr Pro Glu Leu Leu Ala Lys Tyr Tyr Ala Ala Gln Leu Lys
65                  70                  75                  80

His Thr Lys Glu Cys Ile Leu Asn Lys Thr Pro Gly Ser Ser Leu Lys
                85                  90                  95

Asp Tyr Ala Leu Phe Gly Gly Ile Lys Gly Ser Met Met Gln Asn Val
            100                 105                 110

Pro Lys Val Gly Thr Pro Glu Pro Asn Leu Glu Tyr Leu Tyr Pro Thr
        115                 120                 125

Asp Thr Leu Thr Ser Leu Gly Leu Pro Arg Tyr Glu Gly Thr Pro Glu
    130                 135                 140

Glu Asn Leu Lys Met Cys Ala Ala Ile His Leu Leu Gly Gly Arg
145                 150                 155                 160

Asp Ile Ser Val Val Glu Val Asp Asn Val Lys Lys Val Leu Tyr
                165                 170                 175

Ser His Ser Ala Met Leu Met Gly Gly Lys Pro Ser Arg Ala Ile Val
            180                 185                 190

Trp Glu Asp Val Asp Asn Ala Tyr Glu Thr Pro Glu Lys Met Val Ile
        195                 200                 205
```

```
Pro Asn Lys Cys Lys Trp Ala Leu Val Tyr Ser Cys Pro Gln Ser Gln
    210                 215                 220

Leu Ser Arg Tyr Arg Ser Val Ile Met Gly Lys Phe Gly Val Phe Gly
225                 230                 235                 240

Ala Tyr Ser Asp Ile Ala Val Met Asp Gln Arg Leu Gln Lys Phe Leu
                245                 250                 255

Arg Ile Leu Gly Tyr Gln Gly Val Leu Asp Gly Phe Gly Gly Gly Asn
                260                 265                 270

Ser Ile Ser Ser Asn Ser Gly Phe Gly Val Leu Ala Gly Ser Gly Glu
            275                 280                 285

Ile Gly Arg His Asp Tyr Val Asn Ser Pro Ser Phe Gly Ala Leu Met
290                 295                 300

Arg Met Ser Gln Phe Ile Leu Thr Asp Leu Pro Leu Ala Pro Thr Lys
305                 310                 315                 320

Pro Ile Asp Ala Gly Met Trp Lys Phe Cys Gln Ser Cys Lys Lys Cys
                325                 330                 335

Ala Asp Met Cys Pro Ser Gly Ala Ile Ser Lys Glu Ala Glu Pro Thr
                340                 345                 350

Trp Glu Pro Thr Gly Val Trp Asn Gly Thr Gly Arg Lys Leu Tyr Pro
            355                 360                 365

Val Asp Tyr Pro Lys Cys Gly Pro Trp Arg Gly Met Pro Pro Gly Gly
370                 375                 380

Ile Gly His Ile Tyr Glu Ala Gly Pro Gly Gly Cys Ser Asn Cys Gln
385                 390                 395                 400

Val Val Cys Val Phe Thr Lys Thr Pro Lys Ala Ser Ile His Asp Val
                405                 410                 415

Ile Arg Pro Leu Val Ser Ser Thr Ser Val Phe Asn Ser Phe Phe Thr
                420                 425                 430

Thr Leu Asp Lys Ser Phe His Tyr Gly Gly Ala Phe Val Thr Pro Leu
                435                 440                 445

Gly Glu Val Asn Val Ser Pro Asp Glu Trp Trp Asn Arg Asp Leu Lys
450                 455                 460

Thr Tyr Pro Phe Lys Gly Arg Val Met Gly Asp Gly Trp Ala
465                 470                 475

<210> SEQ ID NO 29
<211> LENGTH: 472
<212> TYPE: PRT
<213> ORGANISM: Dehalococcoides sp.

<400> SEQUENCE: 29

Leu Gly Leu Ala Gly Ala Gly Leu Gly Ala Val Ser Ala Val Thr Pro
1               5                   10                  15

Val Phe Arg Asp Leu Asp Glu Leu Thr Ser Ser Val Thr Ala His Pro
                20                  25                  30

Lys Arg Ala Trp Tyr Val Lys Glu Arg Glu Phe Gly Asp Ile Gly Ile
            35                  40                  45

Glu Ile Asp Trp Asn Ile Leu Lys Arg Arg Asp Thr Arg Gly Tyr Ser
    50                  55                  60

Tyr Trp Asn Pro Met Ile Trp Lys Gln His Tyr Pro Ala Tyr Asp Met
65                  70                  75                  80

Glu Ala Phe Asn Lys Ala Leu Asp Asn Lys Thr Lys Glu Leu Trp Pro
                85                  90                  95

Asp Tyr Ala Gly Pro Thr Thr Arg Asp Tyr Ser Leu Lys Asn Ala Met
```

|       |       |       |       |       | 100   |       |       |       |       | 105   |       |       |       |       | 110   |       |       |
|-------|-------|-------|-------|-------|-------|-------|-------|-------|-------|-------|-------|-------|-------|-------|-------|-------|-------|

Tyr Ser Val Gly Leu Gly Cys Pro His Tyr Leu Tyr Asn Val Glu Gln
              115                     120                 125

Phe Gly Val Thr Leu Pro His Pro Ala Pro Arg Pro Glu Ala Ile Gly
              130                     135                 140

Met Pro Asn Trp Ala Gly Thr Pro Glu Glu Asn Phe Gln Met Ile Arg
145                     150                     155                 160

Ala Ala Phe Ser Leu Ile Gly Leu Gly Pro Ser Ile Gly Ile Thr Glu
                  165                     170                 175

Leu Asp Asp Lys Ser Arg Arg Phe Val Arg Glu Tyr Asn Asn Cys Gly
              180                     185                 190

Gln His Ile Ile Phe Asp Asp Asn Ile Thr Glu Thr Tyr Arg Thr Ala
              195                     200                 205

Asn Pro Pro Thr Ile His Ile Pro Ser Ser His Arg Tyr Val Ile Ala
              210                     215                 220

Thr His Asn Met Gly Ala Asp Glu Ile Leu Arg Arg Ala Pro Ser Thr
225                     230                     235                 240

Ile Gly Ala Cys Thr Glu Ser Ile Ser Tyr Ala Arg Val Ala Tyr Ala
                  245                     250                 255

Lys Ser Phe Val Glu Gln Phe Ile Arg Gly Leu Gly Tyr Asn Val Val
                  260                     265                 270

Tyr Gly His Ser Leu Gln Ala Ala Pro Ala Met Asp Phe Trp Ser Gly
                  275                     280                 285

Val Gly Glu His Ala Arg Met Gly Gln Val Cys Val Thr Pro Glu Asn
              290                     295                 300

Gly Ala Met Met Arg Thr His Ala Ile Phe Phe Thr Asp Leu Pro Leu
305                     310                     315                 320

Ser Pro Thr Lys Pro Ile Asp Ala Gly Ile Thr Lys Phe Cys Glu Thr
                  325                     330                 335

Cys Gly Ile Cys Ala Glu Ser Cys Pro Val Gly Ala Val Pro Ala Lys
                  340                     345                 350

Gly Val Asn Arg Asn Trp Asp Ser Asn Cys Asp Gly Gln Ser Phe Asp
                  355                     360                 365

Asn Asp Ile Glu Ser Gly Gly Thr Glu Val Met Tyr Asn Val Pro Gly
              370                     375                 380

Tyr Lys Gly Trp Arg Val Asp Gly Phe Arg Cys Leu Ala Asp Cys Asn
385                     390                     395                 400

Gly Cys Lys Gly Ser Cys Pro Phe Asn Ala Ile Pro Asn Gly Ser Phe
                  405                     410                 415

Ile His Ser Leu Val Lys Ala Thr Thr Ser Thr Thr Pro Leu Phe Asn
                  420                     425                 430

Gly Phe Phe Thr Gln Met Glu Lys Ser Leu His Tyr Gly Lys Gln Asp
                  435                     440                 445

Lys Asp Pro Glu Ser Trp Trp His Glu Pro Asn Ala Trp His Val Tyr
              450                     455                 460

Gly Ser Asn Pro Gly Leu Leu Gly
465                     470

<210> SEQ ID NO 30
<211> LENGTH: 478
<212> TYPE: PRT
<213> ORGANISM: Dehalococcoides sp.

<400> SEQUENCE: 30

```
Leu Gly Leu Ala Gly Ala Gly Val Gly Val Ser Ala Ala Ala Pro
1               5                   10                  15

Val Phe His Asp Val Asp Glu Leu Thr Ala Pro Ser Gly Gly Val Gln
            20                  25                  30

Lys Leu Pro Trp Trp Val Lys Glu Arg Glu Phe Lys Asp Leu Thr Val
            35                  40                  45

Pro Ile Asp Trp Gln Asn Leu Pro Lys Met Glu Gly Val Phe Pro Met
        50                  55                  60

Gln Ala Lys Pro Thr Leu Ser Ala Gln Glu Arg Tyr Ala Met Gly Ile
65                  70                  75                  80

Pro Gly Gly Ser Ser Gly Thr Trp Ala Ser Pro Glu Gln Ala Gln Val
                85                  90                  95

Leu Phe Asp Tyr Met Lys Lys Glu Phe Pro Gly Trp Glu Pro Gly Tyr
            100                 105                 110

Ala Gly Leu Gly Asp Asn Arg Thr Ala Leu Phe Met Ala Thr Lys
            115                 120                 125

Phe Met Arg Met Gly Met Trp Pro Gly Glu Ile Asn Met Gly Gly Asn
        130                 135                 140

Arg Val Asn Val Ala Lys Ala Ile Ser Ala Ala Gly Gly Thr Ala Ala
145                 150                 155                 160

Phe Thr Ser Phe Leu Gly Leu Arg Ser Ser Glu Thr Leu Arg Pro Gln
            165                 170                 175

Asp Phe Gly Val Pro Arg Trp Glu Gly Thr Pro Glu Glu Asn Leu Leu
            180                 185                 190

Thr Leu Arg Gln Val Val Arg Phe Leu Gly Gly Cys Asp Val Gly Ala
        195                 200                 205

Gln Glu Met Asp Ser Asp Val Phe Lys Leu Phe His Glu Lys Ser Gly
        210                 215                 220

Lys Lys Gln Leu Val Ile Glu Asn Val Asp Glu Ala Ala Glu Thr Pro
225                 230                 235                 240

Thr Lys Leu Val Ile Pro Ala Lys Ala Lys Tyr Ile Leu Gln Trp Thr
            245                 250                 255

Ala Arg Gln Pro Tyr Glu Ser Thr Arg Arg Gln Ala Gly Glu Tyr Glu
            260                 265                 270

Asp Ala Ala Val Tyr Trp Ser Tyr Gln Arg Phe Pro Phe Val Gly Ala
            275                 280                 285

Ile Ile Gln Glu Phe Ile His Ala Leu Gly Tyr Thr Ala Val Ser Thr
        290                 295                 300

His Leu Ser Gly Tyr His Ser Ser Ala Val Ala Thr Leu Thr Gly Met
305                 310                 315                 320

Gly Glu His Cys Arg Met Ser Ser Pro Ile Leu Val Pro Lys Tyr Gly
            325                 330                 335

Val Thr Asn Arg Ala Met Trp Val Ile Met Thr Asp Met Pro Leu Met
            340                 345                 350

Ser Thr Lys Pro Ile Asp Phe Gly Val Tyr Asp Phe Cys Lys Thr Cys
            355                 360                 365

Gly Ile Cys Ala Asp Ala Cys Pro Phe Gly Leu Ile Glu Lys Gly Asp
            370                 375                 380

Pro Thr Trp Glu Ala Thr Gln Pro Gly Ser Arg Pro Gly Phe Asn Gly
385                 390                 395                 400

Trp Arg Thr Asn Thr Thr Ile Cys Pro His Cys Pro Val Cys Gln Ser
            405                 410                 415

Ser Cys Pro Phe Asn Thr Asn Gly Asp Gly Ser Phe Ile His Asp Leu
```

```
                    420                 425                 430
Val Arg Asn Thr Val Ser Thr Thr Pro Ile Phe Asn Ser Phe Phe Ala
                435                 440                 445

Asn Met Glu Lys Thr Met Gly Tyr Gly Arg Lys Asp Pro Arg Asp Trp
450                 455                 460

Trp Asn Ile Asp Asp Tyr Thr Tyr Gly Ile Asn Thr Ser Tyr
465                 470                 475

<210> SEQ ID NO 31
<211> LENGTH: 496
<212> TYPE: PRT
<213> ORGANISM: Dehalococcoides sp.

<400> SEQUENCE: 31

Gly Ala Gly Ile Gly Ala Ala Thr Ser Val Met Pro Asn Phe His Asp
1               5                  10                  15

Leu Asp Glu Val Ile Ser Ala Ala Ser Ala Glu Thr Ser Ser Leu Ser
                20                  25                  30

Gly Lys Ser Leu Asn Asn Phe Pro Trp Tyr Val Lys Glu Arg Asp Phe
            35                  40                  45

Glu Asn Pro Thr Ile Asp Ile Asp Trp Ser Ile Leu Ala Arg Asn Asp
50                  55                  60

Gly Tyr Asn His Gln Gly Ala Tyr Trp Gly Pro Val Pro Glu Asn Gly
65              70                  75                  80

Asp Asp Lys Arg Tyr Pro Asp Pro Ala Asp Gln Cys Leu Thr Leu Pro
                85                  90                  95

Glu Lys Arg Asp Leu Tyr Leu Ala Trp Ala Lys Gln Gln Phe Pro Asp
            100                 105                 110

Trp Glu Pro Gly Ile Asn Gly His Gly Pro Thr Arg Asp Glu Ala Leu
        115                 120                 125

Trp Phe Ala Ser Ser Thr Gly Gly Ile Gly Arg Tyr Arg Ile Pro Gly
130                 135                 140

Thr Gln Gln Met Met Ser Thr Met Arg Leu Asp Gly Ser Thr Gly Gly
145                 150                 155                 160

Trp Gly Tyr Phe Asn Gln Pro Pro Ala Ala Val Trp Gly Gly Lys Tyr
                165                 170                 175

Pro Arg Trp Glu Gly Thr Pro Glu Glu Asn Thr Leu Met Met Arg Thr
            180                 185                 190

Val Cys Gln Phe Phe Gly Tyr Ser Ser Ile Gly Val Met Pro Ile Thr
        195                 200                 205

Ser Asn Thr Lys Lys Leu Phe Phe Glu Lys Gln Ile Pro Phe Gln Phe
210                 215                 220

Met Ala Gly Asp Pro Gly Val Phe Gly Gly Thr Gly Asn Val Gln Phe
225                 230                 235                 240

Asp Val Pro Leu Pro Lys Thr Pro Val Pro Ile Val Trp Glu Glu Val
                245                 250                 255

Asp Lys Gly Tyr Tyr Asn Asp Gln Lys Ile Val Ile Pro Asn Lys Ala
            260                 265                 270

Asn Trp Val Leu Thr Met Thr Met Pro Leu Pro Glu Asp Arg Phe Lys
        275                 280                 285

Arg Ser Leu Gly Trp Ser Leu Asp Ala Ser Ser Met Ile Ala Tyr Pro
    290                 295                 300

Gln Met Ala Phe Asn Gly Gly Arg Val Gln Thr Phe Leu Lys Ala Leu
305                 310                 315                 320
```

```
Gly Tyr Gln Gly Leu Gly Gly Asp Val Ala Met Trp Gly Pro Gly Gly
                325                 330                 335

Ala Phe Gly Val Met Ser Gly Leu Ser Glu Gln Gly Arg Ala Ala Asn
            340                 345                 350

Glu Ile Ser Pro Lys Tyr Gly Ser Ala Thr Lys Gly Ser Asn Arg Leu
        355                 360                 365

Val Cys Asp Leu Pro Met Val Pro Thr Lys Pro Ile Asp Ala Gly Ile
370                 375                 380

His Lys Phe Cys Glu Thr Cys Gly Ile Cys Thr Thr Val Cys Pro Ser
385                 390                 395                 400

Asn Ala Ile Gln Val Gly Pro Pro Gln Trp Ser Asn Asn Arg Trp Asp
                405                 410                 415

Asn Thr Pro Gly Tyr Leu Gly Tyr Arg Leu Asn Trp Gly Arg Cys Val
            420                 425                 430

Leu Cys Thr Asn Cys Glu Thr Tyr Cys Pro Phe Phe Asn Met Thr Asn
        435                 440                 445

Gly Ser Leu Ile His Asn Val Val Arg Ser Thr Val Ala Ala Thr Pro
    450                 455                 460

Val Phe Asn Ser Phe Phe Arg Gln Met Glu His Thr Phe Gly Tyr Gly
465                 470                 475                 480

Met Lys Asp Asp Leu Asn Asp Trp Trp Asn Gln Ser His Lys Pro Trp
                485                 490                 495

<210> SEQ ID NO 32
<211> LENGTH: 507
<212> TYPE: PRT
<213> ORGANISM: Dehalococcoides sp.

<400> SEQUENCE: 32

Leu Gly Leu Val Gly Ala Gly Ala Gly Ala Ala Ala Val Ala Pro
1               5                   10                  15

Val Phe Arg Asp Leu Asp Asp Leu Val Ala Ser Pro Thr Ala Thr Phe
                20                  25                  30

Pro Arg Ala Trp Trp Ile Lys Glu Arg Asp Leu Trp Asp Ile Thr Thr
            35                  40                  45

Glu Tyr Asp Trp Lys Ala Met Ser Arg His Asp Thr Cys Glu Thr Met
        50                  55                  60

Trp Ile Lys His Ser Trp Ala Lys Tyr Val Gly Val Asp Lys Val Lys
65                  70                  75                  80

Glu Ala Ala Ala Ser Ala Ala Ala Ile Lys Lys Glu Ala Leu Glu Thr
                85                  90                  95

Gly Lys Pro Gly Met Asp Leu Arg Ala Thr Ala Leu Gly Ser Thr Ser
            100                 105                 110

Gly Leu Tyr Asn Ala Pro Gln Pro Tyr Phe Ser Tyr Thr Lys Thr Ala
        115                 120                 125

Gln Gly Trp Gly Gly Lys Ser Phe Thr Gly Gln Ser Thr Ile Lys
                130                 135                 140

Gly Pro Asp Val Leu Gly Val Pro Lys Trp Gln Gly Asp Pro Asp Ala
145                 150                 155                 160

Asn Leu Arg Met Leu Arg Ala Ala Leu Arg Phe Tyr Gly Ala Ala Gln
                165                 170                 175

Ile Gly Val Val Pro Tyr Asp Thr Asn Val Lys Asn Lys Leu Thr Cys
            180                 185                 190

Val Arg Glu Gly Gly Met Ala Ser Met Ser Asp Lys Tyr Ile Glu Lys
        195                 200                 205
```

Trp Pro Ile Pro Ala Val Asp Ala Arg Pro Phe Val Phe Glu Asp Val
210                 215                 220

Glu Lys Gly Tyr Glu Thr Ala Glu Lys Leu Val Ile Pro Asp Lys Lys
225                 230                 235                 240

Glu Leu Phe Val Val Ser Val Ile Gln Pro Met Ser Arg Glu Met Trp
            245                 250                 255

Arg Gln Gly Ser Gly Asn Leu Arg Val Ala Thr Asn Gly His Arg Tyr
            260                 265                 270

Ser Leu Ala Ser Val Trp Gln Thr Lys Ile Gln Gly Phe Leu Thr Thr
        275                 280                 285

Leu Gly Tyr Gln Gly Leu Gly Tyr Pro Thr Arg Ala Tyr Gly Ser Met
290                 295                 300

Pro Thr Ile Pro Gly Phe Ile Phe Ser Gly Leu Gly Glu Leu Gly Arg
305                 310                 315                 320

Ser Asn Asn Val Cys Leu Ser Pro Glu Tyr Gly Ser Thr His Gly Ser
                325                 330                 335

Phe His Phe Leu Thr Asp Leu Pro Leu Thr Pro Thr Lys Pro Ile Asp
            340                 345                 350

Ala Gly Met Trp Arg Phe Cys Lys Thr Cys Ala Ile Cys Ala Glu Asn
        355                 360                 365

Cys Pro Ser Gln Ser Ile Ser Tyr Asp Lys Glu Pro Ser Trp Glu Ile
370                 375                 380

Thr Pro Ser Lys Tyr Ala Pro Asn Val Pro Val Glu Tyr Ser Val Pro
385                 390                 395                 400

Gly Lys Lys Val Phe Trp Arg Asp Glu Pro Ser Cys Lys Gln Trp Thr
                405                 410                 415

Glu Ser Cys Gly Tyr Ser Cys Gly Ile Cys Met Gly Ser Cys Val Phe
            420                 425                 430

Asn Val Asp Asn Ala Ser Met Ile His Gln Val Val Lys Gly Thr Ile
        435                 440                 445

Ala Thr Thr Ser Leu Phe Asn Gly Phe Met Lys Gln Ala Asp Lys Phe
450                 455                 460

Phe Gly Tyr Gly Leu Thr Pro Glu Ser Glu Trp Asn Asn Trp Asp
465                 470                 475                 480

Met Asn Leu Pro Ala Tyr Ala Phe Asp Thr Thr Val Gly Val Thr Asp
                485                 490                 495

Gly Gly Tyr Lys Ala Lys Gly Leu Leu Gln Gln
            500                 505

<210> SEQ ID NO 33
<211> LENGTH: 515
<212> TYPE: PRT
<213> ORGANISM: Dehalococcoides sp.

<400> SEQUENCE: 33

Met His Asn Phe His Cys Thr Ile Ser Arg Arg Asp Phe Met Lys Gly
1               5                   10                  15

Leu Gly Leu Ala Gly Ala Gly Ile Gly Ala Ala Thr Ser Val Met Pro
            20                  25                  30

Asn Phe His Asp Leu Asp Glu Val Ile Ser Ala Ala Ser Ala Glu Thr
        35                  40                  45

Ser Ser Leu Ser Gly Lys Ser Leu Asn Asn Phe Pro Trp Tyr Val Lys
    50                  55                  60

Glu Arg Asp Phe Glu Asn Pro Thr Ile Asp Ile Asp Trp Ser Ile Leu

```
                65                  70                  75                  80
        Ala Arg Asn Asp Gly Tyr Asn His Gln Gly Ala Tyr Trp Gly Pro Val
                            85                  90                  95

Pro Glu Asn Gly Asp Asp Lys Arg Tyr Pro Asp Pro Ala Asp Gln Cys
                        100                 105                 110

Leu Thr Leu Pro Glu Lys Arg Asp Leu Tyr Leu Ala Trp Ala Lys Gln
                    115                 120                 125

Gln Phe Pro Asp Trp Glu Pro Gly Ile Asn Gly His Gly Pro Thr Arg
                130                 135                 140

Asp Glu Ala Leu Trp Phe Ala Ser Ser Thr Gly Gly Ile Gly Arg Tyr
        145                 150                 155                 160

Arg Ile Pro Gly Thr Gln Gln Met Met Ser Thr Met Arg Leu Asp Gly
                            165                 170                 175

Ser Thr Gly Gly Trp Gly Tyr Phe Asn Gln Pro Pro Ala Ala Val Trp
                        180                 185                 190

Gly Gly Lys Tyr Pro Arg Trp Glu Gly Thr Pro Glu Glu Asn Thr Leu
                    195                 200                 205

Met Met Arg Thr Val Cys Gln Phe Gly Tyr Ser Ser Ile Gly Val
                210                 215                 220

Met Pro Ile Thr Ser Asn Thr Lys Lys Leu Phe Glu Lys Gln Ile
        225                 230                 235                 240

Pro Phe Gln Phe Met Ala Gly Asp Pro Gly Val Phe Gly Thr Gly
                            245                 250                 255

Asn Val Gln Phe Asp Val Pro Leu Pro Lys Thr Pro Val Pro Ile Val
                        260                 265                 270

Trp Glu Glu Val Asp Lys Gly Tyr Tyr Asn Asp Gln Lys Ile Val Ile
                    275                 280                 285

Pro Asn Lys Ala Asn Trp Val Leu Thr Met Thr Met Pro Leu Pro Glu
                290                 295                 300

Asp Arg Phe Lys Arg Ser Leu Gly Trp Ser Leu Asp Ala Ser Ser Met
        305                 310                 315                 320

Ile Ala Tyr Pro Gln Met Ala Phe Asn Gly Gly Arg Val Gln Thr Phe
                            325                 330                 335

Leu Lys Ala Leu Gly Tyr Gln Gly Leu Gly Gly Asp Val Ala Met Trp
                        340                 345                 350

Gly Pro Gly Gly Ala Phe Gly Val Met Ser Gly Leu Ser Glu Gln Gly
                    355                 360                 365

Arg Ala Ala Asn Glu Ile Ser Pro Lys Tyr Gly Ser Ala Thr Lys Gly
                370                 375                 380

Ser Asn Arg Leu Val Cys Asp Leu Pro Met Val Pro Thr Lys Pro Ile
        385                 390                 395                 400

Asp Ala Gly Ile His Lys Phe Cys Glu Thr Cys Gly Ile Cys Thr Thr
                            405                 410                 415

Val Cys Pro Ser Asn Ala Ile Gln Val Gly Pro Pro Gln Trp Ser Asn
                        420                 425                 430

Asn Arg Trp Asp Asn Thr Pro Gly Tyr Leu Gly Tyr Arg Leu Asn Trp
                    435                 440                 445

Gly Arg Cys Val Leu Cys Thr Asn Cys Glu Thr Tyr Cys Pro Phe Phe
                450                 455                 460

Asn Met Thr Asn Gly Ser Leu Ile His Asn Val Val Arg Ser Thr Val
        465                 470                 475                 480

Ala Ala Thr Pro Val Phe Asn Ser Phe Phe Arg Gln Met Glu His Thr
                            485                 490                 495
```

```
Phe Gly Tyr Gly Met Lys Asp Asp Leu Asn Asp Trp Trp Asn Gln Ser
                500                 505                 510

His Lys Pro
        515

<210> SEQ ID NO 34
<211> LENGTH: 21
<212> TYPE: DNA
<213> ORGANISM: artificial
<220> FEATURE:
<223> OTHER INFORMATION: primer
<220> FEATURE:
<221> NAME/KEY: s
<222> LOCATION: (1)..(1)
<223> OTHER INFORMATION: c or g
<220> FEATURE:
<221> NAME/KEY: h
<222> LOCATION: (2)..(2)
<223> OTHER INFORMATION: a or c or t
<220> FEATURE:
<221> NAME/KEY: m
<222> LOCATION: (3)..(3)
<223> OTHER INFORMATION: a or c
<220> FEATURE:
<221> NAME/KEY: b
<222> LOCATION: (5)..(5)
<223> OTHER INFORMATION: c or g or t
<220> FEATURE:
<221> NAME/KEY: m
<222> LOCATION: (6)..(6)
<223> OTHER INFORMATION: a or c
<220> FEATURE:
<221> NAME/KEY: w
<222> LOCATION: (8)..(8)
<223> OTHER INFORMATION: a or t
<220> FEATURE:
<221> NAME/KEY: y
<222> LOCATION: (14)..(14)
<223> OTHER INFORMATION: c or t
<220> FEATURE:
<221> NAME/KEY: r
<222> LOCATION: (20)..(21)
<223> OTHER INFORMATION: a or g

<400> SEQUENCE: 34
shmgbmgwga tttyatgaar r                                          21

<210> SEQ ID NO 35
<211> LENGTH: 19
<212> TYPE: DNA
<213> ORGANISM: artificial
<220> FEATURE:
<223> OTHER INFORMATION: primer
<220> FEATURE:
<221> NAME/KEY: h
<222> LOCATION: (2)..(2)
<223> OTHER INFORMATION: a or c or t
<220> FEATURE:
<221> NAME/KEY: d
<222> LOCATION: (4)..(4)
<223> OTHER INFORMATION: a or g or t
<220> FEATURE:
<221> NAME/KEY: h
<222> LOCATION: (5)..(5)
<223> OTHER INFORMATION: a or c or t
<220> FEATURE:
<221> NAME/KEY: y
<222> LOCATION: (11)..(11)
<223> OTHER INFORMATION: c or t
<220> FEATURE:
<221> NAME/KEY: r
<222> LOCATION: (14)..(14)
<223> OTHER INFORMATION: a or g
```

-continued

```
<400> SEQUENCE: 35
chadhagcca ytcrtacca                                                  19

<210> SEQ ID NO 36
<211> LENGTH: 19
<212> TYPE: DNA
<213> ORGANISM: artificial
<220> FEATURE:
<223> OTHER INFORMATION: primer

<400> SEQUENCE: 36
accacctgta cttgaggca                                                  19

<210> SEQ ID NO 37
<211> LENGTH: 22
<212> TYPE: DNA
<213> ORGANISM: artificial
<220> FEATURE:
<223> OTHER INFORMATION: primer

<400> SEQUENCE: 37
acccgacaaa gaactggttt cg                                              22

<210> SEQ ID NO 38
<211> LENGTH: 159
<212> TYPE: PRT
<213> ORGANISM: D. ethenogenes
```

<400> SEQUENCE: 38

Leu Thr Asp Leu Pro Leu Ala Pro Asp Lys Pro Ile Asp Ala Gly Tyr
1               5                   10                  15

Phe Arg Phe Cys His Thr Cys Arg Lys Cys Ala Glu Ala Cys Pro Ser
            20                  25                  30

Gln Ala Ile Ser Phe Asp Ser Glu Pro Ser Trp Glu Ile Pro Pro Ser
        35                  40                  45

Ser Val Asp Pro Ala Lys Glu Thr Lys Tyr Ser Thr Pro Gly Lys Lys
    50                  55                  60

Val Phe His Thr Asp Ser Pro Ala Cys Tyr Ser Arg Trp Ile Gly Leu
65                  70                  75                  80

His Gly Cys Ala Arg Cys Met Gly Thr Cys Val Phe Asn Thr Asn Met
                85                  90                  95

Lys Ala Met Val His Asp Val Val Arg Ala Thr Val Gly Thr Thr Gly
            100                 105                 110

Leu Phe Asn Gly Phe Leu Trp Asn Ala Asp Lys Ala Phe Gly Tyr Gly
        115                 120                 125

Leu Val Pro Pro Glu Lys Trp Glu Trp Trp Asp Lys Asp Tyr Pro
    130                 135                 140

Val Leu Gly Gln Asp Ser Thr Ile Gly Ser Tyr Tyr Gly Gly Tyr
145                 150                 155

```
<210> SEQ ID NO 39
<211> LENGTH: 161
<212> TYPE: PRT
<213> ORGANISM: D. ethenogenes
```

<400> SEQUENCE: 39

Ile Thr Asp Leu Pro Leu Met Pro Thr Pro Ile Asp Ala Gly Ile
1               5                   10                  15

Phe Arg Phe Cys His Thr Cys Arg Lys Cys Ala Glu Ala Cys Pro Val
            20                  25                  30

```
Gly Gly Ile Ser Phe Glu Ala Glu Pro Ser Trp Glu Ile Pro Pro Ser
            35                  40                  45

Ala Ile Ala Thr Asp Lys Pro Ile Ser Phe Ser Thr Pro Gly Lys Arg
     50                  55                  60

Thr Tyr His Thr Asp Ala Leu Lys Cys Arg Leu Tyr Phe Asp Ala Gln
 65                  70                  75                  80

Pro Ser Tyr Cys Ala Arg Cys Met Gly Thr Cys Val Phe Asn Thr Asn
                 85                  90                  95

Thr Ser Ala Met Val His Glu Leu Val Lys Thr Thr Val Ser Ser Thr
             100                 105                 110

Gly Leu Leu Asn Gly Phe Leu Trp Asn Ala Asp Lys Ala Phe Gly Tyr
             115                 120                 125

Gly Leu Val Pro Ala Glu Glu Thr Ser Lys Trp Asp Leu Ser Leu
        130                 135                 140

Pro Leu Tyr Gly Gln Asp Gly Ser Ile Gly Ala Thr Asp Gly Gly Tyr
145                 150                 155                 160

Lys

<210> SEQ ID NO 40
<211> LENGTH: 150
<212> TYPE: PRT
<213> ORGANISM: D. ethenogenes

<400> SEQUENCE: 40

Ile Thr Asp Leu Pro Leu Pro Val Ser Lys Pro Ile Asp Phe Gly Ala
 1               5                  10                  15

Phe Arg Phe Cys His Ser Cys Arg Lys Cys Ala Asp Thr Cys Pro Ala
                 20                  25                  30

Lys Ala Ile Ser Phe Glu Glu Pro Thr Trp Glu Pro Ala Gly Pro
             35                  40                  45

Trp Ser Thr Ala Gly Lys Arg Ala Tyr Phe Lys Asn Glu Pro Glu Cys
 50                  55                  60

Lys Leu Tyr Gln His Ser Thr Gly Ala Thr Cys Gln Ile Cys Thr Gly
 65                  70                  75                  80

Val Cys Val Phe Asn Val Asn Thr Lys Ala Met Ile His Glu Val Val
                 85                  90                  95

Lys Ser Thr Leu Ser Thr Thr Gly Ile Phe Asn Ser Phe Leu Trp Lys
             100                 105                 110

Ala Asp Val Ala Phe Gly Tyr Gly His His Asp Ala Ala Glu Trp Trp
             115                 120                 125

Asp Leu Asp Leu Pro Arg Tyr Gly Phe Asp Thr Thr Met Gly Val Arg
        130                 135                 140

Asp Gly Gly Tyr Gly Lys
145                 150

<210> SEQ ID NO 41
<211> LENGTH: 160
<212> TYPE: PRT
<213> ORGANISM: D. ethenogenes

<400> SEQUENCE: 41

Ile Thr Asp Leu Pro Met Ala Pro Thr His Pro Ile Asp Ala Gly Ile
 1               5                  10                  15

Phe Arg Phe Cys His Thr Cys Lys Cys Ala Asp Glu Cys Pro Ala
                 20                  25                  30
```

```
Lys Cys Ile Asp Gln Gly Ser Glu Pro Thr Trp Asp Phe Pro Ala Ser
             35                  40                  45

Met Tyr Lys Pro Glu Met Pro Val Asp Tyr His Ala Pro Gly Lys Arg
 50                  55                  60

Leu Phe Trp Asn Asp Pro Ile Ala Cys Gln Met Tyr Ser Asn Ser Val
 65                  70                  75                  80

Ala Gly Ala Cys Gly Val Cys Met Ala Thr Cys Thr Phe Asn Thr Asn
                 85                  90                  95

Gly Ala Ser Met Ile His Asp Val Val Lys Ala Thr Leu Ala Lys Thr
                100                 105                 110

Ser Leu Leu Asn Gly Phe Leu Trp Asn Ala Asp Lys Ala Phe Gly Tyr
            115                 120                 125

Gly Leu Val Glu Gly Asp Glu Lys Glu Lys Phe Trp Glu Ile Gly Leu
        130                 135                 140

Pro Ala Tyr Gly Phe Asp Thr Thr Val Gly Ser Thr Val Gly Gly Tyr
145                 150                 155                 160

<210> SEQ ID NO 42
<211> LENGTH: 158
<212> TYPE: PRT
<213> ORGANISM: D. ethenogenes

<400> SEQUENCE: 42

Leu Thr Asp Leu Pro Leu Glu Pro Thr His Pro Ile Asp Ala Gly Ile
  1               5                  10                  15

Tyr Arg Phe Cys His Ser Cys Gln Lys Cys Ala Asp His Cys Pro Pro
                 20                  25                  30

Gln Val Ile Ser Lys Glu Lys Glu Pro Ser Trp Asp Ile Pro Leu Thr
             35                  40                  45

Glu Gly Lys Glu Thr Ile Phe Ser Val Lys Gly Thr Lys Ala Phe Tyr
 50                  55                  60

Asn Asn Leu Pro Leu Cys Arg Gln Tyr Ser Asn Glu Thr Ser His Gly
 65                  70                  75                  80

Cys Arg Ile Cys Trp Gly Glu Cys Thr Phe Thr Val Asn Arg Gly Ser
                 85                  90                  95

Leu Val His Gln Ile Ile Lys Gly Thr Val Ala Asn Val Ser Leu Phe
            100                 105                 110

Asn Thr Tyr Phe Tyr Lys Leu Gly Glu Ala Phe Gly Tyr Gly Ala Asp
            115                 120                 125

Ala Glu Lys Ala Glu Thr Trp Trp Asp Leu Ser Leu Pro Thr Leu Gly
        130                 135                 140

Gln Asp Ser Thr Ile Thr Ala Ala Asp Gly Gly Tyr Gly Lys
145                 150                 155

<210> SEQ ID NO 43
<211> LENGTH: 160
<212> TYPE: PRT
<213> ORGANISM: D. ethenogenes

<400> SEQUENCE: 43

Tyr Thr Asp Leu Pro Leu Pro Val Ile Asn Pro Ile Asp Ala Gly Phe
  1               5                  10                  15

Val Lys Phe Cys Glu Ile Cys Gly Ile Cys Ala Glu Thr Cys Pro Val
                 20                  25                  30

Gly Ala Ile Gln Glu Arg Gly Ile Asp Arg Ser Trp Asp Asn Asn Cys
            35                  40                  45
```

```
Gly Gln Ser Trp Ala Asp Asp Lys Gln Ala Gly Ser Lys Val Met
    50                  55                  60

Tyr Asn Ile Pro Gly Tyr Lys Gly Trp Arg Cys Asn Leu Phe Ser Cys
65                  70                  75                  80

Ala Phe Thr Pro Cys Ala Ser Ala Cys Lys Ser Asn Cys Pro Phe Asn
                85                  90                  95

Ala Ile Gly Asp Gly Ser Phe Val His Ser Ile Val Lys Ser Thr Val
                100                 105                 110

Ala Thr Ser Pro Ile Phe Asn Ser Phe Phe Thr Ser Met Glu Gly Val
            115                 120                 125

Leu His Tyr Gly Lys Gln Asp Lys Asp Pro Ala Ser Trp Trp Asn Ser
    130                 135                 140

Pro Asp Glu Trp Phe Ile Tyr Gly Thr His Pro Asn Leu Leu Arg Gln
145                 150                 155                 160

<210> SEQ ID NO 44
<211> LENGTH: 154
<212> TYPE: PRT
<213> ORGANISM: D. ethenogenes

<400> SEQUENCE: 44

Val Thr Asp Leu Pro Leu Ala Val Thr Lys Pro Ile Asp Ala Gly Met
1               5                   10                  15

Glu Arg Phe Cys Glu Thr Cys Gly Val Cys Gly Thr Gln Cys Pro Phe
                20                  25                  30

Gly Ala Ile Ala Met Gly Asp Lys Ser Trp Asp Asn Ala Cys Gly Gln
            35                  40                  45

Asp Trp Ala Ala Asp Gln Ser Val Gly Gly Asp Thr Cys Met Trp Asn
    50                  55                  60

Ile Pro Gly Tyr Asn Gly Trp Arg Leu Asp Tyr Arg Lys Cys Met Gly
65                  70                  75                  80

Asn Cys Cys Ser Cys Met Gly Ala Cys Pro Phe Gly Thr Ala Gly Ala
                85                  90                  95

Ser Leu Ile His Glu Val Val Lys Gly Thr Met Ser Val Thr Pro Val
            100                 105                 110

Phe Asn Ser Phe Phe Arg Ser Met Ser Glu Thr Phe Asn Tyr Gly His
        115                 120                 125

Lys Glu Pro Glu Ser Trp Trp Asp Leu Pro Leu Glu Gln Ile Pro Ala
    130                 135                 140

Tyr Gly Val Asn Pro Ala Leu Leu Val Lys
145                 150

<210> SEQ ID NO 45
<211> LENGTH: 137
<212> TYPE: PRT
<213> ORGANISM: D. ethenogenes

<400> SEQUENCE: 45

Leu Thr Asp Leu Pro Leu Ala Pro Thr Lys Pro Ile Asp Ala Gly Ile
1               5                   10                  15

Arg Glu Phe Cys Lys Thr Cys Gly Ile Cys Ala Glu His Cys Pro Thr
                20                  25                  30

Gln Ala Ile Ser His Glu Gly Pro Arg Tyr Asp Ser Pro His Trp Asp
            35                  40                  45

Cys Val Ser Gly Tyr Glu Gly Trp His Leu Asp Tyr Lys Cys Ile
    50                  55                  60
```

```
Asn Cys Thr Ile Cys Glu Ala Val Cys Pro Phe Thr Met Ser Asn
 65                  70                  75                  80

Asn Ser Trp Val His Asn Leu Val Lys Ser Thr Val Ala Thr Thr Pro
                 85                  90                  95

Val Phe Asn Gly Phe Lys Asn Met Glu Gly Ala Phe Gly Tyr Gly
                100                 105                 110

Pro Arg Tyr Ser Pro Ser Arg Asp Glu Trp Trp Ala Ser Glu Asn Pro
            115                 120                 125

Ile Arg Gly Ala Ser Val Asp Ile Phe
    130                 135
```

<210> SEQ ID NO 46
<211> LENGTH: 133
<212> TYPE: PRT
<213> ORGANISM: D. ethenogenes

<400> SEQUENCE: 46

```
Ile Thr Asp Met Pro Leu Met Ala Thr Lys Pro Ile Asp Phe Gly Val
 1               5                  10                  15

Tyr Lys Phe Cys Gln Thr Cys Gly Ile Cys Ala Asp Ser Cys Pro Phe
                20                  25                  30

Gly Leu Ile Glu Gln Gly Asp Pro Ser Trp Glu Ala Thr Gln Pro Gly
             35                  40                  45

Thr Arg Pro Gly Phe Asn Gly Trp Arg Thr Asn Thr Thr Thr Cys Pro
     50                  55                  60

His Cys Pro Val Cys Gln Gly Ser Cys Pro Phe Asn Thr Asn Gly Asp
 65                  70                  75                  80

Gly Ser Phe Ile His Asp Leu Val Arg Asn Thr Val Ser Val Thr Pro
                 85                  90                  95

Val Phe Asn Ser Phe Phe Ala Asn Met Glu Lys Thr Met Gly Tyr Gly
                100                 105                 110

Arg Lys Asp Pro Arg Asp Trp Trp Asn Ile Asp Asp Tyr Thr Tyr Gly
            115                 120                 125

Ile Asn Thr Ser Tyr
    130
```

<210> SEQ ID NO 47
<211> LENGTH: 133
<212> TYPE: PRT
<213> ORGANISM: D. ethenogenes

<400> SEQUENCE: 47

```
Leu Thr Asp Met Pro Leu Pro Pro Ser Arg Pro Ile Asp Phe Gly Ala
 1               5                  10                  15

Arg Lys Phe Cys Glu Thr Cys Gly Ile Cys Ala Glu Asn Cys Pro Phe
                20                  25                  30

Gly Ala Ile Asn Pro Gly Glu Pro Thr Trp Lys Asp Asp Asn Ala Phe
             35                  40                  45

Gly Asn Pro Gly Phe Leu Gly Trp Arg Cys Asp Tyr Thr Lys Cys Pro
     50                  55                  60

His Cys Pro Ile Cys Gln Gly Thr Cys Pro Phe Asn Ser His Pro Gly
 65                  70                  75                  80

Ser Phe Ile His Asp Val Val Lys Gly Thr Val Ser Thr Thr Pro Ile
                 85                  90                  95

Phe Asn Ser Phe Lys Asn Met Glu Lys Thr Phe Lys Tyr Gly Arg
                100                 105                 110
```

Lys Asn Pro Ala Thr Trp Trp Asp Glu Val Asp Asp Tyr Pro Tyr Gly
            115                 120                 125

Val Asp Thr Ser Tyr
        130

<210> SEQ ID NO 48
<211> LENGTH: 134
<212> TYPE: PRT
<213> ORGANISM: D. ethenogenes

<400> SEQUENCE: 48

Ile Thr Asn Phe Pro Ile Val Pro Thr Lys Pro Ile Asp Phe Gly Ser
1               5                   10                  15

Arg Glu Phe Cys Lys Thr Cys Lys Ile Cys Ala Glu Ala Cys Pro Phe
            20                  25                  30

Gly Ala Ile Lys Thr Gly Asp Pro Thr Trp Glu Asp Thr Ile Tyr
        35                  40                  45

Gly Asn Pro Gly Phe Leu Gly Trp His Cys Asn Tyr Asp Leu Cys Pro
50                  55                  60

His Cys Pro Val Cys Gln Gly Thr Cys Pro Phe Asn Thr Ile Arg Asp
65                  70                  75                  80

Asp Lys Ser Phe Ile His Glu Leu Val Arg Ile Ser Ala Ser His Thr
                85                  90                  95

Thr Val Phe Asn Thr Phe Phe Arg Asn Met Asp Leu Asn Phe Asp Tyr
            100                 105                 110

Gly Arg Lys Asp Gln Arg Asp Trp Trp Lys Glu Glu Asp Phe Pro Phe
        115                 120                 125

Gly Ile Asp Thr Ser Tyr
        130

<210> SEQ ID NO 49
<211> LENGTH: 136
<212> TYPE: PRT
<213> ORGANISM: D. ethenogenes

<400> SEQUENCE: 49

Leu Thr Asp Leu Pro Val Ala Pro Thr Lys Pro Ile Asp Phe Gly Ala
1               5                   10                  15

Tyr Lys Phe Cys Glu Thr Cys Gly Ile Cys Ala Asp Ala Cys Pro Phe
            20                  25                  30

Gly Leu Ile Gln Lys Gly Glu Ser Thr Trp Glu Asn Pro Ala Ala Ala
        35                  40                  45

Lys Asn Gly Leu Ala Gln Gly Gln Tyr Lys Gly Trp Arg Thr Asn Asn
50                  55                  60

Ala Asp Cys Pro His Cys Pro Thr Cys Gln Gly Thr Cys Pro Phe Asn
65                  70                  75                  80

Ser Thr Ser Gln Ser Phe Ile His Asp Met Val Lys Val Thr Thr Thr
                85                  90                  95

Asn Ile Pro Val Phe Asn Gly Phe Phe Ala Asn Met Glu Arg Phe Met
            100                 105                 110

Glu Tyr Gly Arg Lys Pro Gln Trp Glu Phe Trp Asp Ile Glu Gln Pro
        115                 120                 125

Thr Tyr Gly Phe Asp Thr Thr Ala
        130                 135

<210> SEQ ID NO 50
<211> LENGTH: 157

<212> TYPE: PRT
<213> ORGANISM: D. ethenogenes

<400> SEQUENCE: 50

Ile Val Asn Leu Pro Val Ala Pro Lys Lys Pro Ile Asp Phe Gly Ala
1               5                   10                  15

Arg Lys Phe Cys Ile Thr Cys Lys Lys Cys Ala Asp Leu Cys Pro Ser
                20                  25                  30

Gly Ala Leu Ser Lys Glu Thr Lys Leu Thr Trp Asp Ile Val Gln Ala
            35                  40                  45

Tyr Asp Ser Val Lys Pro Asn Leu Phe Asn Asn Pro Gly Leu Asn Asn
        50                  55                  60

Trp Pro Leu Asp His Phe Lys Cys Asn Arg Tyr Trp Asn Glu Ser Asp
65                  70                  75                  80

Thr Tyr Cys Gly Val Cys Gln Ala Val Cys Val Phe Ser Lys Asp Asp
                85                  90                  95

Ala Ser Ser Val His Glu Ile Val Lys Ala Thr Leu Ala Lys Thr Thr
            100                 105                 110

Met Leu Asn Ser Phe Phe Val Asn Met Asp Lys Gly Phe Gly Tyr Gly
        115                 120                 125

Leu Lys Pro Glu Asp Thr Ile Glu Glu Trp Trp Thr Asn Ser Phe Pro
    130                 135                 140

Val Asn Gly Ile His Tyr Asp Asn Asp Ala Tyr Tyr Asn
145                 150                 155

<210> SEQ ID NO 51
<211> LENGTH: 153
<212> TYPE: PRT
<213> ORGANISM: D. ethenogenes

<400> SEQUENCE: 51

Val Thr Asn Leu Pro Leu Pro Ala Asp Asn Pro Ile Asp Phe Gly Val
1               5                   10                  15

Val Ser Phe Cys Thr Thr Ala Cys Lys Lys Cys Ala Glu Phe Cys Pro
                20                  25                  30

Val Ser Ala Ile Lys Met Asp Ser Glu Pro Ser Trp Glu Leu Ala Thr
            35                  40                  45

Asp Pro Ser Asn Pro Tyr Leu Lys Pro Gln Asn Phe Asn Asn Pro Gly
        50                  55                  60

Arg Lys Thr Trp Tyr Leu Asn Gln Ala Gly Cys Phe Ser Asn Trp Cys
65                  70                  75                  80

Leu Thr Asp Thr Phe Cys Gly Ile Cys Met Gly Glu Cys Val Phe Asn
                85                  90                  95

Lys Leu Ala Asp Ser Ser Ile His Glu Val Val Lys Pro Val Ile Ala
            100                 105                 110

Asn Thr Thr Leu Leu Asp Gly Phe Phe Phe Asn Met Asp Lys Ala Phe
        115                 120                 125

Gly Tyr Gly Cys Leu Pro Glu Asp Gln Trp Glu Asp Trp Trp Thr Leu
    130                 135                 140

Gly Glu Lys Met Pro Ile His Gly Ile
145                 150

<210> SEQ ID NO 52
<211> LENGTH: 163
<212> TYPE: PRT
<213> ORGANISM: D. ethenogenes -continued

```
<400> SEQUENCE: 52

Phe Thr Asp Leu Pro Leu Pro Thr Thr Asn Pro Ile Asp Phe Gly Ala
1               5                   10                  15

Asn Arg Phe Cys Arg Asp Cys Gly Leu Cys Ala Lys Ala Cys Pro Ala
            20                  25                  30

Ser Ala Ile Pro Thr Phe Arg Glu Pro Thr Tyr Glu Ile Thr Pro Ala
        35                  40                  45

Asp Asp Ala Asn Ser Asn Pro Thr Lys Leu Ile Pro Glu Tyr Phe Asn
    50                  55                  60

Leu Ser Gly Lys Lys Val Trp Pro Asn Asn Asp Phe Ala Cys His Asn
65                  70                  75                  80

Phe Trp Val Thr Ser Gly Lys His Gly Cys Ala Ala Cys Val Ala Ser
                85                  90                  95

Cys Val Phe Ser Lys Asp Ile Lys Ser Ser Ile His Glu Val Val Lys
            100                 105                 110

Gly Val Val Ser Gln Thr Gly Ile Phe Asn Gly Phe Phe Ala Asn Met
        115                 120                 125

Asp His Ala Phe Gly Tyr Gly Ile Val Lys Asp Gln Asn Met Trp Asp
    130                 135                 140

Asn Phe Trp Phe Glu Pro Asp Lys Tyr Trp Pro Leu Glu Gly Ile Glu
145                 150                 155                 160

Thr Asn Leu

<210> SEQ ID NO 53
<211> LENGTH: 163
<212> TYPE: PRT
<213> ORGANISM: D. ethenogenes

<400> SEQUENCE: 53

Leu Thr Asp Leu Pro Leu Ala Pro Thr Lys Pro Ile Asp Phe Gly Val
1               5                   10                  15

Leu Lys Phe Cys Ser Thr Cys Gly Val Cys Ala Asn Ala Cys Pro Ser
            20                  25                  30

Gly Ala Ile Pro Thr Lys Glu Glu Met Lys Glu Pro Thr Trp Glu Arg
        35                  40                  45

Ser Thr Gly Pro Trp Ser Ser Ser Asn Asp His Lys Gly Tyr Pro Asn
    50                  55                  60

Glu Ser Val Lys Cys Ala Thr Trp Tyr Met Ala Asn Thr Val Ser Gly
65                  70                  75                  80

Phe Asn His Arg Pro Ile Gly Ala Cys Tyr Arg Cys Ala Ala Ala Cys
                85                  90                  95

Val Phe Asn Lys Ser Asn Glu Ala Trp Ile His Glu Ile Val Lys Ala
            100                 105                 110

Thr Val Ser Thr Thr Pro Leu Leu Asn Ser Phe Phe Ala Asn Met Asp
        115                 120                 125

Thr Gln Ala Gly Tyr Gly Glu Met Ser Pro Asp Glu Arg Ser Thr
    130                 135                 140

Leu Trp Thr Gly Asn Met Ala Glu Trp Gly Ile His Gln Tyr Gly Lys
145                 150                 155                 160

Asn Glu Trp

<210> SEQ ID NO 54
<211> LENGTH: 155
<212> TYPE: PRT
<213> ORGANISM: Dehalospirllum multivorans
```

<400> SEQUENCE: 54

Phe Thr Asn Met Pro Leu Val Pro Asp Lys Pro Ile Asp Phe Gly Val
1               5                   10                  15

Thr Glu Phe Cys Glu Thr Cys Lys Lys Cys Ala Arg Glu Cys Pro Ser
            20                  25                  30

Lys Ala Ile Thr Glu Gly Pro Arg Thr Phe Glu Gly Arg Ser Ile His
        35                  40                  45

Asn Gln Ser Gly Lys Leu Gln Trp Gln Asn Asp Tyr Asn Lys Cys Leu
    50                  55                  60

Gly Tyr Trp Pro Glu Ser Gly Gly Tyr Cys Gly Val Cys Val Ala Val
65                  70                  75                  80

Cys Pro Phe Thr Lys Gly Asn Ile Trp Ile His Asp Gly Val Glu Trp
                85                  90                  95

Leu Ile Asp Asn Thr Arg Phe Leu Asp Pro Leu Met Leu Gly Met Asp
            100                 105                 110

Asp Ala Leu Gly Tyr Gly Ala Lys Arg Asn Ile Thr Glu Val Trp Asp
        115                 120                 125

Gly Lys Ile Asn Thr Tyr Gly Leu Asp Ala Asp His Phe Arg Asp Thr
    130                 135                 140

Val Ser Phe Arg Lys Asp Arg Val Lys Lys Ser
145                 150                 155

<210> SEQ ID NO 55
<211> LENGTH: 151
<212> TYPE: PRT
<213> ORGANISM: Dehalobacter restrictus

<400> SEQUENCE: 55

Tyr Thr Asp Leu Glu Leu Ala Pro Asp Lys Pro Arg Lys Phe Gly Val
1               5                   10                  15

Arg Glu Phe Cys Arg Leu Cys Lys Lys Cys Ala Asp Ala Cys Pro Ala
            20                  25                  30

Gln Ala Ile Ser His Glu Lys Asp Pro Lys Val Leu Gln Pro Glu Asp
        35                  40                  45

Cys Glu Val Ala Glu Asn Pro Tyr Thr Glu Lys Trp His Leu Asp Ser
    50                  55                  60

Asn Arg Cys Gly Ser Phe Trp Ala Tyr Asn Gly Ser Pro Cys Ala Asn
65                  70                  75                  80

Cys Val Ala Val Cys Ser Trp Asn Lys Val Glu Thr Trp Asn His Asp
                85                  90                  95

Val Ala Arg Ile Ala Thr Gln Ile Pro Leu Leu Gln Asp Ala Ala Arg
            100                 105                 110

Lys Phe Asp Glu Trp Phe Gly Tyr Asn Gly Pro Val Asn Pro Asp Glu
        115                 120                 125

Arg Leu Glu Ser Gly Tyr Val Gln Asn Met Val Lys Asp Phe Trp Asn
    130                 135                 140

Asn Pro Glu Ser Ile Lys Gln
145                 150

<210> SEQ ID NO 56
<211> LENGTH: 151
<212> TYPE: PRT
<213> ORGANISM: Desulfitobacterium frappieri

<400> SEQUENCE: 56

Tyr Thr Asp Leu Glu Leu Ala Pro Asp Lys Pro Arg Lys Phe Gly Val
1               5                   10                  15

Arg Glu Phe Cys Arg Leu Cys Lys Lys Cys Ala Asp Ala Cys Pro Ala
            20                  25                  30

Gln Ala Ile Ser His Glu Lys Asp Pro Lys Val Leu Gln Pro Glu Asp
        35                  40                  45

Cys Glu Val Ala Glu Asn Pro Tyr Thr Glu Lys Trp His Leu Asp Ser
    50                  55                  60

Asn Arg Cys Gly Ser Phe Trp Ala Tyr Asn Gly Ser Pro Cys Ser Asn
65                  70                  75                  80

Cys Val Ala Val Cys Ser Trp Asn Lys Val Glu Thr Trp Asn His Asp
                85                  90                  95

Val Ala Arg Ile Ala Thr Gln Ile Pro Leu Leu Gln Asp Ala Ala Arg
            100                 105                 110

Lys Phe Asp Glu Trp Phe Gly Tyr Asn Gly Pro Val Asn Pro Asp Glu
        115                 120                 125

Arg Leu Glu Ser Gly Tyr Val Gln Asn Met Val Lys Asp Phe Trp Asn
    130                 135                 140

Asn Pro Glu Ser Ile Lys Gln
145                 150

<210> SEQ ID NO 57
<211> LENGTH: 151
<212> TYPE: PRT
<213> ORGANISM: Desulfitobacterium sp. Y51

<400> SEQUENCE: 57

Tyr Thr Asp Leu Glu Leu Ala Pro Asp Lys Pro Arg Lys Phe Gly Val
1               5                   10                  15

Arg Glu Phe Cys Arg Leu Cys Lys Lys Cys Ala Asp Ala Cys Pro Ala
            20                  25                  30

Gln Ala Ile Ser His Glu Lys Asp Pro Lys Val Leu Gln Pro Glu Asp
        35                  40                  45

Cys Glu Val Ala Glu Asn Pro Tyr Thr Glu Lys Trp His Leu Asp Ser
    50                  55                  60

Asn Arg Cys Gly Ser Phe Trp Ala Tyr Asn Gly Ser Pro Cys Ser Asn
65                  70                  75                  80

Cys Val Ala Val Cys Ser Trp Asn Lys Val Glu Thr Trp Asn His Asp
                85                  90                  95

Val Ala Arg Val Ala Thr Gln Ile Pro Leu Leu Gln Asp Ala Ala Arg
            100                 105                 110

Lys Phe Asp Glu Trp Phe Gly Tyr Asn Gly Pro Val Asn Pro Asp Glu
        115                 120                 125

Arg Leu Glu Ser Gly Tyr Val Gln Asn Met Val Lys Asp Phe Trp Asn
    130                 135                 140

Asn Pro Glu Ser Ile Lys Gln
145                 150

<210> SEQ ID NO 58
<211> LENGTH: 137
<212> TYPE: PRT
<213> ORGANISM: Desulfitobacterium dehalogenans

<400> SEQUENCE: 58

Thr Thr Asp Leu Pro Leu Ala Pro Asp Lys Pro Ile Asp Phe Gly Leu
1               5                   10                  15

Leu Asp Phe Cys Arg Val Cys Lys Lys Cys Ala Asp Asn Cys Pro Asn
            20                  25                  30

Asp Ala Ile Thr Phe Asp Glu Asp Pro Ile Glu Tyr Asn Gly Tyr Leu
        35                  40                  45

Arg Trp Asn Ser Asp Phe Lys Lys Cys Thr Glu Phe Arg Thr Thr Asn
 50                  55                  60

Glu Glu Gly Ser Ser Cys Gly Thr Cys Leu Lys Val Cys Pro Trp Asn
65                  70                  75                  80

Ser Lys Glu Asp Ser Trp Phe His Lys Ala Gly Val Trp Val Gly Ser
                85                  90                  95

Lys Gly Glu Ala Ala Ser Thr Phe Leu Lys Ser Ile Asp Asp Ile Phe
            100                 105                 110

Gly Tyr Gly Thr Glu Thr Ile Glu Lys Tyr Lys Trp Trp Leu Glu Trp
        115                 120                 125

Pro Glu Lys Tyr Pro Leu Lys Pro Met
    130                 135

<210> SEQ ID NO 59
<211> LENGTH: 137
<212> TYPE: PRT
<213> ORGANISM: Desulfitobacterium sp. Viet-1

<400> SEQUENCE: 59

Thr Thr Asp Met Pro Leu Ala Pro Asp Lys Pro Ile Asp Phe Gly Leu
1               5                   10                  15

Leu Asp Phe Cys Arg Val Cys Lys Lys Cys Ala Asp Asn Cys Pro Asn
            20                  25                  30

Asp Ala Ile Thr Phe Asp Glu Asp Pro Ile Glu Tyr Asn Gly Tyr Leu
        35                  40                  45

Arg Trp Asn Ser Asp Phe Lys Lys Cys Thr Glu Phe Arg Thr Thr Asn
 50                  55                  60

Glu Glu Gly Ser Ser Cys Gly Thr Cys Leu Lys Val Cys Pro Trp Asn
65                  70                  75                  80

Ser Lys Glu Asp Ser Trp Phe His Lys Ala Gly Val Trp Val Gly Ser
                85                  90                  95

Lys Gly Glu Ala Ala Ser Thr Phe Leu Lys Ser Ile Asp Asp Ile Phe
            100                 105                 110

Gly Tyr Gly Thr Glu Thr Ile Glu Lys Tyr Lys Trp Trp Leu Glu Trp
        115                 120                 125

Pro Glu Lys Tyr Pro Leu Lys Pro Met
    130                 135

<210> SEQ ID NO 60
<211> LENGTH: 135
<212> TYPE: PRT
<213> ORGANISM: Desulfitobacterium hafniense

<400> SEQUENCE: 60

Thr Thr Asp Leu Pro Leu Ala Pro Asp Gln Pro Leu Asp Phe Gly Leu
1               5                   10                  15

Leu Asp Phe Cys Arg Val Cys Lys Lys Cys Ala Asp Asn Cys Pro Asn
            20                  25                  30

Glu Ala Ile Ser Phe Asp Glu Asp Pro Ile Glu Tyr Asn Gly Tyr Leu
        35                  40                  45

Arg Trp Asn Ser Asp Phe Arg Lys Cys Thr Glu Phe Arg Thr Thr Asn
 50                  55                  60

```
Glu Glu Gly Ser Ser Cys Gly Thr Cys Met Lys Val Cys Pro Trp Asn
 65                  70                  75                  80

Ser Lys Glu Asp Ser Trp Phe His Lys Ala Gly Val Trp Val Gly Ser
                 85                  90                  95

Lys Gly Glu Thr Ala Ser Thr Phe Leu Lys Ser Ile Asp Asp Ile Phe
            100                 105                 110

Gly Tyr Gly Thr Glu Thr Ile Glu Lys Tyr Lys Trp Trp Leu Glu Trp
        115                 120                 125

Pro Glu Lys Tyr Val Met Lys
    130                 135

<210> SEQ ID NO 61
<211> LENGTH: 135
<212> TYPE: PRT
<213> ORGANISM: Desulfitobacterium chlororespirans

<400> SEQUENCE: 61

Thr Thr Asp Leu Pro Leu Glu Pro Asp Lys Pro Ile Asp Phe Gly Leu
1               5                   10                  15

Gln Asp Phe Cys Arg Ile Cys Gly Lys Cys Ala Glu Asn Cys Pro Gly
            20                  25                  30

Glu Ala Ile Thr Thr Asp Arg Asp His Val Glu Phe Asn Gly Tyr Leu
        35                  40                  45

Arg Trp Asn Ser Asp Met Lys Lys Cys Ala Val Phe Arg Thr Thr Asn
 50                  55                  60

Glu Glu Gly Ser Ser Cys Gly Arg Cys Met Lys Val Cys Pro Trp Asn
 65                  70                  75                  80

Ser Lys Glu Asp Ser Trp Phe His Glu Ala Gly Leu Trp Ile Gly Ser
                 85                  90                  95

Arg Gly Glu Met Ala Ser Ser Leu Leu Lys Asn Ile Asp Met Phe
            100                 105                 110

Gly Tyr Gly Thr Glu Thr Ile Asp Lys Tyr Lys Trp Trp Leu Glu Trp
        115                 120                 125

Pro Glu Leu Tyr Lys Ile Gln
    130                 135

<210> SEQ ID NO 62
<211> LENGTH: 126
<212> TYPE: PRT
<213> ORGANISM: D. ethenogenes

<400> SEQUENCE: 62

Phe Thr Asn Leu Pro Leu Val Pro Asp Lys Pro Ile Asp Phe Gly Leu
1               5                   10                  15

Gln Glu Phe Cys Lys Val Cys Lys Cys Ala Asp Asn Cys Pro Ala
            20                  25                  30

Ser Ala Ile Ser Met Asp Asp Glu Pro Ser Glu Val Asp Thr Val Val
        35                  40                  45

Lys Ser Ile Arg Trp Phe Gln Asp Gly Lys Lys Cys Leu Ser Gln Arg
 50                  55                  60

Leu Ala Tyr Gly Cys Ser Lys Cys Gln Ser Val Cys Pro Trp Ser Lys
 65                  70                  75                  80

Pro Asp Thr Leu Ile His Glu Ile Gly Arg Met Val Gly Gln Asn Pro
                 85                  90                  95

Ala Phe Ala Pro Phe Leu Val Lys Leu Asp Asp Phe Tyr Asn Arg
            100                 105                 110
```

-continued

```
Tyr Pro Glu Gly His Ala Thr Gly Glu Trp Ala Pro Trp Arg
        115                 120                 125

<210> SEQ ID NO 63
<211> LENGTH: 155
<212> TYPE: PRT
<213> ORGANISM: D. ethenogenes

<400> SEQUENCE: 63

Thr Thr Ser Leu Pro Leu Ala Ala Asp Lys Pro Val Asp Phe Asn Leu
1               5                   10                  15

Ala Glu Phe Cys Ser Arg Cys Lys Leu Cys Ala Gln Val Cys Pro Thr
            20                  25                  30

Gln Ala Ile Ser Tyr Asp Asp Lys Pro Lys Phe Glu Ile Tyr Gly Gln
            35                  40                  45

Arg Arg Phe Asn Thr Asn Leu Ala Lys Cys Arg Asp Gly Trp Asn Leu
50                  55                  60

Gly Ala Gly Pro Met Gly Cys Arg Ala Cys Ile Ser Val Cys Pro Trp
65                  70                  75                  80

Thr Lys Lys Asn Thr Trp Val His Arg Phe Val Arg Glu Val Leu Ser
            85                  90                  95

His Asp Ala Thr Gly Thr Ser Gln Asn Ile Ala Ile Trp Ala Glu Arg
            100                 105                 110

Thr Leu Tyr Pro Lys His Tyr Gln Glu Glu Leu Asn Pro Pro Asn Tyr
            115                 120                 125

Gln Gly Val Tyr Glu Pro Pro Lys Trp Ile Gln Thr Asn Glu Tyr Val
            130                 135                 140

Ser Ser Phe Val Asn Thr Pro Met Gly Val Lys
145                 150                 155
```